(12) United States Patent
Coza et al.

(10) Patent No.: US 10,244,984 B2
(45) Date of Patent: Apr. 2, 2019

(54) WEARABLE ATHLETIC ACTIVITY MONITORING SYSTEMS

(71) Applicant: adidas AG, Herzogenaurach (DE)

(72) Inventors: Aurel Coza, Portland, OR (US); Christian DiBenedetto, North Plains, OR (US); Ian Michael Munson, Portland, OR (US)

(73) Assignee: adidas AG, Herzogenaurach (DE)

( * ) Notice: Subject to any disclaimer, the term of this patent is extended or adjusted under 35 U.S.C. 154(b) by 48 days.

(21) Appl. No.: 15/659,679

(22) Filed: Jul. 26, 2017

(65) Prior Publication Data

US 2017/0319133 A1    Nov. 9, 2017

Related U.S. Application Data

(63) Continuation of application No. 13/797,274, filed on Mar. 12, 2013, now Pat. No. 9,737,261, which is a continuation-in-part of application No. 13/446,986, filed on Apr. 13, 2012, now Pat. No. 9,504,414.

(51) Int. Cl.
| | |
|---|---|
| *A63B 24/00* | (2006.01) |
| *A61B 5/00* | (2006.01) |
| *A61B 5/11* | (2006.01) |
| *A61B 5/04* | (2006.01) |
| *G09B 19/00* | (2006.01) |

(Continued)

(52) U.S. Cl.
CPC .......... *A61B 5/6804* (2013.01); *A61B 5/0002* (2013.01); *A61B 5/002* (2013.01); *A61B 5/0022* (2013.01); *A61B 5/04005* (2013.01); *A61B 5/11* (2013.01); *G06F 19/00* (2013.01); *G09B 19/0038* (2013.01); *G16H 40/67* (2018.01)

(58) Field of Classification Search
CPC ..... A61B 5/6804; A61B 5/0002; A61B 5/002; A61B 5/0022; A61B 5/04005; G16H 40/67; G06F 19/00; G06F 19/0038
USPC .......................................................... 700/91
See application file for complete search history.

(56) References Cited

U.S. PATENT DOCUMENTS

| | | |
|---|---|---|
| 4,202,350 A | 5/1980 | Walton |
| 4,312,358 A | 1/1982 | Barney |
| 4,572,197 A | 2/1986 | Moore et al. |

(Continued)

FOREIGN PATENT DOCUMENTS

| | | |
|---|---|---|
| CN | 101224337 A | 7/2008 |
| CN | 101701823 A | 5/2010 |

(Continued)

OTHER PUBLICATIONS

Yun, X., et al., "A Simplified Quaternion-Based Algorithm for Orientation Estimation From Earth Gravity and Magnetic Field Measurements," IEEE Transactions on Instrumentation and Measurement, vol. 57, No. 3, pp. 638-650, Mar. 2008.

(Continued)

*Primary Examiner* — Allen Chan
(74) *Attorney, Agent, or Firm* — Sterne, Kessler, Goldstein & Fox P.L.L.C.

(57) ABSTRACT

A sensor garment for monitoring an individual engaged in an athletic activity includes a garment formed of textile material, and a sensor module inseparably coupled to the textile material of the garment. The sensor module includes a single-purpose sensor configured to sense a single characteristic, and a radio antenna configured to transmit data generated by the single-purpose sensor. The sensor module includes no external port.

20 Claims, 27 Drawing Sheets

(51) Int. Cl.
   *G06F 19/00* (2018.01)
   *G16H 40/67* (2018.01)

(56) References Cited

U.S. PATENT DOCUMENTS

| | | | |
|---|---|---|---|
| 4,580,572 A | 4/1986 | Granek et al. |
| 4,889,131 A | 12/1989 | Salem et al. |
| 4,909,260 A | 3/1990 | Salem et al. |
| 4,962,469 A | 10/1990 | Ono et al. |
| 5,007,427 A | 4/1991 | Suzuki et al. |
| 5,111,818 A | 5/1992 | Suzuki et al. |
| 5,148,002 A | 9/1992 | Kuo et al. |
| 5,153,584 A | 10/1992 | Engira |
| 5,204,670 A | 4/1993 | Stinton |
| 5,210,540 A | 5/1993 | Masumoto |
| 5,353,793 A | 10/1994 | Bornn |
| 5,400,254 A | 3/1995 | Fujita |
| 5,583,776 A | 12/1996 | Levi et al. |
| 5,592,401 A | 1/1997 | Kramer |
| 5,611,085 A | 3/1997 | Rasmussen |
| 5,724,025 A | 3/1998 | Tavori |
| 5,724,265 A | 3/1998 | Hutchings |
| 5,769,755 A | 6/1998 | Henry et al. |
| 5,802,492 A | 9/1998 | DeLorme et al. |
| 5,825,327 A | 10/1998 | Krasner |
| 5,899,963 A | 5/1999 | Hutchings |
| 5,947,868 A | 9/1999 | Dugan |
| 5,948,040 A | 9/1999 | DeLorme et al. |
| 5,955,667 A | 9/1999 | Fyfe |
| 5,976,083 A | 11/1999 | Richardson et al. |
| 5,989,157 A | 11/1999 | Walton |
| 6,002,982 A | 12/1999 | Fry |
| 6,013,007 A | 1/2000 | Root et al. |
| 6,032,108 A | 2/2000 | Seiple et al. |
| 6,047,203 A | 4/2000 | Sackner et al. |
| 6,066,093 A | 5/2000 | Kelly et al. |
| 6,097,345 A | 8/2000 | Walton |
| 6,122,340 A | 9/2000 | Darley et al. |
| 6,135,951 A | 10/2000 | Richardson et al. |
| 6,145,389 A | 11/2000 | Ebeling et al. |
| 6,148,262 A | 11/2000 | Fry |
| 6,148,271 A | 11/2000 | Marinelli |
| 6,151,563 A | 11/2000 | Marinelli |
| 6,157,898 A | 12/2000 | Marinelli |
| 6,167,356 A | 12/2000 | Squadron et al. |
| 6,181,647 B1 | 1/2001 | Tipton et al. |
| 6,198,394 B1 | 3/2001 | Jacobsen et al. |
| 6,204,807 B1 | 3/2001 | Odagiri et al. |
| 6,234,257 B1 | 5/2001 | Ciglenec et al. |
| 6,246,362 B1 | 6/2001 | Tsubata et al. |
| 6,254,551 B1 | 7/2001 | Varis |
| 6,266,623 B1 | 7/2001 | Vock et al. |
| 6,298,314 B1 | 10/2001 | Blackadar et al. |
| 6,301,964 B1 | 10/2001 | Fyfe et al. |
| 6,305,221 B1 | 10/2001 | Hutchings |
| 6,336,365 B1 | 1/2002 | Blackadar et al. |
| 6,356,856 B1 | 3/2002 | Damen et al. |
| 6,357,147 B1 | 3/2002 | Darley et al. |
| 6,381,482 B1 | 4/2002 | Jayaraman et al. |
| 6,389,894 B1 | 5/2002 | Calame |
| 6,443,890 B1 | 9/2002 | Schulze |
| 6,463,385 B1 | 10/2002 | Fry |
| 6,478,736 B1 | 11/2002 | Mault |
| 6,493,652 B1 | 12/2002 | Ohlenbusch et al. |
| 6,513,381 B2 | 2/2003 | Fyfe et al. |
| 6,513,532 B2 | 2/2003 | Mault et al. |
| 6,536,139 B2 | 3/2003 | Darley et al. |
| 6,551,252 B2 | 4/2003 | Sackner et al. |
| 6,582,330 B1 | 6/2003 | Rehkemper et al. |
| 6,585,622 B1 | 7/2003 | Shum et al. |
| 6,590,536 B1 | 7/2003 | Walton |
| 6,611,789 B1 | 8/2003 | Darley |
| 6,616,613 B1 | 9/2003 | Goodman |
| 6,626,799 B2 | 9/2003 | Watterson et al. |
| 6,716,139 B1 | 4/2004 | Hosseinzadeh-Dolkhani et al. |
| 6,736,759 B1 | 5/2004 | Stubbs et al. |
| 6,745,069 B2 | 6/2004 | Nissila et al. |
| 6,790,178 B1 | 9/2004 | Mault et al. |
| 6,798,378 B1 | 9/2004 | Walters |
| 6,832,109 B2 | 12/2004 | Nissila |
| 6,876,947 B1 | 4/2005 | Darley et al. |
| 6,882,955 B1 | 4/2005 | Ohlenbusch et al. |
| 6,885,971 B2 | 4/2005 | Vock et al. |
| 6,898,550 B1 | 5/2005 | Blackadar et al. |
| 6,959,259 B2 | 10/2005 | Vock et al. |
| 6,970,731 B1 | 11/2005 | Jayaraman et al. |
| 7,062,225 B2 | 6/2006 | White |
| 7,072,789 B2 | 7/2006 | Vock et al. |
| 7,092,846 B2 | 8/2006 | Vock et al. |
| 7,171,331 B2 | 1/2007 | Vock et al. |
| 7,187,924 B2 | 3/2007 | Ohlenbusch et al. |
| 7,200,517 B2 | 4/2007 | Darley et al. |
| 7,220,220 B2 | 5/2007 | Stubbs et al. |
| 7,251,454 B2 | 7/2007 | White |
| 7,254,516 B2 | 8/2007 | Case, Jr. et al. |
| 7,273,431 B2 | 9/2007 | DeVall |
| 7,292,867 B2 | 11/2007 | Werner et al. |
| 7,428,472 B2 | 9/2008 | Darley et al. |
| 7,457,724 B2 | 11/2008 | Vock et al. |
| 7,467,060 B2 | 12/2008 | Kulach et al. |
| 7,480,512 B2 | 1/2009 | Graham et al. |
| 7,552,031 B2 | 6/2009 | Vock et al. |
| 7,559,902 B2 | 7/2009 | Ting et al. |
| 7,647,196 B2 | 1/2010 | Kahn et al. |
| 7,650,257 B2 | 1/2010 | Alexander et al. |
| 7,670,263 B2 | 3/2010 | Ellis et al. |
| 7,670,295 B2 | 3/2010 | Sackner et al. |
| 7,680,523 B2 | 3/2010 | Rytky |
| 7,689,378 B2 | 3/2010 | Kolen |
| 7,698,830 B2 | 4/2010 | Townsend et al. |
| 7,706,815 B2 | 4/2010 | Graham et al. |
| 7,715,982 B2 | 5/2010 | Grenfell et al. |
| 7,805,149 B2 | 9/2010 | Werner et al. |
| 7,805,150 B2 | 9/2010 | Graham et al. |
| 7,844,415 B1 | 11/2010 | Bryant et al. |
| 7,890,291 B2 | 2/2011 | Godin et al. |
| 7,891,666 B2 | 2/2011 | Kuenzler et al. |
| 7,980,998 B2 | 7/2011 | Shemesh et al. |
| 8,060,337 B2 | 11/2011 | Kulach et al. |
| 8,253,586 B1 | 8/2012 | Matak |
| 8,540,560 B2 | 9/2013 | Crowley et al. |
| 8,579,632 B2 | 11/2013 | Crowley |
| 8,818,478 B2 | 8/2014 | Scheffler et al. |
| 9,141,759 B2 | 9/2015 | Burich et al. |
| 9,257,054 B2 | 2/2016 | Coza et al. |
| 9,317,660 B2 | 4/2016 | Burich et al. |
| 9,504,414 B2 | 11/2016 | Coza et al. |
| 2002/0032386 A1 | 3/2002 | Sackner et al. |
| 2002/0068873 A1 | 6/2002 | Nissila |
| 2002/0107433 A1 | 8/2002 | Mault |
| 2002/0160883 A1 | 10/2002 | Dugan |
| 2003/0073518 A1 | 4/2003 | Marty et al. |
| 2003/0163287 A1 | 8/2003 | Vock et al. |
| 2003/0208409 A1 | 11/2003 | Mault |
| 2003/0224337 A1 | 12/2003 | Shum et al. |
| 2004/0046692 A1 | 3/2004 | Robson et al. |
| 2004/0102931 A1 | 5/2004 | Ellis et al. |
| 2004/0171956 A1 | 9/2004 | Babashan |
| 2004/0177531 A1 | 9/2004 | DiBenedetto et al. |
| 2004/0199056 A1 | 10/2004 | Husemann et al. |
| 2004/0209600 A1 | 10/2004 | Werner et al. |
| 2005/0010096 A1 | 1/2005 | Blackadar |
| 2005/0014113 A1 | 1/2005 | Fleck et al. |
| 2005/0054941 A1 | 3/2005 | Ting et al. |
| 2005/0143199 A1 | 6/2005 | Saroyan |
| 2005/0195094 A1 | 9/2005 | White |
| 2005/0197063 A1 | 9/2005 | White |
| 2005/0227811 A1 | 10/2005 | Shum et al. |
| 2005/0233815 A1 | 10/2005 | McCreary et al. |
| 2005/0250458 A1 | 11/2005 | Graham et al. |
| 2005/0266961 A1 | 12/2005 | Shum et al. |
| 2005/0275416 A1 | 12/2005 | Hervieux et al. |
| 2006/0020421 A1 | 1/2006 | Darley et al. |
| 2006/0025282 A1 | 2/2006 | Redmann |

(56) References Cited

U.S. PATENT DOCUMENTS

| | | |
|---|---|---|
| 2006/0135297 A1 | 6/2006 | Cruciani |
| 2006/0136173 A1 | 6/2006 | Case, Jr. et al. |
| 2006/0148594 A1 | 7/2006 | Saintoyant et al. |
| 2006/0189360 A1 | 8/2006 | White |
| 2006/0240865 A1 | 10/2006 | White |
| 2006/0246869 A1 | 11/2006 | Ohlenbusch et al. |
| 2007/0006489 A1 | 1/2007 | Case, Jr. et al. |
| 2007/0011919 A1 | 1/2007 | Case, Jr. |
| 2007/0021269 A1 | 1/2007 | Shum |
| 2007/0032318 A1 | 2/2007 | Nishimura et al. |
| 2007/0059675 A1 | 3/2007 | Kuenzler et al. |
| 2007/0060425 A1 | 3/2007 | Kuenzler et al. |
| 2007/0061105 A1 | 3/2007 | Darley et al. |
| 2007/0089800 A1 | 4/2007 | Sharma |
| 2007/0191083 A1 | 8/2007 | Kuenzler et al. |
| 2007/0203665 A1 | 8/2007 | Darley et al. |
| 2007/0208531 A1 | 9/2007 | Darley et al. |
| 2007/0247306 A1 | 10/2007 | Case |
| 2007/0250981 A1 | 11/2007 | Siebert |
| 2007/0287596 A1 | 12/2007 | Case et al. |
| 2008/0009275 A1 | 1/2008 | Werner et al. |
| 2008/0051993 A1 | 2/2008 | Graham et al. |
| 2008/0058971 A1 | 3/2008 | Graham et al. |
| 2008/0059064 A1 | 3/2008 | Werner et al. |
| 2008/0065319 A1 | 3/2008 | Graham et al. |
| 2008/0088303 A1 | 4/2008 | Englert |
| 2008/0096726 A1 | 4/2008 | Riley et al. |
| 2008/0103689 A1 | 5/2008 | Graham et al. |
| 2008/0125288 A1 | 5/2008 | Case |
| 2008/0274844 A1 | 11/2008 | Ward |
| 2008/0296984 A1 | 12/2008 | Honma et al. |
| 2008/0315829 A1 | 12/2008 | Jones et al. |
| 2008/0319661 A1 | 12/2008 | Werner et al. |
| 2009/0047645 A1 | 2/2009 | Dibenedetto et al. |
| 2009/0048044 A1 | 2/2009 | Oleson et al. |
| 2009/0048070 A1 | 2/2009 | Vincent et al. |
| 2009/0069702 A1 | 3/2009 | How et al. |
| 2009/0069722 A1 | 3/2009 | Flaction et al. |
| 2009/0210078 A1 | 8/2009 | Crowley |
| 2009/0233770 A1 | 9/2009 | Vincent et al. |
| 2009/0284377 A1 | 11/2009 | Tuttle et al. |
| 2009/0292178 A1 | 11/2009 | Ellis et al. |
| 2010/0042427 A1 | 2/2010 | Graham et al. |
| 2010/0088023 A1 | 4/2010 | Werner |
| 2010/0121599 A1 | 5/2010 | Boeve et al. |
| 2010/0184563 A1 | 7/2010 | Molyneux et al. |
| 2010/0184564 A1 | 7/2010 | Molyneux et al. |
| 2010/0185398 A1 | 7/2010 | Berns et al. |
| 2010/0201352 A1 | 8/2010 | Englert |
| 2010/0204615 A1 | 8/2010 | Kyle et al. |
| 2010/0292050 A1 | 11/2010 | DiBenedetto et al. |
| 2010/0292599 A1 | 11/2010 | Oleson et al. |
| 2010/0292600 A1 | 11/2010 | Dibenedetto et al. |
| 2011/0054270 A1 | 3/2011 | Derchak |
| 2011/0054271 A1 | 3/2011 | Derchak et al. |
| 2011/0054272 A1 | 3/2011 | Derchak |
| 2011/0054290 A1 | 3/2011 | Derchak |
| 2011/0082641 A1 | 4/2011 | Werner et al. |
| 2011/0087115 A1 | 4/2011 | Sackner et al. |
| 2011/0105861 A1 | 5/2011 | Derchak et al. |
| 2011/0119022 A1 | 5/2011 | Kuenzler et al. |
| 2011/0130643 A1 | 6/2011 | Derchak et al. |
| 2011/0131012 A1 | 6/2011 | Czaja et al. |
| 2012/0029299 A1 | 2/2012 | DeRemer et al. |
| 2012/0078127 A1 | 3/2012 | McDonald et al. |
| 2012/0083705 A1 | 4/2012 | Yuen et al. |
| 2012/0254934 A1 | 10/2012 | McBrearty et al. |
| 2013/0274635 A1 | 10/2013 | Coza et al. |
| 2013/0338472 A1 | 12/2013 | Macia Barber et al. |

FOREIGN PATENT DOCUMENTS

| | | |
|---|---|---|
| DE | 10040623 | 5/2001 |
| EP | 1134555 A1 | 9/2001 |
| EP | 2027817 | 2/2009 |
| JP | 07-96014 | 10/1995 |
| WO | WO 97/21983 | 6/1997 |
| WO | WO 2002/067449 A2 | 8/2002 |
| WO | WO 2007/082389 | 7/2007 |
| WO | WO 2012/014110 A2 | 2/2012 |

OTHER PUBLICATIONS

Shead, S., "Shirt Capable of Converting Body Heat into Electricity," The Engineer, http://www.theengineer.co.uk/electronics/news/shirt-capable-of-converting-body-heat-into-electricity/1010775.article, dated Nov. 3, 2011, accessed Mar. 1, 2013.

European Search Report for Application No. EP 13163555, European Patent Office, Munich, Germany, dated Sep. 20, 2013, 6 pages.

Office Action issued in Chinese Application No. 201310129427.7, dated Dec. 29, 2014.

Office Action issued in Chinese Application No. 201310128838.4, dated Feb. 2, 2015.

Concise explanation of Office Action issued in Chinese Application No. 201310129427.7, dated Dec. 29, 2014.

Concise explanation of Office Action issued in Chinese Application No. 201310128838.4, dated Feb. 2, 2015.

| Jump Height (Inches) | Launch Angle (Degrees) |
|---|---|
| 20 | 47 |
| 22 | 44 |
| 18 | 50 |
| 22 | 45 |
| 19 | 50 |
| 19 | 52 |
| 20 | 46 |

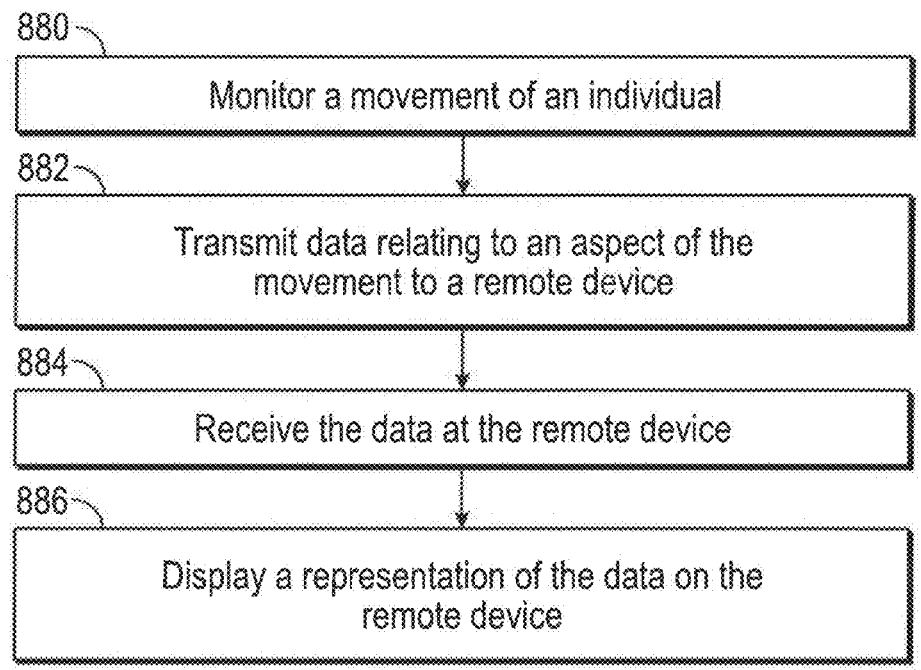
FIG. 30
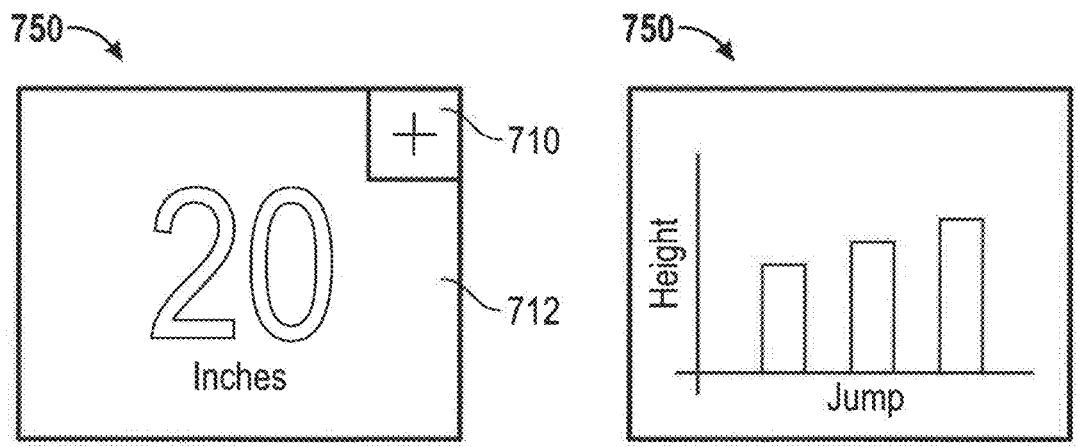
FIG. 31
FIG. 32

WEARABLE ATHLETIC ACTIVITY MONITORING SYSTEMS

CROSS-REFERENCE TO RELATED APPLICATIONS

This application is a continuation of U.S. patent application Ser. No. 13/797,274, filed Mar. 12, 2013, which is a continuation-in-part of U.S. patent application Ser. No. 13/446,986, filed Apr. 13, 2012, which issued as U.S. Pat. No. 9,504,414 on Nov. 29, 2016. U.S. patent application Ser. No. 13/446,986 is related to commonly-owned U.S. patent application Ser. No. 13/446,937, filed Apr. 13, 2012, and commonly owned U.S. patent application Ser. No. 13/446,982, filed Apr. 13, 2012, which issued as U.S. Pat. No. 9,257,054 on Feb. 9, 2016. Each of the applications listed in this paragraph is incorporated herein by reference in its entirety.

FIELD OF THE INVENTION

Embodiments of the present invention generally relate to wearable athletic activity monitoring methods and systems. More particularly, embodiments of the present invention relate to methods and systems for monitoring the movement of an individual engaged in an athletic activity during the athletic activity.

BACKGROUND OF THE INVENTION

Athletic activity is important to maintaining a healthy lifestyle and is a source of entertainment for many people. Some individuals prefer to engage in team athletic activities such as, for example, soccer or basketball, while other individuals prefer to engage in individual athletic activities such as, for example, running or skiing. Regardless of whether the activity is a team or individual activity, it is common for individuals to participate in both competitive sessions, such as a soccer match or a running race, and more informal training sessions such as conducting soccer drills or running interval sprints.

Technology has resulted in the development of fitness monitoring devices that are capable of recording information about an individual's performance during an athletic activity using sensors, and in some cases providing feedback about the individual's performance. Some portable fitness monitoring devices employ sensors attached to the individual's body, while other portable fitness monitoring devices rely on sensors attached to a piece of athletic equipment. Such sensors may be capable of measuring various physical and/or physiological parameters associated with the individual's physical activity.

Many existing fitness monitoring devices are not portable and thus are not suitable for monitoring in many real world competitive or training sessions. Even those that are portable are often too heavy or lack sufficient battery and/or processing power to be used for extended periods under rigorous competitive or training conditions. In addition, while some existing fitness monitoring devices are capable of making relatively simple performance determinations such as an individual's current heart rate or total step count for an activity, more advanced determinations are often not possible or suffer from accuracy issues. Finally, the performance feedback provided by existing devices to individuals often fails to provide these individuals with quick, accurate, insightful information that would enable them to easily compare past performances, develop strategies for improving future performances, visualize performances, or select new training regimens or athletic equipment.

BRIEF SUMMARY OF THE INVENTION

What is needed are new athletic activity monitoring methods and systems having improved capabilities, thus offering individuals engaged in athletic activities better tools to assess their activities. At least some of the embodiments of the present invention satisfy the above needs and provide further related advantages as will be made apparent by the description that follows.

Embodiments of the present invention relate to a sensor garment for monitoring an individual engaged in an athletic activity, the sensor garment including a garment formed of textile material, and a sensor module inseparably coupled to the textile material of the garment, wherein the sensor module comprises a single-purpose sensor configured to sense a single characteristic, wherein the sensor module comprises a radio antenna configured to transmit data generated by the single-purpose sensor, and wherein the sensor module comprises no external data port.

Additional embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention by way of example, and not by way of limitation, and, together with the description, further serve to explain the principles of the invention and to enable a person skilled in the pertinent art to make and use the invention.

FIG. 30 is a flow chart illustrating operations to display a representation of data relating to an aspect of a movement of an individual.

FIG. 31 is an illustration of a display according to an embodiment of the present invention.

FIG. 32 is an illustration of a display according to an embodiment of the present invention.

DETAILED DESCRIPTION

Figure 1:
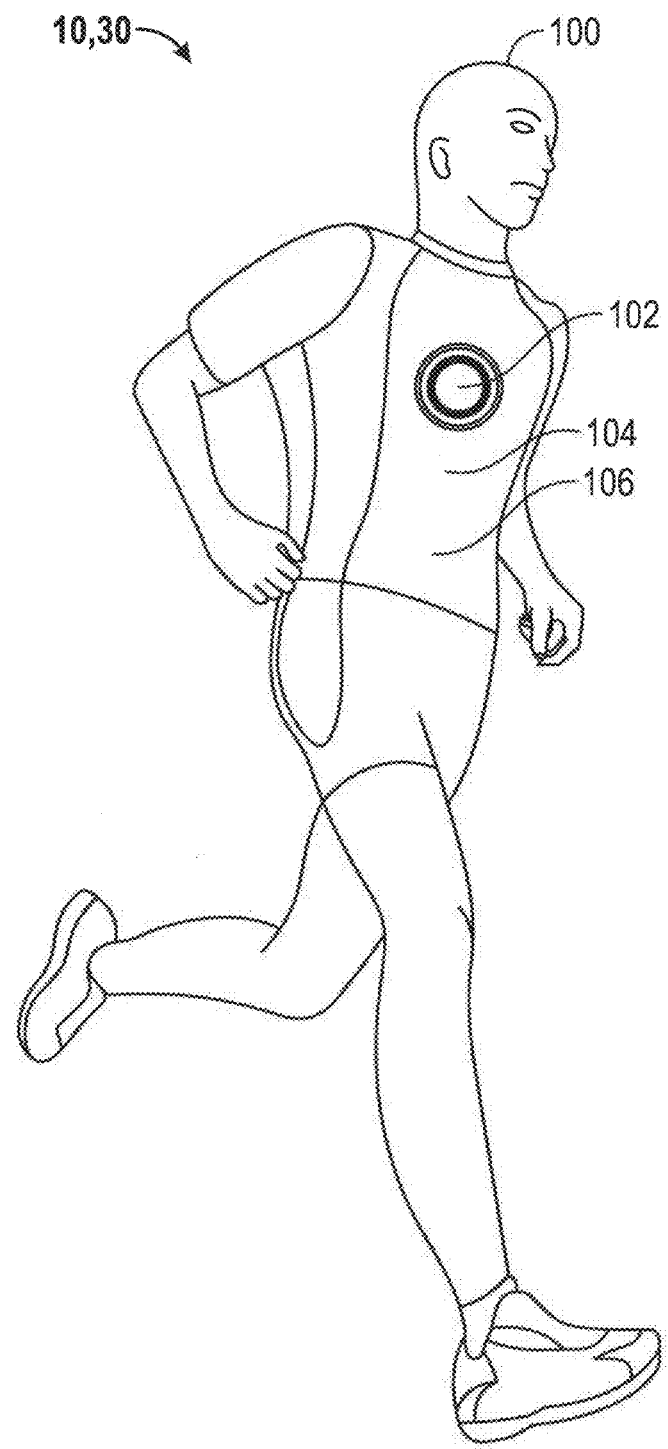
FIG. 1 is an illustration of an individual using an athletic activity monitoring system according to an embodiment of the present invention.

The present invention will now be described in detail with reference to embodiments thereof as illustrated in the accompanying drawings. References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, tangible computer readable or computer usable storage media having instructions stored thereon, or a combination thereof, and may be implemented in one or more computer systems or other processing systems.

The present invention generally relates to athletic activity monitoring methods and systems. More particularly, the present invention relates to methods and systems for monitoring the movement of the body of an individual engaged in an athletic activity. An individual engaged in an athletic activity (or another interested person such as a coach, teammate, or spectator) may desire to obtain information about the motion of the individual's body or the motion of a piece of the individual's athletic equipment during the course of the athletic activity.

For example, if the individual is participating in an activity that involves the use of a sport ball, such as playing in a soccer (i.e., football) match, it may be desirable, for example, to be able to determine the various launch angles at which the soccer ball (i.e., football) was kicked by the individual, to be able to determine the rate of rotation of the soccer ball after it was kicked by the individual, or to be able to determine the peak speeds that the soccer ball was traveling at after being kicked by the individual.

As a further example, if the individual is participating in an activity that involves various movements the individual's chest, such practicing basketball skills, it may be desirable, for example, to be able to identify instances when the individual cut to the left or cut to the right when trying to dribble around a defender, to be able to determine the height that the individual jumped and/or the force with which the individual jumped when taking jump shots, attempting dunks, or attempting to block shots, or to be able to determine the individual's reaction time when working on basketball-related reaction time drills.

In an embodiment, the movement of the bodies of a plurality of individuals engaged in an athletic activity (e.g., teammates or opponents in a team sport) and/or the movement of a plurality of pieces of athletic equipment used by the individuals during the athletic activity may be monitored. In some embodiments, real-time monitoring and/or feedback may be provided, while in other embodiments post-activity feedback may be provided By using an athletic activity monitoring system including one or more portable sensors, embodiments of the present invention described below may advantageously enable an individual (or their coach, teammate, or a spectator) to obtain this or other information about the motion of the individual's body or the motion of a piece of the individual's athletic equipment during the course of the athletic activity. Data obtained by sensors may be processed in a variety of ways to yield useful information about the motion of an object of interest during the activity. In some embodiments, sensor data may be processed to monitor changes in the spatial orientation (i.e., changes in the position and/or rotation, relative to a specific location on the Earth or other point of reference) of the individual's body or a piece of the individual's athletic equipment. In other embodiment, sensor data may be processed to by reference to a predetermined correlation between movement data and an activity metric stored in a data structure.

In one embodiment, information about the motion of the individual's body or the motion of a piece of the individual's athletic equipment may be used, for example, to provide coaching to the individual about how their movements could be improved, or as a check on the accuracy of a referee, umpire, or other athletic competition judge's judgment related to the movement of the individual's body or athletic equipment.

FIG. 1 is an illustration of an individual 100 using an athletic activity monitoring system 10 according to an embodiment of the present invention. The individual 100 may desire to obtain information about the motion of the individual's 100 body or the motion of a piece of the individual's 100 athletic equipment during the course of the athletic activity using athletic activity monitoring systems 10 according to the present invention.

Athletic activity monitoring systems 10 according to embodiments of the present invention may be suitable for use by individuals 100 for team or individual athletic activities and for competitive and informal training sessions. For example, athletic activity monitoring systems 10 according to embodiments of the present invention may be suitable for use by individuals 100 engaged in athletic activities such as baseball, basketball, bowling, boxing, cricket, cycling, football (i.e., American football), golf, hockey, lacrosse, rowing, rugby, running, skateboarding, skiing, soccer (i.e., football), surfing, swimming, table tennis, tennis, or volleyball, or during training sessions related thereto.

Athletic activity monitoring systems 10 according to embodiments of the present invention may include a sensor module 102. The sensor module 102 may include one or more sensors, and may be physically coupled to an object 104 during an athletic activity conducted by an individual 100. As explained in further detail below, the sensor module 102 may be used to monitor changes in the spatial orientation of the individual's 100 body 106 or a piece of the individual's athletic equipment 108 in some embodiments, while the sensor module 102 may be used in combination with predetermined correlation data stored in a data structure to determine a correlation between body 106 or equipment 108 movement data and an activity metric in other embodiments.

In one embodiment, as illustrated in FIG. 1, the monitored object 104 may be the individual's 100 body 106, and the sensor module 102 may be physically coupled to the individual's 100 body 106. In the illustrated embodiment, the sensor module 102 is configured to be physically coupled to the portion of the individual's 100 body 106 known as the chest. In other embodiments, the sensor module 102 may be configured to be physically coupled to other portions of the individual's 100 body 106 such as, for example, the individual's head, neck, shoulder, back, arm, wrist, hand, finger, waist, hip, leg, ankle, foot, or toe.

In some embodiments, the sensor module 102 may be configured to be physically coupled to the portion of the individual's 100 body 106 with one or more layers of clothing, an article of footwear, or athletic protective equipment existing between the sensor module 102 and the individual's 100 body 106. Regardless of whether intervening articles are present, the sensor module 102 may be physically coupled to the portion of the individual's 100 body 106 by a variety of releasable or non-releasable coupling means such as, for example, straps, adhesives, pockets, clips, or by being integrated into an article of clothing (e.g., shirt, pants, sock, glove, or hat), footwear, or athletic protective equipment worn by the individual 100.

In one embodiment, the sensor module 102 may be configured to be placed in a sensor module 102 retention element of a garment that is configured to retain the sensor module 102. In some exemplary embodiments, retention element may be sized and shaped to correspond to the size and shape of the sensor module 102, to be capable of nesting sensor module 102 therein and holding the sensor module 102 in place so as to minimize the effect of movement of a wearer of the garment on the sensor module 102. Additional elements may be used to help minimize this effect, such as, for example, bands and spacer elements. The sensor module 102 retention element may be coupled to textile a layer of a garment by, for example, being integral therewith, being adhered, stitched, welded, tied, clipped, snapped, or mounted thereto, or any combination of these and other techniques. In some exemplary embodiments, sensor module 102 retention element is formed integrally with a textile layer of the garment.

In some embodiments, the sensor module 102 retention element may be positioned to correspond to the upper back of a wearer of the sensor module 102. The sensor module 102 retention element to correspond to a high position on the wearer, such as the upper back, may help minimize interference and maximize range and signal strength of the sensor module 102 within the sensor module 102 retention element when the sensor module 102 sends or receives data. Additionally, positioning the sensor module 102 retention element to correspond to the upper back minimizes interference with athlete movements by the sensor module 102. In some exemplary embodiments, sensor module 102 retention element is positioned to correspond to other than the upper back of a wearer.

Figure 2:
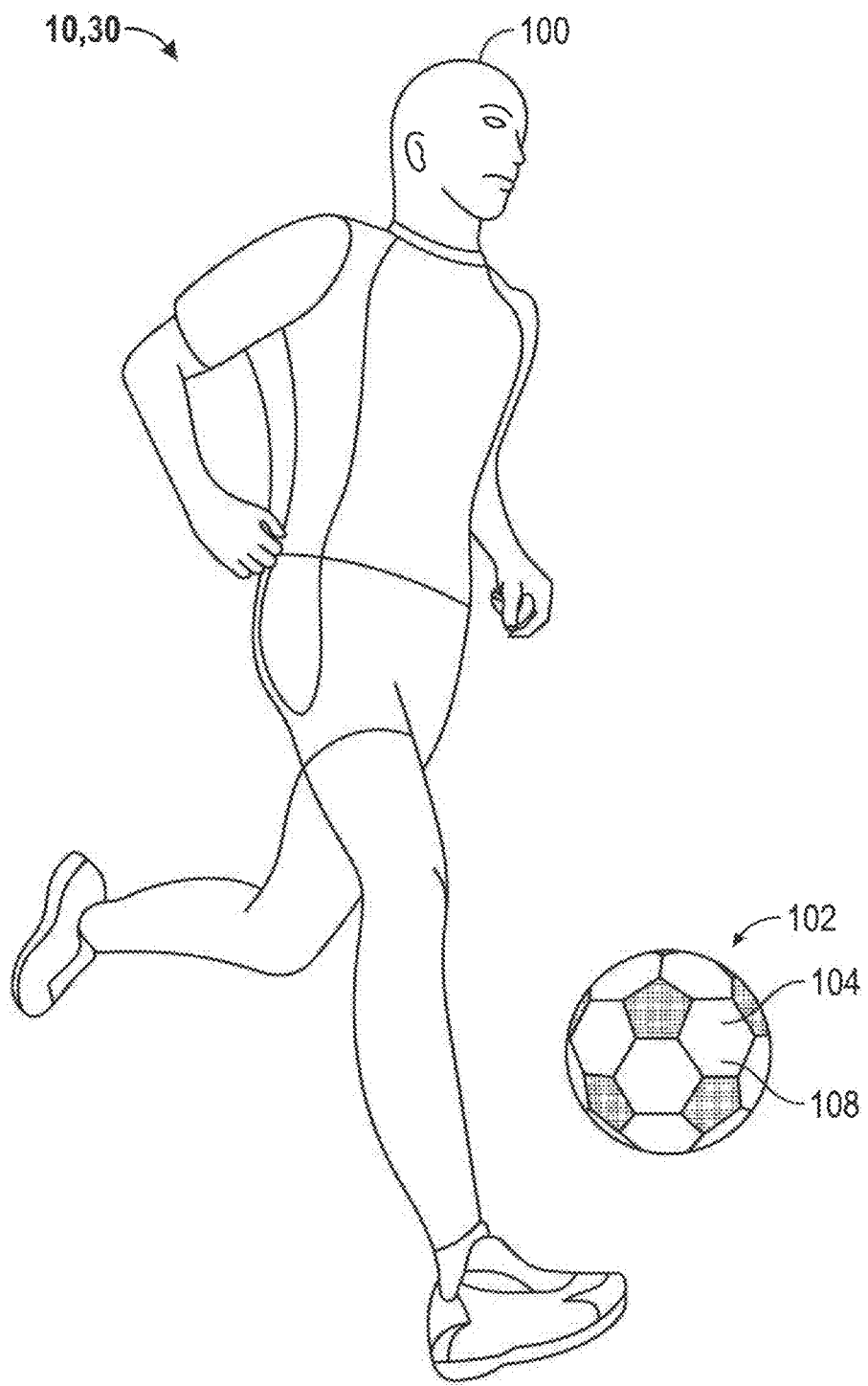
FIG. 2 is an illustration of an individual using an athletic activity monitoring system according to an embodiment of the present invention.

In another embodiment, as illustrated in FIG. 2, the object 104 may be a piece of athletic equipment 108 used by the individual 100 during the athletic activity, and the sensor module 102 may be physically coupled to the piece of athletic equipment 108. In the illustrated embodiment, the sensor module 102 is physically coupled to a piece of athletic equipment 108 that is a soccer ball. In other embodiments, the sensor module 102 may be configured to be physically coupled to other pieces of athletic equipment 108 such as, for example, any type of sport ball, any type of sport "stick" (e.g., a baseball bat, hockey stick, golf club, table tennis paddle, or tennis racquet), a sport glove, a bicycle, an oar, a shoe, a boot, a ski, a hat or cap, a skateboard, a surfboard, or a pair of glasses or goggles.

The sensor module 102 may be physically coupled to the piece of athletic equipment 108 by a variety of coupling means depending on the nature of the piece of athletic equipment 108 and the athletic activity. For example, the sensor module 102 may be physically coupled to a sport ball by being attached to the exterior of the ball, by being attached to an interior surface of a hollow ball, by being suspended by a suspension system in the interior of a hollow ball, or by being integrated into the outer layer or other layer of a multi-layer ball. Also, the sensor module 102 may be physically coupled to a non-hollow sport ball (e.g., a baseball, bowling ball, or golf ball) by, for example, being attached to the exterior of the ball, being integrated between layers of a multi-layer ball, by being embedded in a solid portion of the ball. As further examples, the sensor module 102 may be releasably or non-releasably physically coupled to a sport "stick" by being wrapped around a portion of the sport stick, by being clipped to a portion of the sport stick, by being attached to an exterior surface of the sport stick, by being attached to an interior surface of a hollow or non-hollow sport stick, by being suspended by a suspension system in the interior of a hollow sport stick, or by being integrated into the wall or other layer of a multi-layer or composite sport stick. The sensor module 102 may be physically coupled to the piece of athletic equipment 108 by a variety of coupling means such as, for example, straps, adhesives, or by being integrated into the piece of athletic equipment 108.

In other embodiments, the sensor module 102 may be integrated within an existing piece of athletic activity monitoring equipment such as, for example, a heart rate monitoring device, a pedometer, and accelerometer-based monitoring device, or other portable fitness monitoring device such as, for example, devices sold by adidas AG of Herzogenaurach, Germany under the MICOACH, PACER, ZONE, or SPEED CELL brand names.

Figure 3:
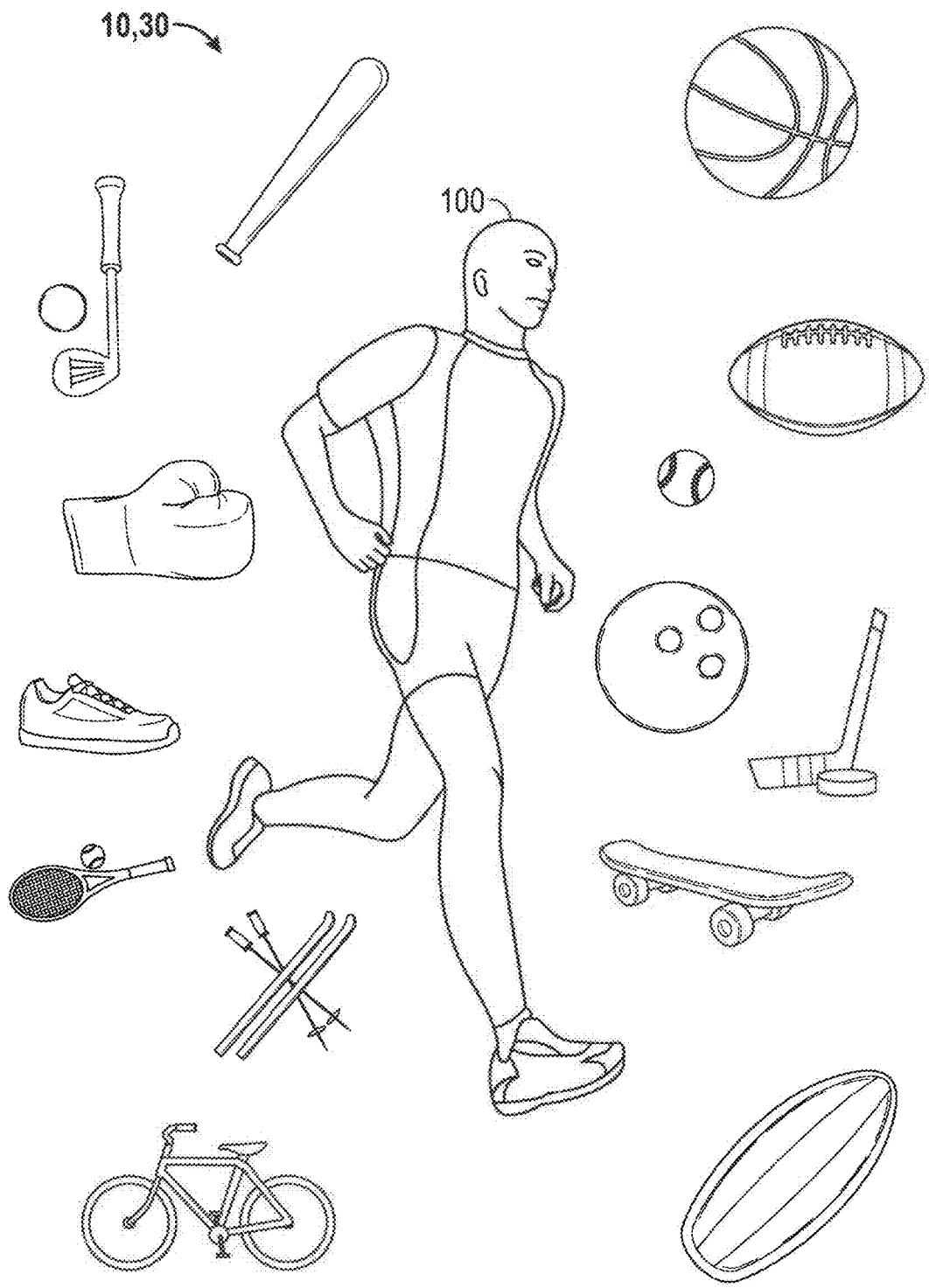
FIG. 3 is an illustration of various different pieces of athletic equipment according to embodiments of the present invention.

FIG. 3 is an illustration of various different pieces of athletic equipment 108 that could be used according to embodiments of the monitoring system 10 of the present invention. As illustrated, the monitoring system 10 of the present invention may be used with a variety of different pieces of athletic equipment 108, such as, for example, a basketball, a football, a baseball bat, a baseball, a bowling ball, a hockey stick, a hockey puck, a skateboard, a surfboard, a bicycle, a pair of skis, ski poles, a tennis racquet, a tennis ball, an article of footwear, a boxing glove, a golf club, or a golf ball.

Figure 4:
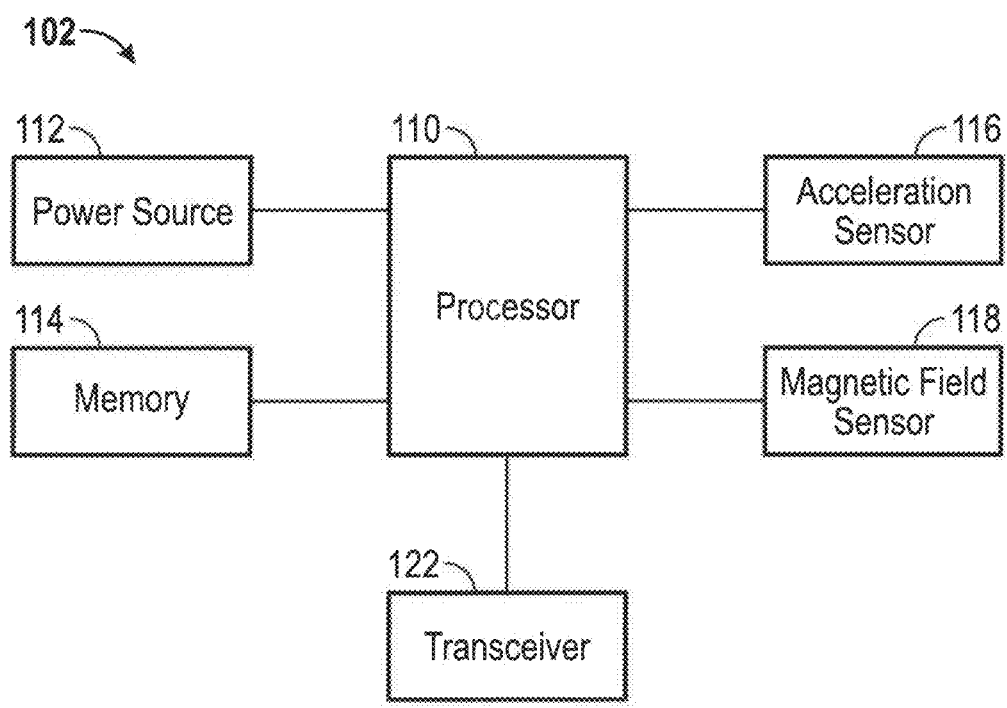
FIG. 4 is a block diagram of components of a sensor module according to an embodiment of the present invention.

FIG. 4 is a block diagram of components of a sensor module 102 according to an embodiment of the present invention. In the illustrated embodiment, the sensor module 102 includes a processor 110, a power source 112, a memory 114, an acceleration sensor 116, a magnetic field sensor 118, and a transceiver 122 operatively connected to one another to carry out the functionality of the sensor module 102. In other embodiments, one or more of these sensor module 102 components may be omitted, or one or more additional components may be added.

The processor 110 may be adapted to implement application programs stored in the memory 114 of the sensor module 102. The processor 110 may also be capable of implementing analog or digital signal processing algorithms such as raw data reduction and filtering. For example, processor 110 may be configured to receive raw data from sensors and process such data at the sensor module 102. The processor 110 is operatively connected to the power source 112, the memory 114, the acceleration sensor 116, the magnetic field sensor 118, and the transceiver 122.

The power source 112 may be adapted to provide power to the sensor module 102. In one embodiment, the power source 112 may be a battery. The power source may be built into the sensor module 102 or removable from the sensor module 102, and may be rechargeable or non-rechargeable. In an embodiment, the power source 112 may be recharged by being plugged into a cable attached to a charging source, such as a universal serial bus ("USB") cable attached to a personal computer. In another embodiment, the power source 112 may be recharged by inductive charging, wherein an electromagnetic field is used to transfer energy from an inductive charger to the power source 112 when the two are brought in close proximity, but need not be plugged into one another via a cable. In some embodiment, a docking station may be used to facilitate charging.

The memory 114 may be adapted to store application program instructions and to store athletic activity data. In an embodiment, the memory 114 may store application programs used to implement aspects of the functionality of the athletic activity monitoring system 10 described herein. In one embodiment, the memory 114 may store raw data, recorded data, and/or calculated data. In some embodiments, as explained in further detail below, the memory 114 may act as a data storage buffer. The memory 114 may include both read only memory and random access memory, and may further include memory cards or other removable storage devices.

In some embodiments of the present invention, the memory 114 may store raw data, recorded data, and/or calculated data permanently, while in other embodiments the memory 114 may only store all or some data temporarily, such as in a buffer. In one embodiment of the present invention, the memory 114, and/or a buffer related thereto, may store data in memory locations of predetermined size such that only a certain quantity of data may be saved for a particular application of the present invention.

The acceleration sensor 116 may be adapted to measure the acceleration of the sensor module 102. Accordingly, when the sensor module 102 is physically coupled to an object 104 (such as an individual's 100 body 106 or a piece of athletic equipment 108), the acceleration sensor 116 may be capable of measuring the acceleration of the object 104, including the acceleration due to the earth's gravitational field. In one embodiment, the acceleration sensor 116 may include a tri-axial accelerometer that is capable of measuring acceleration in three orthogonal directions. In other embodiments one, two, three, or more separate accelerometers may be used. In some embodiments, the accelerometer may be a low-mass accelerometer.

The magnetic field sensor 118 may be adapted to measure the strength and direction of magnetic fields in the vicinity of the sensor module 102. Accordingly, when the sensor module 102 is physically coupled to an object 104 (such as an individual's 100 body 106 or a piece of athletic equipment 108), the magnetic field sensor 118 may be capable of measuring the strength and direction of magnetic fields in the vicinity of the object 104, including the earth's magnetic field. In one embodiment, the magnetic field sensor 118 may be a vector magnetometer. In other embodiments, the magnetic field sensor 118 may be a tri-axial magnetometer that is capable of measuring the magnitude and direction of a resultant magnetic vector for the total local magnetic field in three dimensions. In other embodiments one, two, three, or more separate magnetometers may be used.

In one embodiment of the present invention, the acceleration sensor 116 and the magnetic field sensor 118 may be contained within a single accelerometer-magnetometer module bearing model number LSM303DLHC made by STMicroelectronics of Geneva, Switzerland. In other embodiments, the sensor module 102 may include only one of the acceleration sensor 116 and the magnetic field sensor 118, and may omit the other if desired.

The transceiver 122 depicted in FIG. 4 may enable the sensor module 102 to wirelessly communicate with other components of the athletic activity monitoring system 10, such as those described in further detail below. In one embodiment, the sensor module 102 and the other local components of the athletic activity monitoring system 10 may communicate over a personal area network or local area network using, for example, one or more of the following protocols: ANT, ANT+ by Dynastream Innovations, Bluetooth, Bluetooth Low Energy Technology, BlueRobin, or suitable wireless personal or local area network protocols. Other known communication protocols suitable for an athletic activity monitoring system 10 may also be used.

In one embodiment, the transceiver 122 is a low-power transceiver. In some embodiments, the transceiver 122 may be a two-way communication transceiver 122, while in other embodiments the transceiver 122 may be a one-way transmitter or a one-way receiver. Wireless communication between the sensor module 102 and other components of the athletic activity monitoring system 10 is described in further detail below. In other embodiments, the sensor module 102 may be in wired communication with other components of the athletic activity monitoring system 10 that does not rely on transceiver 122.

In some embodiments of the present invention, a sensor module 102 having components such as those depicted in FIG. 4 may be physically coupled to an object 104 during an athletic activity conducted by an individual 100 to monitor changes in the spatial orientation of the individual's 100 body 106 or a piece of the individual's athletic equipment 108, or to determine a correlation between body 106 or equipment 108 movement data and an activity metric. In these embodiments, the acceleration sensor 116 and the magnetic field sensor 118 may be responsible for collecting the data necessary to carry out the various monitoring calculations.

In some other embodiments, however, it may be desirable to have additional sensors included within the sensor module 102, or to have additional sensors in communication with the sensor module 102. In further embodiments, the sensor module 102 may be integrated within an existing piece of athletic activity monitoring equipment possibly having additional or different sensors such as, for example, a heart rate monitoring device, a pedometer, and accelerometer-based monitoring device, or other portable fitness monitoring device such as, for example, devices sold by adidas AG of Herzogenaurach, Germany under the MICOACH, PACER, ZONE, or SPEED CELL brand names.

In addition to the acceleration sensor 116 and the magnetic field sensor 118, other sensors that may be part of the sensor module 102 or separate from but in communication with the sensor module 102 may include sensors capable of measuring a variety of athletic performance parameters. The term "performance parameters" may include physical parameters and/or physiological parameters associated with the individual's 100 athletic activity. Physical parameters measured may include, but are not limited to, time, distance, speed, pace, pedal count, wheel rotation count, rotation generally, stride count, stride length, airtime, stride rate, altitude, strain, impact force, jump force, force generally, and jump height. Physiological parameters measured may include, but are not limited to, heart rate, respiration rate, blood oxygen level, blood lactate level, blood flow, hydration level, calories burned, or body temperature.

Actual sensors that may be capable of measuring these parameters may include, but are not limited to, a pedometer, a pulsimeter, a thermometer, an altimeter, a pressure sensor, a strain gage, a bicycle power meter, a bicycle crank or wheel position sensor, a magnetic sensor, an angular momentum sensor (e.g., a gyroscope), a resistance sensor, or a force sensor.

Figure 5:
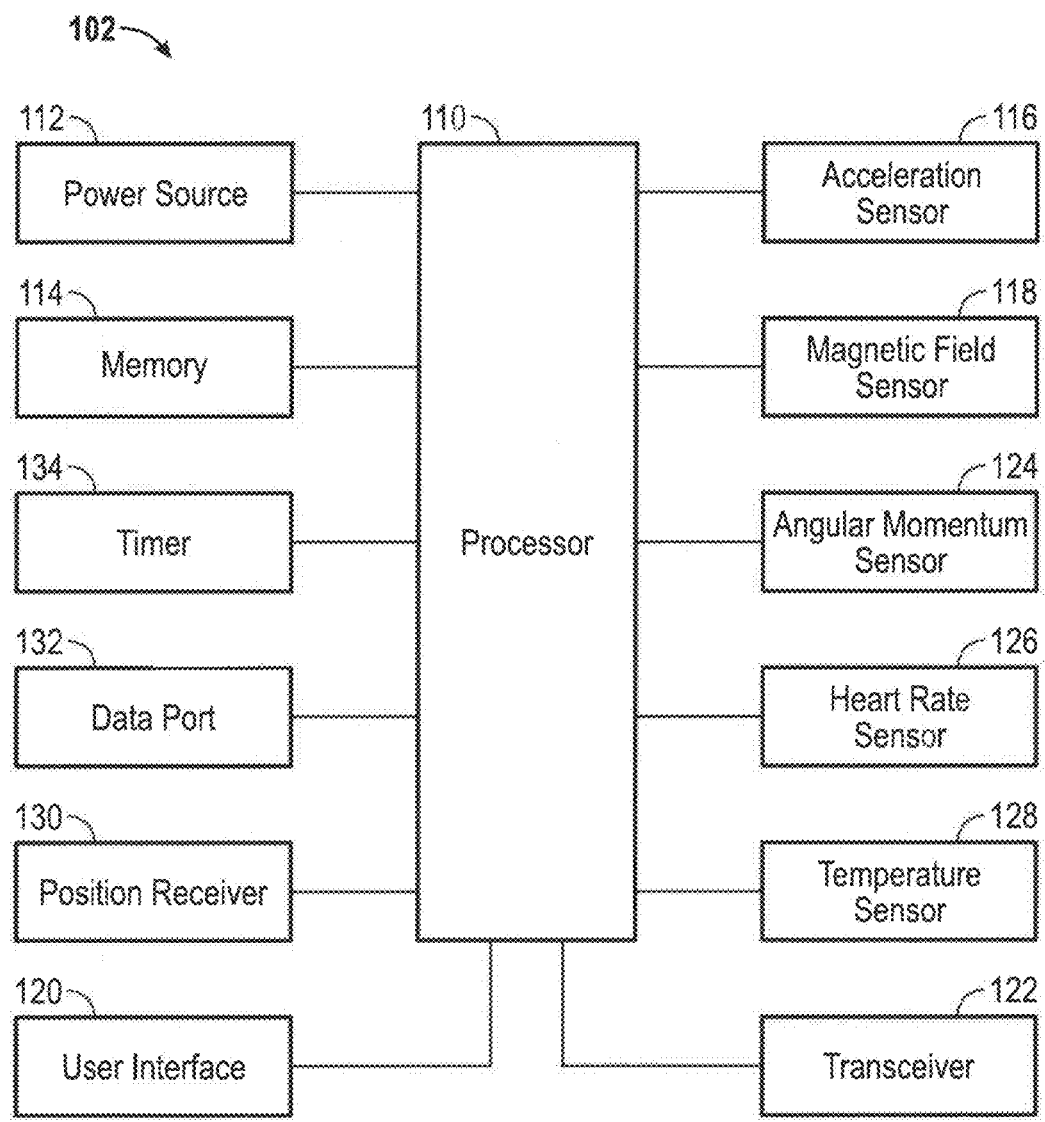
FIG. 5 is a block diagram of components of a sensor module according to an embodiment of the present invention.

FIG. 5 is a block diagram of components of a sensor module 102 according to another embodiment of the present invention that may incorporate some of the additional sensors mentioned above, as well as other additional components. In the illustrated embodiment, the sensor module 102 includes a processor 110, a power source 112, a memory 114, an acceleration sensor 116, a magnetic field sensor 118, a user interface 120, and a transceiver 122, an angular momentum sensor 124, a heart rate sensor 126, a temperature sensor 128, a position receiver 130, a data port 132, and a timer 134 operatively connected to one another to carry out the functionality of the sensor module 102. In other embodiments, one or more of these sensor module 102 components may be omitted, or one or more additional components may be added.

The processor 110, the power source 112, the memory 114, the acceleration sensor 116, the magnetic field sensor 118, and the transceiver 122 of the embodiment of FIG. 5 may have structures and functions similar to those described above with respect to analogous components in FIG. 4.

The user interface 120 of the sensor module 102 may be used by the individual 100 to interact with the sensor module 102. In an embodiment, the user interface 120 may include one or more input buttons, switches, or keys, including virtual buttons, switches, or keys of a graphical user interface touch screen surface. The function of each of these buttons, switches, or keys may be determined based on an operating mode of the sensor module 102. In one embodiment, the user interface 120 may include a touch pad, scroll pad and/or touch screen. In another embodiment, the user interface 120 may include capacitance switches. In a further embodiment, the user interface 120 may include voice-activated controls.

In some embodiments, however, the sensor module 102 may not include a user interface 120. In these embodiments, the sensor module 102 may be capable of communicating with other components of the athletic activity monitoring system 10 which may themselves include user interfaces.

The angular momentum sensor 124, which may be, for example, a gyroscope, may be adapted to measure the angular momentum or orientation of the sensor module 102. Accordingly, when the sensor module 102 is physically coupled to an object 104 (such as an individual's 100 body 106 or athletic equipment 108), the angular momentum sensor 124 may be capable of measuring the angular momentum or orientation of the object 104. In one embodiment, the angular momentum sensor 124 may be a tri-axial gyroscope that is capable of measuring angular rotation about three orthogonal axis. In other embodiments one, two, three, or more separate gyroscopes may be used. In an embodiment, the angular momentum sensor 124 may be used to calibrate measurements made by one or more of the acceleration sensor 116 and the magnetic field sensor 118.

The heart rate sensor 125 may be adapted to measure an individual's heart rate. The heart rate sensor 125 may be placed in contact with the individual's 100 skin, such as the skin of the individual's chest, and secured with a strap. The heart rate sensor 125 may be capable of reading the electrical activity the individual's 100 heart.

The temperature sensor 128 may be, for example, a thermometer, a thermistor, or a thermocouple that measures changes in the temperature. In some embodiments, the temperature sensor 128 may primarily be used for calibration other sensors of the athletic activity monitoring system 10, such as, for example, the acceleration sensor 116 and the magnetic field sensor 118.

In one embodiment, the position receiver 130 may be an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In another embodiment, the position receiver 130 may be an antennae that is capable of communicating with local or remote base stations or radio transmission transceivers such that the location of the sensor module 102 may be determined using radio signal triangulation or other similar principles. In some embodiments, position receiver 130 data may allow the sensor module 102 to detect information that may be used to measure and/or calculate position waypoints, time, location, distance traveled, speed, pace, or altitude.

The data port 132 may facilitate information transfer to and from the sensor module 102 and may be, for example, a USB port. In some exemplary embodiments, data port 132 can additionally or alternatively facilitate power transfer to power source 112, in order to charge power source 112.

The timer 134 may be a clock that is capable of tracking absolute time and/or determining elapsed time. In some embodiments, the timer 134 may be used to timestamp certain data records, such that the time that certain data was measured or recorded may be determined and various timestamps of various pieces of data may be correlated with one another.

In some embodiments of the present invention, a sensor module 102 having components such as those depicted in FIG. 5 may be physically coupled to an object 104 during an athletic activity conducted by an individual 100 to monitor changes in the spatial orientation of the individual's 100 body 106 or a piece of the individual's athletic equipment 108, or to determine a correlation between body 106 or equipment 108 movement data and an activity metric. In these embodiments, the acceleration sensor 116, the magnetic field sensor 118, and/or other included sensors may be responsible for collecting the data necessary to carry out the various monitoring calculations. In some other embodiments, however, it may be desirable to have additional sensors included within the sensor module 102, to have additional sensors in communication with the sensor module 102, or to have fewer sensors with the sensor module 102.

Figure 6A:
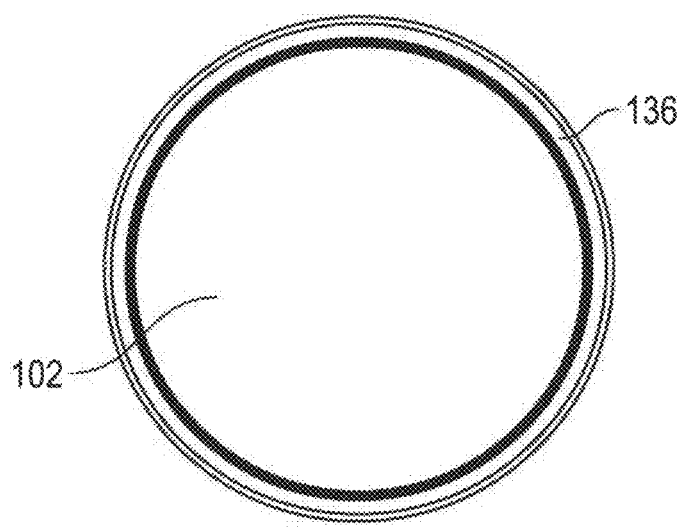
FIG. 6A is an illustration of a sensor module configured for monitoring an individual's body according to an embodiment of the present invention.

FIG. 6A is an illustration of a sensor module 102 configured for monitoring an individual's 100 body 106 according to an embodiment of the present invention. The illustrated sensor module 102 may be similar to the sensor module 102 illustrated in FIG. 1 as being configured to be physically coupled to the portion of the individual's 100 body 106 known as the chest. In some embodiments of the present invention, the sensor module 102 of FIG. 6A may be physically coupled to an individual's 100 body 106 during an athletic activity to monitor changes in the spatial orientation of the individual's 100 body 106, or to determine a correlation between body 106 movement data and an activity metric.

As illustrated in FIG. 6A, in one embodiment, the sensor module 102 may include a housing 136. The housing 136 may contain and protect the various electronic components of the exemplary sensor modules 102 described above with reference to FIG. 4 or FIG. 5. Though the housing 136 is illustrated as a circular disc-shaped housing in FIG. 6A, the housing may take on any suitable size and shape that is able to accommodate the necessary components of the sensor module 102 and to physically couple to the desired part of the individual's 100 body 106. In one embodiment, the housing may be made of plastic, such as, for example, TPU, or other suitably durable material.

In some embodiments, the sensor module 102 may also include a button and/or a display. The button may serve as the user interface of the sensor module 102. The button may be capable of turning the sensor module 102 on and off, toggling through various display options, or serving a variety of other functions. Alternatively, multiple buttons or no buttons may be provided. In one embodiment, the display may be a relatively simple LED display that is capable of conveying the status or battery life of the sensor module 102 to an individual 100. In another embodiment, the display may be a more advanced display that is capable of displaying performance parameter information, feedback, or other information to the individual 100, such as a seven-segment LCD display. Alternatively, no button or display may be provided, as illustrated in FIG. 6A.

Figure 6B:
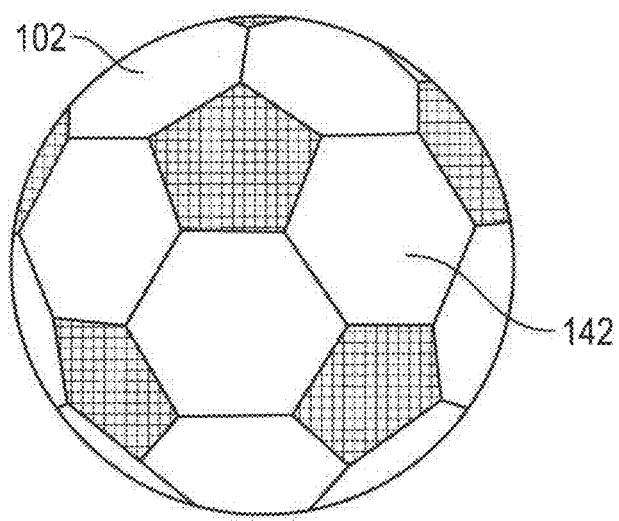
FIG. 6B is an illustration of a sport ball comprising a sensor module for monitoring the sport ball according to an embodiment of the present invention.

FIG. 6B is an illustration of a sport ball comprising a sensor module 102 for monitoring the sport ball according to an embodiment of the present invention. The illustrated sensor module 102 may be similar to the sensor module 102 illustrated in FIG. 2 as being configured to be physically coupled to a piece of athletic equipment 108 that is a soccer ball. In some embodiments of the present invention, the sensor module 102 of FIG. 6B that is incorporated in the soccer ball may be used during an athletic activity to monitor changes in the spatial orientation of the soccer ball, or to determine a correlation between ball movement data and an activity metric, as a result of, for example the individual 100 kicking the soccer ball.

As illustrated in FIG. 6B, the ball may include an outer layer 142 enclosing a hollow void of the ball. The outer layer 142 may be stitched, bonded, and/or glued together from panels of leather or plastic and laced to allow access to an internal air bladder, if necessary. In other embodiments, the ball may be a non-hollow sport ball (e.g., a baseball, bowling ball, or golf ball) including a single, solid layer or multiple different layers. In some embodiments, the sensor module 102 may be attached to or incorporated into the ball prior to sale to an individual, while in other embodiments the individual may later insert the sensor module 102 after purchasing the ball. In some embodiments, the ball may include a button and a display that may be similar to those described above with respect to the body-mounted sensor module 102, if present. Alternatively, no button or display may be provided, as illustrated in FIG. 6B.

In some embodiments of the present invention, the sensor module 102 may communicate with other components of the athletic activity monitoring system 10 via wired or wireless technologies. Communication between the sensor module 102 and other components of the athletic activity monitoring system 10 may be desirable for a variety of reasons. For example, to the extent that the sensor module 102 records and stores athletic activity information, it may be useful to transmit this information to another electronic device for additional data processing, data visualization, sharing with others, comparison to previously recorded athletic activity information, or a variety of other purposes. As a further example, to the extent that the sensor module 102 has insufficient processing power, wide area network transmission capabilities, sensor capabilities, or other capabilities, these capabilities can be provided by other components of the athletic activity monitoring system 10. With this in mind, possible communications means are described briefly below.

Wired communication between the sensor module 102 and a personal computer 204 may be achieved, for example, by placing the sensor module 102 in a docking unit that is attached to the personal computer 204 using a communications wire plugged into a communications port of the personal computer 204. In another embodiment, wired communication between the sensor module 102 and the personal computer 204 may be achieved, for example, by connecting a cable between the sensor module 102 and the computer 204. The data port 132 of the sensor module 102 and a communications port of the computer 204 may include USB ports. The cable connecting the sensor module 102 and the computer 204 may be a USB cable with suitable USB plugs including, but not limited to, USB-A or USB-B regular, mini, or micro plugs, or other suitable cable such as, for example, a FireWire, Ethernet or Thunderbolt cable. As previously explained above, in some embodiments, such cables could be used to facilitate power transfer to a power source 112 of the sensor module 102, in order to charge the power source 112. Alternatively, the power source 112 may be recharged by inductive charging, or by using a docking station.

Wired connection to a personal computer 204 may be useful, for example, to upload athletic activity information from the sensor module 102 to the personal computer 204, or to download application software updates or settings from the personal computer 204 to the sensor module 102.

Wireless communication between the sensor module 102 and the personal computer 204 may be achieved, for example, by way of a wireless wide area network (such as, for example, the Internet), a wireless local area network, or a wireless personal area network. As is well known to those skilled in the art, there are a number of known standard and proprietary protocols that are suitable for implementing wireless area networks (e.g., TCP/IP, IEEE 802.16, Bluetooth, Bluetooth low energy, ANT, ANT+ by Dynastream Innovations, or BlueRobin). Accordingly, embodiments of the present invention are not limited to using any particular protocol to communicate between the sensor module 102 and the various elements of the athletic activity monitoring system 10 of the present invention.

In one embodiment, the sensor module 102 may communicate with a wireless wide area network communications system such as that employed by mobile telephones. For example, a wireless wide area network communication system may include a plurality of geographically distributed communication towers and base station systems. Communication towers may include one or more antennae supporting long-range two-way radio frequency communication wireless devices, such as sensor module 102. The radio frequency communication between antennae and the sensor module 102 may utilize radio frequency signals conforming to any known or future developed wireless protocol, for example, CDMA, GSM, EDGE, 3G, 4G, IEEE 802.x (e.g., IEEE 802.16 (WiMAX)), etc. The information transmitted over-the-air by the base station systems and the cellular communication towers to the sensor module 102 may be further transmitted to or received from one or more additional circuit-switched or packet-switched communication networks, including, for example, the Internet.

Figure 7:
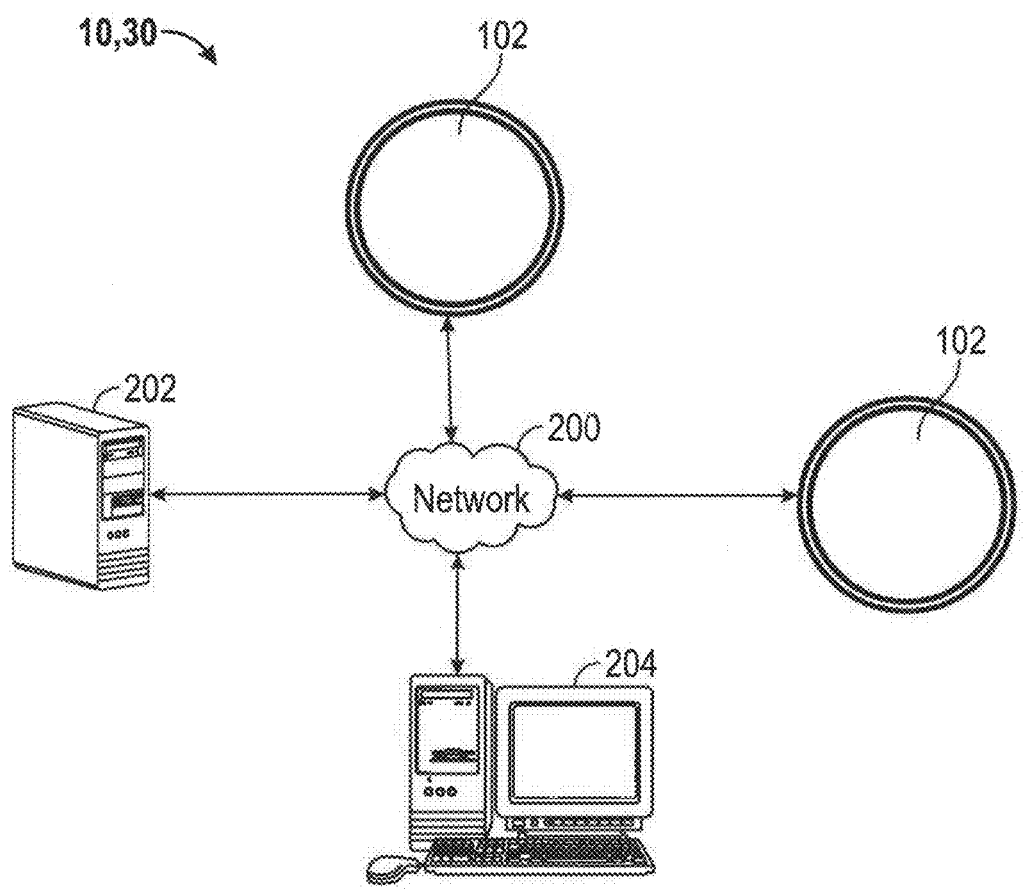
FIG. 7 is an illustration of various components of an athletic activity monitoring system communicating according to an embodiment of the present invention.

As shown in FIG. 7, communication may also occur between the sensor module 102, a personal computer 204, and/or a remote server 202 via a network 200. In an embodiment, the network 200 is the Internet. The Internet is a worldwide collection of servers, routers, switches and transmission lines that employ the Internet Protocol (TCP/IP) to communicate data. The network 200 may also be employed for communication between any two or more of the sensor module 102, the personal computer 204, the server 202, and a docking unit. In an embodiment of the present invention, information is directly communicated between the sensor module 102 and the server 202 via the network 200, thus bypassing the personal computer 204.

A variety of information may be communicated between any of the sensor module 102, the personal computer 204, the network 200, the server 202, or other electronic components such as, for example, another sensor module 102, a mobile phone, a tablet computer, or other portable electronic devices. Such information may include, for example, performance parameter data, device settings (including sensor module 102 settings), software, and firmware.

Communication among the various elements of the present invention may occur after the athletic activity has been completed or in real-time during the athletic activity. In addition, the interaction between, for example, the sensor module 102 and the personal computer 204, and the interaction between the personal computer 204 and the server 202 may occur at different times.

In some embodiments of the present invention, an individual 100 using the athletic activity monitoring system 10 may participate in the activity with the sensor module 102 physically coupled to the individual's body 106 or to a piece of athletic equipment 108, but with no other portable electronic devices making up part of the athletic activity monitoring system 10 in the individual's immediate vicinity. In such an embodiment, the sensor module 102 would monitor the athletic activity using its sensors. The sensor module 102 may also perform calculations necessary to monitor changes in the spatial orientation of the individual's 100 body 106 or a piece of the individual's athletic equipment 108, or perform calculations necessary to determine a correlation between body 106 or equipment 108 movement data and an activity metric.

Alternatively, in this scenario, other components of the athletic activity monitoring system 10 that are remotely located from the individual 100 during the activity could be relied upon to perform calculations necessary to monitor changes in the spatial orientation of the individual's 100 body 106 or a piece of the individual's athletic equipment 108, or perform calculations necessary to determine a correlation between body 106 or equipment 108 movement data and an activity metric. This could occur, for example after wireless transmission of athletic performance information directly from the sensor module 102 to a personal computer 204 or a server 202 during or after the activity, or after a wired transmission of athletic performance information directly from the sensor module 102 to a personal computer 204 after the activity.

Figure 8A:
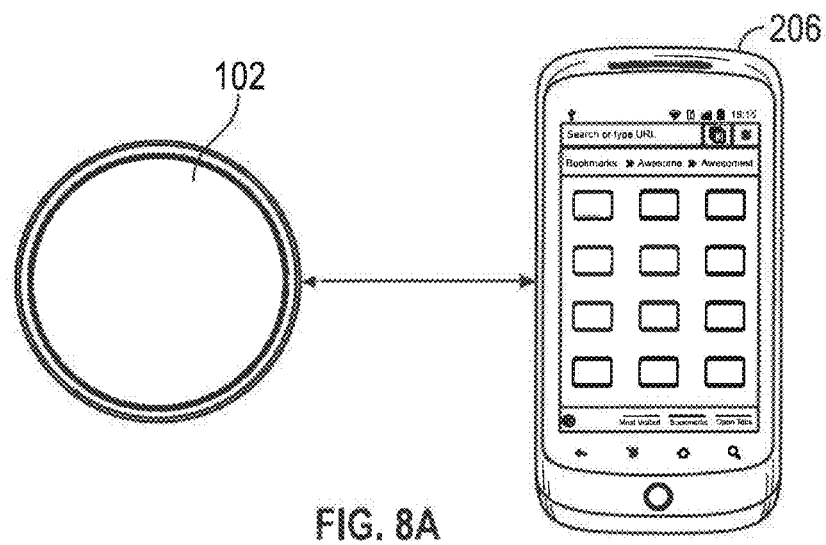
FIG. 8A is an illustration of various components of an athletic activity monitoring system communicating according to an embodiment of the present invention.

However, in other embodiments of the present invention, as illustrated in FIG. 8A, the sensor module 102 may communicate with a portable electronic device 206 of the athletic activity monitoring system 10 that is also carried by the individual 100 during the athletic activity. In some embodiments, the portable electronic device 206 may be a watch, a mobile phone, a tablet computer, or other portable electronic device.

The portable electronic device 206 may serve a variety of purposes including, for example, providing additional data processing, providing additional data storage, providing data visualization, providing additional sensor capabilities, relaying information to a network 200, or providing for the playback of music.

In one embodiment of the present invention, the portable electronic device 206 may be a dedicated portable electronic device 206. The term "dedicated portable electronic device" indicates that the portable electronic device 206 is not capable of serving another purpose outside of the athletic activity monitoring system 10 of the present invention. For example, a mobile phone, a personal digital assistant, or a digital music file player (e.g., an MP3 player) may not be considered to be "dedicated portable electronic monitoring devices" as the term is used herein. In this manner, the dedicated portable electronic monitoring device 206 may in some embodiments provide a simpler and/or more efficient device.

The portable electronic device 206 illustrated in FIG. 8A is not a dedicated portable electronic monitoring device; the portable electronic device 206 illustrated in FIG. 8A is a mobile phone. In alternate embodiments, it may be possible for the sensor module 102 itself to be embodied by a mobile phone. Including a portable electronic device 206 in the athletic activity monitoring system 10, such as a mobile phone, may be desirable as mobile phones are commonly carried by individuals, even when engaging in athletic activities, and they are capable of providing significant additional computing and communication power at no additional cost to the individual 100.

In view of the above discussion, it is apparent that various processing steps or other calculations recited herein may be capable of being performed by various embodiments of the athletic activity monitoring system 10 disclosed herein, and are not necessarily limited to being performed by the sensor module 102, depending on the configuration of a particular embodiment of the present invention. For example, any of the processing steps or other calculations recited herein may be performed, in various embodiments, by the sensor module 102, by a server computer 202, by a personal computer 204, by a portable electronic device 206, and/or any other network component, or by more than one component.

Embodiments of the present invention may involve the use of so-called "cloud computing." Cloud computing may include the delivery of computing as a service rather than a product, whereby shared resources, software, and information are provided to computers and other devices as a utility over a network (typically the Internet). Cloud computing may entrust services (typically centralized) with a user's data, software and computation on a published application programming interface over a network. End users may access cloud-based applications through a web browser or a light weight desktop or mobile app while the business software and data are stored on servers at a remote location. Cloud application providers often strive to give the same or better service and performance than if the software programs were installed locally on end-user computers.

Figure 8B:
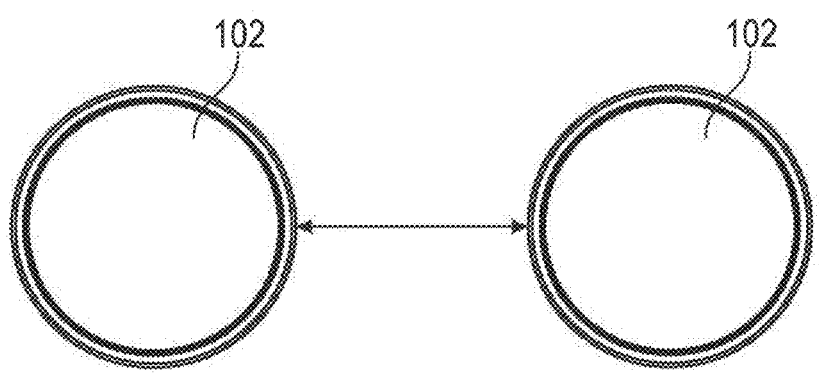
FIG. 8B is an illustration of two sensor modules communicating according to an embodiment of the present invention.

FIG. 8B illustrates a first sensor module 102 in wireless communication with a second sensor module 102. In an embodiment, such communication may be desirable so that different individuals 100, including individuals 100 on the same athletic team, can compare their performance in athletic activities or otherwise exchange data without having to first transmit data through a remote computer such as a personal computer 204 or a server 202.

Figure 9:
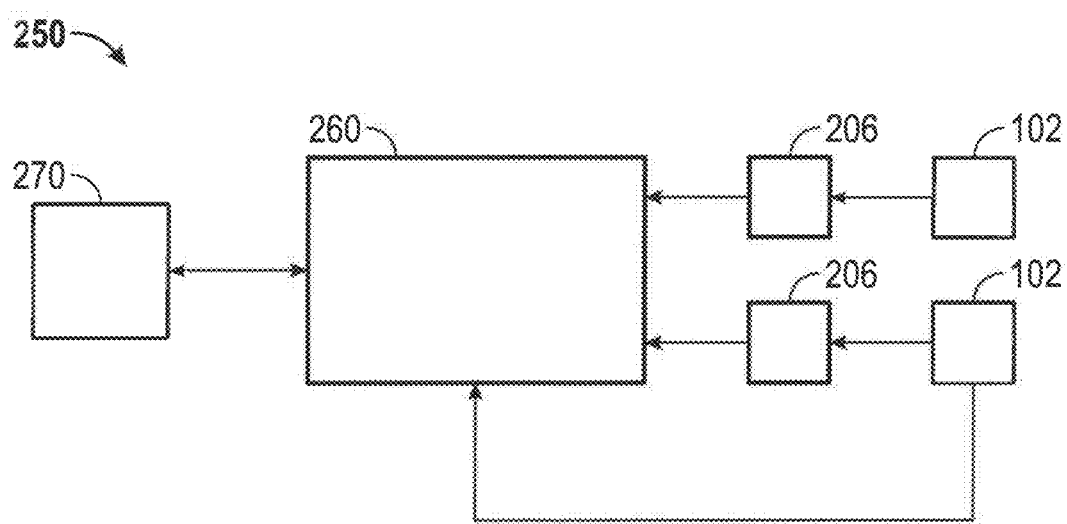
FIG. 9 is an illustration of a group monitoring system according to an embodiment of the present invention.

FIG. 9 is an illustration of a group monitoring system according to an embodiment of the present invention. In an exemplary embodiment, group monitoring system 250, depicted in, for example, FIG. 9, includes portable electronic devices 206, a base station 260, and at least one group monitoring device 270. Portable electronic device 206 may be coupled to an individual 100. Portable electronic device 206 may include or be in communication with a sensor module 102 or individual sensors associated with an individual 100 or their athletic equipment 108, including, but not limited to, an acceleration sensor 116, a magnetic field sensor 118, a pedometer, a heart rate monitor, a position sensor, an impact sensor, a camera, a gyroscope, a microphone, a temperature sensor, and a wind sensor.

In an exemplary embodiment, the portable electronic device 206 and/or the sensor module 102 may include a sensor garment, a heart rate monitor, and a position sensor. The position sensor may include, for example, a position sensor for use with a satellite-based positioning system, a position sensor for use with a beacon system (e.g., position determination using triangulation and/or time differences of signals received by antennas at known positions about a field or activity area), or a position sensor for use with any other suitable position-determining system. In some exemplary embodiments, group monitoring device 270 may be used by a coach.

Sensor modules 102 may be mounted to individuals 100 in preparation for participation by individuals 100 in a session of athletic activity. Sensor modules 102 mounted to a particular individual 100 may be coupled, either via wires or wirelessly, to a portable electronic device 206, also mounted on the particular individual 100. The sensor modules 102 may sense characteristics about individuals 100 during participation by individuals 100 in the session of athletic activity, and transmit data indicative of the characteristics to the portable electronic device 206. The portable electronic device 206 in turn transmits the data to base station 260 during the session of athletic activity.

In some exemplary embodiments, this transmission occurs in real time. "Real time" as used herein may include delays inherent to transmission technology, delays designed to optimize resources, and other inherent or desirable delays that would be apparent to one of skill in the art. In some exemplary embodiments, this transmission is delayed from real time, or may occur after completion of the activity. Base station 260 may receive the data and may determine metrics from the data, where the metrics may be representations of the characteristics measured by sensor modules 102, or may be representations of further characteristics derived from the data through the use of algorithms and other data manipulation techniques. Base station 260 in turn may transmit the metrics during the session of athletic activity to group monitoring device 270, which may receive the metrics and display a representation of the metrics.

Group monitoring device 270 may receive metrics associated with a plurality of individuals 100, and may display the received metrics in association with the individuals 100 with which they are associated. In this way, a coach viewing group monitoring device 270 during the session of athletic activity receives detailed information about multiple individuals 100, and can act on that information as it is determined necessary or expedient, thereby efficiently monitoring and managing individuals 100 during the session of athletic activity.

In some exemplary embodiments, sensor module 102 or portable electronic devices 206 calculate metrics based on the data, and transfer these metrics to base station 260 along with or instead of the data. In some exemplary embodiments, base station 260 transmits the data to group monitoring device 270, along with or instead of the metrics. In some exemplary embodiments, group monitoring device 270 calculates metrics based on the data.

Base station 260 may be a self-contained portable system, containing all hardware required or desired to perform the functions of base station 260 described herein. In some exemplary embodiments base station 260 is configured to be portable. In some exemplary embodiments, base station 260 is configured to be positioned at an activity site. In some exemplary embodiments base station 260 is configured to be movable between activity sites such that it can be positioned at various activity sites. In some exemplary embodiments, base station 260 itself includes sensors, such as, for example, a GPS sensor (or other position sensor), a gyroscope, a magnetometer, a temperature sensor, a humidity sensor, and/or a wind sensor. Such sensors can provide valuable data that can be used in algorithms to determine metrics associated with individuals 100, as will be described below.

In some exemplary embodiments, base station 260 includes a reference sensor (e.g., a GPS reference sensor), which may be physically included within base station 260 or independent of and located remote from base station 260 at a known position with respect thereto. Reference sensor can be connected to base station 300 via wires or wirelessly. Reference sensor can be used to detect a deviation signal and use it to calculate a correction signal for received position signals (e.g., GPS data). This correction signal can be sent to a sensor module 102 or a portable electronic device 206 (e.g., via base station 300). This correction signal can be used to correct position determinations of sensor module 102 or portable electronic devices 206, thereby increasing their accuracy. Determining such a correction signal and then sending it to sensor module 102 or portable electronic devices 206 achieves efficient use of processing capacity, because sensor module 102 or portable electronic devices 206 are not burdened with determining a correction signal themselves, but simply receive and use a correction signal determined at base station 260 or reference sensor.

Base station 260 may transmit and receive data from sensor module 102 or portable electronic devices 206 via an antenna configured for one or more of RF communication, WLAN communication, ISM communication, cellular (e.g., GSM broad band 2.5G or 3G) communication, other suitable communication, or a combination thereof. Communication between base station 260 and sensor module 102 or portable electronic devices 206 may be bi-directional or uni-directional. Base station 300 can then determine metrics from the received data. As described above, base station 260 receives data from sensor modules 102 or portable electronic devices 206. Data reception module of base station 260 may be in communication with each active sensor module 102 or portable electronic device 206.

Group monitoring device 270 can wirelessly receive metrics, alerts, and other information (e.g., identification information and attributes of individuals 100, or statistics relevant to individuals 100 or the athletic activity generally) from base station 260. A single group monitoring device 270 may be in communication with base station 260, or multiple group monitoring devices 270 may be in communication with base station 260 simultaneously. Group monitoring devices 207 may be portable with respect to base station 260 and may communicate with base station 260 via, for example, WLAN (wireless local area network), 2.4 GHz ISM (industrial, scientific, and medical) band, Bluetooth (or Bluetooth Low Energy (BTLE)), or cellular protocols.

In some exemplary embodiments, group monitoring device 270 includes a module selection element which allows selection of one or more operation modules to be displayed. The operation modules may be selectable using operation module icons. In some exemplary embodiments, selection of a plan module icon may trigger display of a plan module including features designed to be used to plan a session of athletic activity. In some exemplary embodiments, selection of a monitor module icon may trigger display of a monitor module including features designed to be used to monitor a session of athletic activity in real time during the session of athletic activity, as described further herein. In some exemplary embodiments, selection of an analyze module icon may trigger display of an analyze module including features designed to be used to analyze a session of athletic activity in real time during the session of athletic activity, or after completion of the session of athletic activity, as described further herein. In some exemplary embodiments, selection of a report module icon may trigger display of a report module including features designed to be used to develop reports (e.g., printable or displayable summaries of selected information) related to a session of athletic activity.

In some exemplary embodiments, group monitoring device 270 includes a display and an input. In a preferred embodiment, group monitoring device 270 is a tablet computing-style device (such as a tablet personal computer or an IPAD brand tablet, marketed by Apple Inc.). Group monitoring device 270 may be, however, any other suitable device, such as, for example, a laptop computer, a smartphone, a personal computer, a mobile phone, an e-reader, a PDA (personal digital assistant), a smartphone, or other similar device capable of receiving and displaying information and receiving input.

In some embodiments, the sensor module 102 is incorporated into a sensor garment 500 (e.g., a jersey, glove, hat) that may be formed of a textile material 530, for example, wool, cotton, acrylic, polyester, nylon, elastane/spandex, silk, acetate, polypropylene, rayon, viscose, polylactic acid (PLA), and biopolymers. Such sensor module 102 may be inseparable from the balance of sensor garment 500. In other words, the sensor module 102 may be so attached to material of the sensor garment 500 that the sensor module 102 is not removable therefrom in normal use throughout the operational life of the sensor garment 500 without damaging the sensor garment 500. For example, the sensor module 102 may be small, lightweight, and flexible such that it can be incorporated into the textile material of the sensor garment 500 without negatively impacting a wearer's comfort or use of the sensor garment 500 when wearing the sensor garment 500. In other words, the incorporation of the sensor module 102 into the sensor garment 500 may not be tactilely perceptible to a wearer, or may be only minimally tactilely perceptible. For example, to minimize tactile impact, the sensor module 102 may be formed in whole or in part from a flexible printed circuit board (PCB). In some embodiments, sensor module 102 is a similar size and flexibility as a typical garment label or tag.

For example, in some embodiments the sensor module 102 can be sewn, laser welded, or adhered to the garment in a manner suitable to maintain operation of the sensitive electronics of the sensor module 102. For example, in some embodiments ultrasonic welding of the sensor module 102 to the textile material of the sensor garment 500 may be unsuitable since this technique may damage or destroy the sensitive electronics of the sensor module 102.

In some embodiments, the sensor module 102 may be encapsulated within the sensor garment 500 during manufacturing of the sensor garment or material to be formed into the sensor garment 500. For example, in some embodiments the sensor module 102 may be disposed within a knitted or woven pocket of the sensor garment 500 (e.g., that has been knitted or woven around sensor module 102 to secure it in place, including by three-dimensional knitting or weaving). Also for example, in some embodiments the sensor module 102 may be retained within sensor garment 500 by braiding thereof (e.g., braids of material forming sensor garment 500 may extend across the sensor module 102 to secure it in place).

In some embodiments, the sensor module 102 (or components thereof) may be printed onto the sensor garment 500. For example, in some embodiments the circuitry of sensor module 102 may be printed directly on material forming sensor garment 500 including, for example, a thermoplastic polyurethane or polyurethane patch of the sensor garment 500. In some embodiments the sensor module 102 may be laminated on or between layers of the sensor garment 500.

In some embodiments, particularly where the sensor module 102 is incorporated into the sensor garment 500, the sensor module 102 may have a simplified electronic structure, in order to optimize miniaturization, power consumption, and circuit complexity. For example, in some embodiments the sensor module 102 may not include a magnetic field sensor. In some embodiments, the sensor module 102 may include no sensor other than an acceleration sensor (e.g., acceleration sensor 116). Such a simplified sensor arrangement allows a focused data set to be transmitted to the portable electronic device 206 or base station 260 (i.e., only acceleration data), thereby further increasing operational efficiency (e.g., energy, size, weight, complexity). For example, where the sensor module 102 includes a single-purpose sensor configured to sense a single characteristic (e.g., acceleration sensor 116 configured to sense acceleration, magnetic field sensor 118 configured to sense magnetic field), the sensor module 102 may have limited computational requirements (e.g., due to receiving input from only a single-purpose sensor), and thus processor power requirements can be minimized, allowing use of a power source 112 having minimal size, thereby optimizing the size of the sensor module 102. For example, to optimize the size of the sensor module 102, the power source 112 of the sensor module 102 may be a thin-film battery or super capacitor. Such a thin film battery may be, for example, a Solid-State, Flexible, Rechargeable Thin-Film Micro-Energy Cell such as the THINERGY® MEC225 Micro-Energy Cell, which is manufactured by Infinite Power Solutions®, and which has dimensions of approximately 12.7 millimeters (mm)×12.7 mm×0.170 mm, and mass of approximately 125 milligrams. In some embodiments, power source 112 may be a solar cell (e.g., a flexible solar cell) or may be charged by a solar cell. Such solar cell may be incorporated into the sensor module 102 or may be separate therefrom. In some embodiments power source 112 may be a kinetic energy conversion unit (e.g., an electrical generator driven by pendulum oscillation) or may be charged by a kinetic energy conversion unit. Such kinetic energy conversion unit may be incorporated into the sensor module 102 or may be separate therefrom. In some embodiments, power source 112 may be a thermoelectric generator (e.g., a generator powered by a thermal gradient across semiconductors, where the thermal gradient may be due at least in part to a wearer's body heat) or may be charged by a thermoelectric generator. Such thermoelectric generator may be incorporated into the sensor module 102 or may be separate therefrom.

Useful physiological parameters can be derived from data received from a single sensor, particularly where the sensor is permanently incorporated into a garment in a way that is only minimally tactilely-perceptible to the wearer, in which case it will not significantly impact the wearer's athletic performance. For example, a sensor module 102 that includes only an acceleration sensor 116 can be used to measure jump height of a wearer 100. Calculation of jump height from acceleration data is described in greater detail below. In some embodiments, the sensor module 102 may include alternative or additional sensors to acceleration sensor 116 and magnetic field sensor 118. For example, sensor module 102 may include a temperature sensor, a humidity sensor, a heart rate sensor, or a non-invasive lactate sensor to measure temperature, humidity, heart rate, or lactate level.

Figure 35:
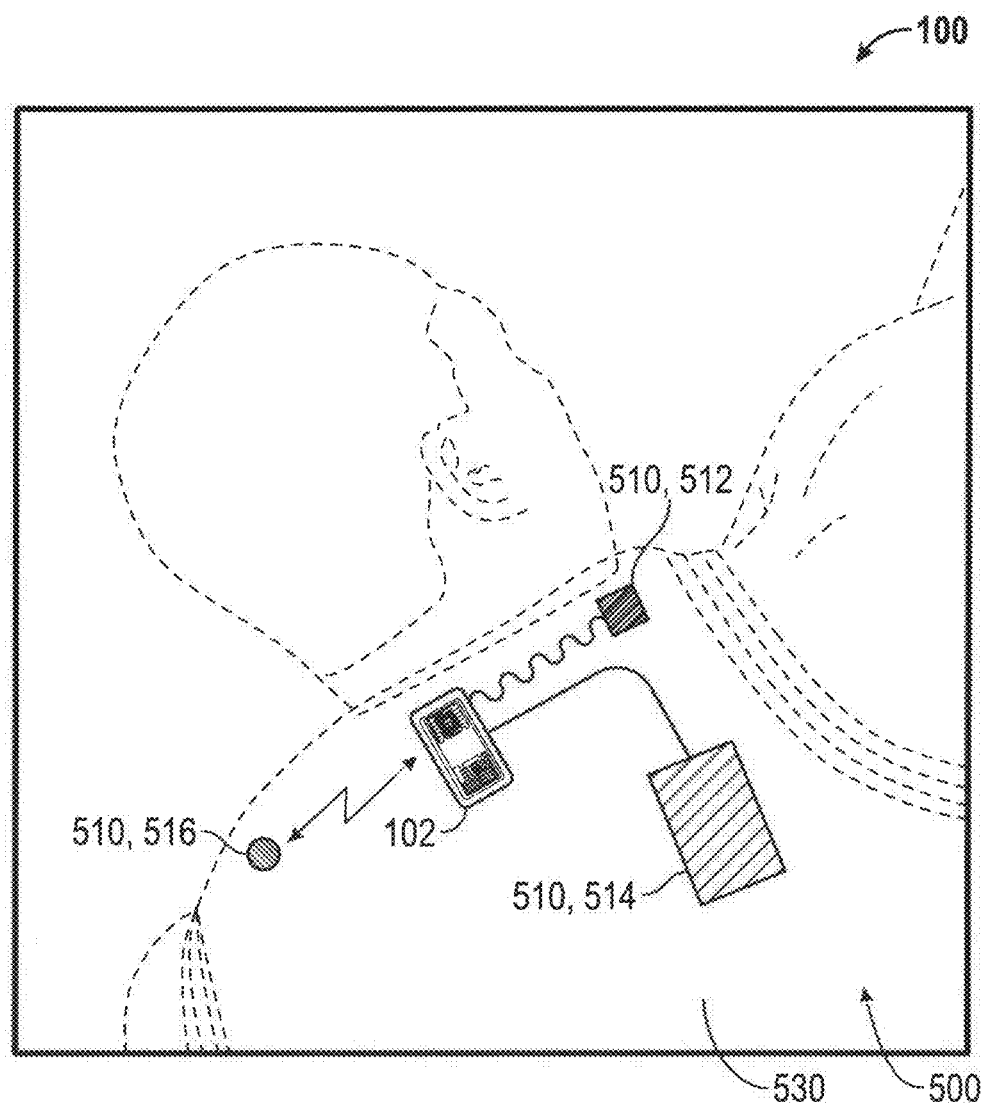
FIG. 35 is an illustration of a sensor module in use in a sensor garment according to an embodiment of the present invention.

Sensor module 102 may be positioned in any desired location on a garment. For example, sensor module may be positioned at or near the expected center of mass of an individual 100, or along the centerline of the individual's 100 torso (see, e.g., FIG. 35).

In some embodiments, the sensor module 102 may sense parameters to determine the fit or ventilation level of sensor garment 500 on wearer 100 during activity. For example, where the sensor garment 102 includes an acceleration sensor 116, the sensed acceleration data can be used to determine whether a garment is too tight or too loose, or provides adequate ventilation, based on the degree and pattern of acceleration of sensor 102. For example, acceleration data showing acceleration magnitude and/or frequency above or below threshold levels may indicate improper fit, or inadequate ventilation. For example, high acceleration sensed from garment fabric "flapping" during athletic movement may indicate the garment fits too loosely, or may indicate a high level of ventilation. Such information can be useful to assist proper garment size selection, particularly in a performance or therapeutic garment that should have a certain fit (e.g., a compression garment). Multiple acceleration sensors 116 (e.g., low-mass accelerometers) may be positioned throughout the sensor garment 500 to provide data showing fit or ventilation of different areas of sensor garment 500.

In some embodiments, the sensor module 102 is not physically coupled to another device, but communicates with such a device (e.g., portable electronic device 206) wirelessly. For example, the acceleration sensor 116 of the sensor module 102 may sense acceleration data, which may be sent wirelessly by the sensor module 102 to a paired portable electronic device 206, which may process the data, store the data, and/or communicate it (e.g., wirelessly) to a further receiver (e.g., the base station 206 or an Internet-connected device or server) for processing and/or storage.

The portable electronic device 206 may be incorporated in or carried by the sensor garment 500 or may be mounted on or carried by an individual 100 wearing the sensor garment 500 (where sensor garment 500 has the sensor module 102 incorporated therein). For example, the portable electronic device 206 may be a smartphone, tablet computer, or other personal electronic device. In some embodiments, the portable electronic device is another sensor module 102 of garment 500. In embodiments where sensor garment 500 includes more than one sensor module 102, each sensor module 102 may include the same sensor for sensing the same parameter at different locations, or at least two sensor modules 102 may include different sensors (e.g., one with acceleration sensor 116 and one with magnetic field sensor 118) for sensing different parameters.

Figure 36:
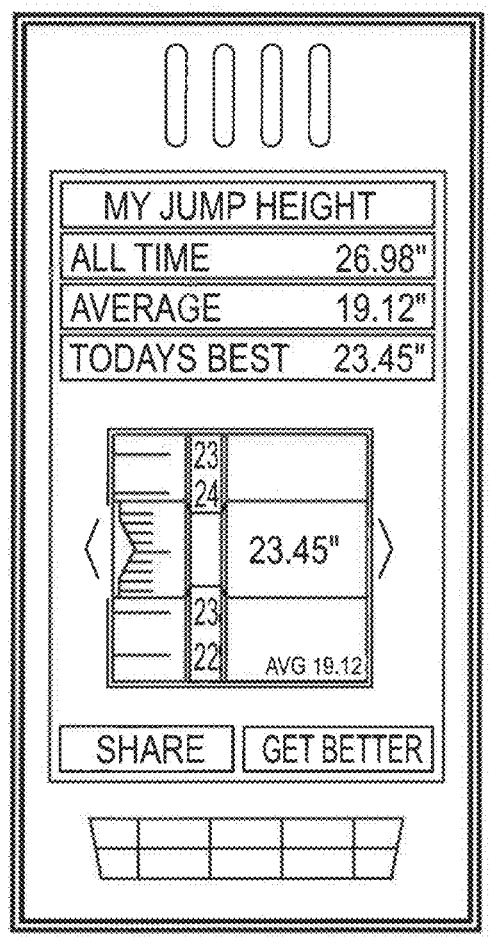
FIG. 36 is an illustration of a display according to an embodiment of the present invention.

In some embodiments, the transceiver 122 of the sensor module 102 includes a radio antenna (e.g., an NFC antenna) configured to communicate bi-directionally with the portable electronic device 206 using Near Field Communication (NFC) or another low-power wireless communication protocol (e.g., active radio-frequency identification (RFID), Bluetooth, BTLE, or any electromagnetic-field-based communication protocol). For example, in some embodiments, the portable electronic device 206 can be used to activate or de-activate (i.e., turn "on" or "off") the sensor module 102 or components/features thereof, to receive sensor data from the sensor module 102 (e.g., for storage, processing, or retransmission), to output performance data received from or derived from data received from the sensor module 102 (e.g., on a display screen of the portable electronic device 206), or to transmit sensor data or performance data to a further receiver (e.g., the base station 206 or an Internet-connected device or server). For example, FIG. 36 shows the portable electronic device 206 outputting a representation of the jump height of a monitored individual 100, where the jump height has been derived from acceleration data received from the sensor module 102 having no sensor other than the acceleration sensor 116.

In some embodiments, the sensor module 102 is paired with a particular portable electronic device 206 such that the paired portable electronic device 206 receives data only from the sensor module 102 with which it is paired. This can help facilitate the use of the athletic activity monitoring system 10 by a plurality of users in the same vicinity (e.g., on the same playing field), since data from the sensor module of a particular user 100 will not be received by portable electronic devices 206 of other users.

In some embodiments, particularly where the sensor module 102 is incorporated into the sensor garment 500, the sensor module 102 may be structurally configured to withstand conditions to which athletic garments are typically subjected. For example, the sensor module 102 may be configured to withstand impacts due to athletic use (e.g., impacts due to a wearer's motion such as jumping, running, falling, impacts due to strikes by sports equipment such as a soccer ball, baseball, golf club, impacts due to contact and collisions with other players, and impacts due to garment maintenance, such as tumbling in a washing or drying machine). To withstand such impacts, sensor module 102 may be flexible such that sensor module 102 can absorb impact forces by flexing, rather than breaking.

Figure 33:
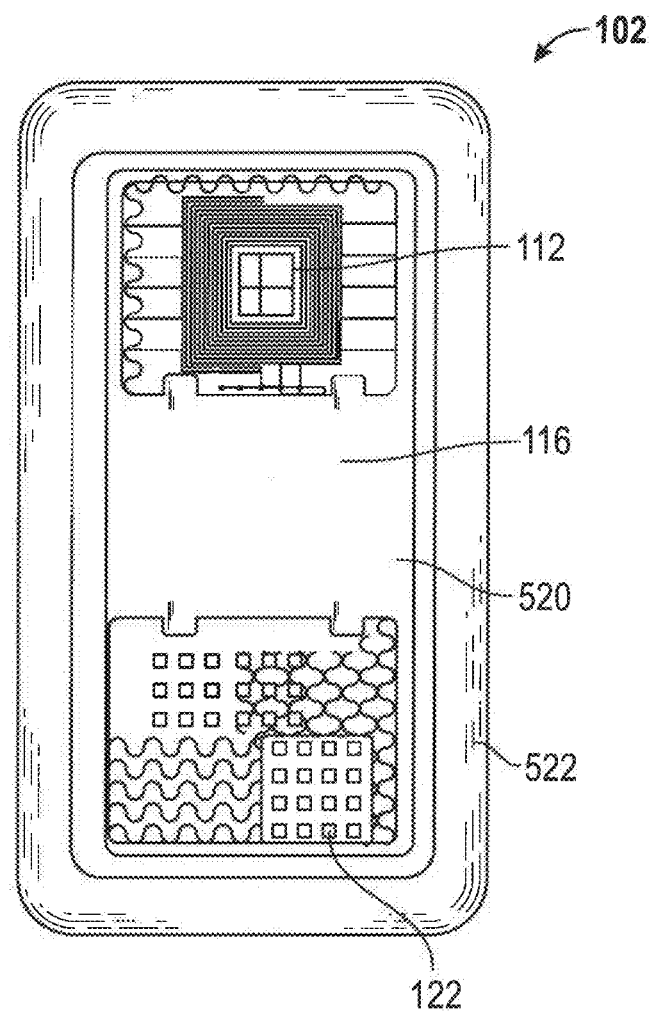
FIG. 33 is an illustration of a sensor module according to an embodiment of the present invention.
Figure 34:
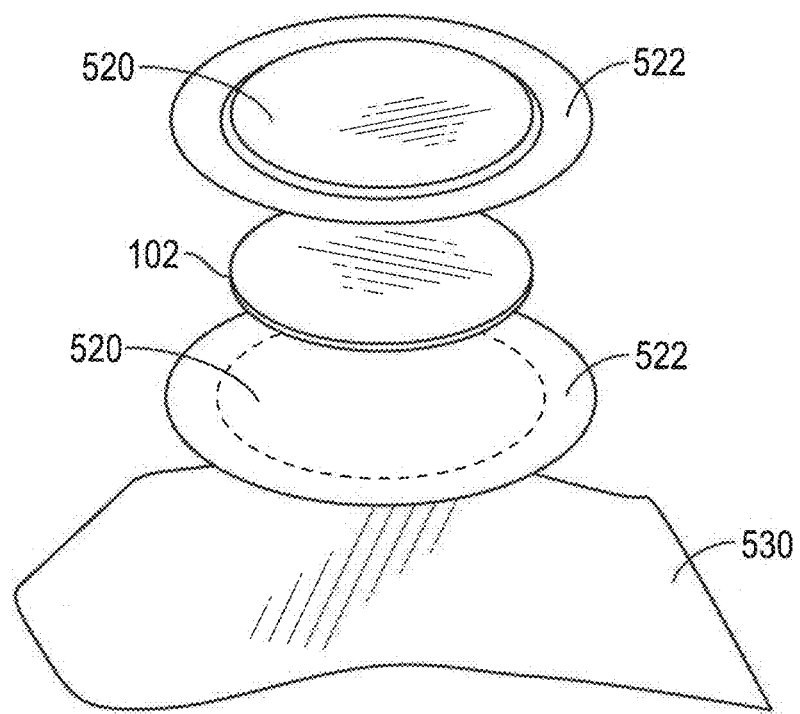
FIG. 34 is an illustration of a sensor module according to an embodiment of the present invention.

Also for example, the sensor module 102 may be configured to withstand high-moisture environmental conditions incidental to athletic use (e.g., high moisture conditions due to a wearer's perspiration, use in rain, submersion in water, use in humid environments, or use in a washing machine). To withstand such high-moisture environments, the sensor module 102 may be sealed inside a waterproof membrane (e.g., the housing 136 may be formed of a waterproof membrane). For example, as shown in FIGS. 33 and 34, the sensor module 102 or components thereof (e.g., its printed circuit board and electronics) may be sealed in a thermoplastic polyurethane (TPU) or thin-film sandwich (i.e., sealed between two thermo formable films/substrates 520) to render them waterproof and launderable. The thermo-formable films/substrates 520 may have a perimeter 522 extending beyond and around the sensor module 102, such that the perimeter 522 of a top thermo formable film/substrate 520 contacts and bonds with the perimeter 522 of a bottom thermo formable film/substrate 520 (e.g., by heat welding). The waterproof membrane, by limiting exposure of the sensor module 102 components, may also improve mechanical durability of the sensor module 102 by protecting the sensor module 102 from mechanical damage.

Also for example, the sensor module 102 may be configured to withstand high- or low-temperature environmental conditions incidental to athletic use (e.g., high or low temperature due to the temperature of a wearer's body and/or the atmospheric temperature at the location used, or due to heat applied to dry the garment, such as is applied in a drying machine).

In some embodiments, particularly where the sensor module 102 is incorporated into sensor garment 500, the sensor module 102 may include no external ports (e.g., no external data ports, no external power ports, or both). In other words, an exterior of the sensor module may be portless. In such an embodiment, the power source 112 of the sensor module 102 may be charged through inductive charging, wherein an electromagnetic field is used to transfer energy from an inductive charger to the power source 112 when the two are brought in close proximity. In some embodiments, an external power source may transmit power to the power source 112 using the NFC radio. For example, the NFC power source can be used to trickle-charge power source 112 where the NFC radio is in close proximity to the NFC power source. In some embodiments, the inductive charger or other external power source may be integrated into a clothes hanger upon which sensor garment 500 may be stored, so that the power source 112 of the sensor module 102 can be and remain charged while the sensor garment 500 is stored.

In some embodiments, the sensor module 102 communicates sensed data to the paired portable electronic device 206 in real time. In some embodiments, the sensor module 102 alternatively communicates sensed data to the portable electronic device 206 or other receiver (e.g., base station 260) periodically (e.g., after completion of a session of athletic activity sensed by sensor module 102). In such an embodiment, sensor module 102 may store sensor data in an internal memory 114 until the sensor data is transmitted to the portable electronic device 206 or other receiver. In some embodiments, sensor module 102 may not include an internal memory. In some embodiments, sensor garment 500 includes an external memory device 512 incorporated into or carried by sensor garment 500, which can store sensor data received from sensor module 102. Sensor module 102 may transmit such sensor data to the external memory device 512 via wires or wirelessly (e.g., via NFC) using any known or future developed wireless protocol, including those described herein. The external memory device 512 can be used to store sensor data in embodiments where sensor module 102 does not include an internal memory and while sensor module 102 is sensing sensor data but not communicating such sensor data to the portable electronic device 206 or other receiver in real time. Also, the external memory device 512 can be used to effectively increase the capacity of the internal memory 114 of sensor module 102, in embodiments where the sensor module 102 includes the internal memory 114, thus allowing sensor module 102 to be used for longer or to collect more data without transmitting the data to the portable electronic device 206 or other receiver.

In some embodiments, sensor garment 500 includes an external power source 514 incorporated into or carried by sensor garment 500, which can provide power to the sensor module 102 or other components integrated into or carried by the sensor garment 500 in the same manner as described elsewhere herein (e.g., via inductive charging or NFC power transmission). The external power source 514 can extend the effective battery life of the internal power source 112 of sensor module 102, thereby allowing a user 100 to continuously use sensor garment 500 without the need to stop athletic activity to re-charge internal power source 112.

In some embodiments, sensor garment 500 includes an external radio antenna 516 incorporated into or carried by sensor garment 500, which may be stronger than the radio antenna incorporated into the sensor module 102, and which may thereby enable transmission of sensor data across farther distances (e.g., directly to base station 260 on the sideline of a playing field). For example, the external radio antenna 516 may communicate using any known or future developed wireless protocol, such as, for example, CDMA, GSM, EDGE, 3G, 4G, IEEE 802.x (e.g., IEEE 802.16 (WiMAX)). The external radio antenna 516 may receive sensor data from the sensor module 102 wirelessly (e.g., via NFC).

Any of the external components 510 (e.g., external memory device 512, external power source 514, or external radio antenna 516) can be removably coupled to the sensor garment 500 with a mechanical attachment mechanism (e.g., with magnetic attachments, hook-and-loop fasteners, buttons, snaps, zippers) or by placing the sensor module 102 within a pocket of the sensor garment 500. Any of the external components 510 can be configured to electronically connect (e.g., to send power or to send and/or receive data) with the sensor module 102, for example, via wires or wirelessly using any known or future developed wireless protocol, including those described herein. Further, any one or more of the external components 510 could be a separate personal electronic device, such as, for example, a smartphone or tablet computer.

Suitable group monitoring systems and components may include, for example, the systems and components disclosed in commonly owned U.S. patent application Ser. No. 13/077,494, titled "Group Performance Monitoring System and Method," which is incorporated herein by reference in its entirety.

An overview of exemplary embodiments of components of the athletic activity monitoring system 10 of the present invention, including exemplary sensor modules 102, has been provided above. A description of various exemplary methods of using the athletic activity monitoring system 10 of the present invention to monitor changes in the spatial orientation of the individual's 100 body 106 or a piece of the individual's athletic equipment 108, or to determine a correlation between body 106 or equipment 108 movement data and an activity metric is now provided below.

An individual 100 engaged in an athletic activity (or another interested person such as a coach, teammate, or spectator) may desire to obtain information about the motion of the individual's 100 body 106 or the motion of a piece of the individual's athletic equipment 108 during the course of the athletic activity.

For example, if the individual 100 is participating in an activity that involves the use of a sport ball, such as playing in a soccer match, it may be desirable, for example, to be able to determine the various launch angles at which the soccer ball (i.e., football) was kicked by the individual 100, to be able to determine the rate of rotation of the soccer ball after it was kicked by the individual 100, or to be able to determine the peak speeds that the soccer ball was traveling at after being kicked by the individual 100.

As a further example, if the individual 100 is participating in an activity that involves various movements the individual's 100 chest, such practicing basketball skills, it may be desirable, for example, to be able to identify instances when the individual 100 cut to the left or cut to the right when trying to dribble around a defender, to be able to determine the height that the individual 100 jumped or the force that the individual 100 jumped with when taking jump shots, attempting dunks, or attempting to block shots, or to be able to determine the individual's 100 reaction time when working on basketball-related reaction time drills.

By using the athletic activity monitoring system 10 including the sensor module 102 described above, embodiments of the present invention may advantageously enable the individual 100 (or their coach, teammate, or a spectator) to obtain this or other information about the motion of the individual's 100 body 106 or the motion of a piece of the individual's 100 athletic equipment 108 during or after the course of the athletic activity.

While various embodiments of the present invention are described in the context of the sports of soccer (i.e., football) and basketball, the present invention is not so limited and may be applied in a variety of different sports or athletic activities including, for example, baseball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto. In addition, activity metrics described as being capable of being determined in soccer may be capable of being determined in basketball, or vice versa, when appropriate.

Data obtained by the sensor module 102 may be processed in a variety of ways to yield useful information about the motion of an object 104 of interest during the activity. In some embodiments, sensor module 102 data may be processed to monitor changes in the spatial orientation of the individual's 100 body 106 or a piece of the individual's 100 athletic equipment 108. In other embodiment, sensor module 102 data may be processed to by reference to a predetermined correlation between movement data and an activity metric stored in a data structure.

Regardless of whether the athletic activity monitoring system 10 and the sensor module 102 are being used to monitor the individual's 100 body 106 or a piece of the individual's 100 athletic equipment 108, in embodiments of the present invention where there is a desire to monitor changes in the spatial orientation of the individual's 100 body 106 or the piece of the individual's 100 athletic equipment 108, a common analytical framework may be used to carry out the monitoring. This analytical framework is illustrated by FIG. 12.

Figure 12:
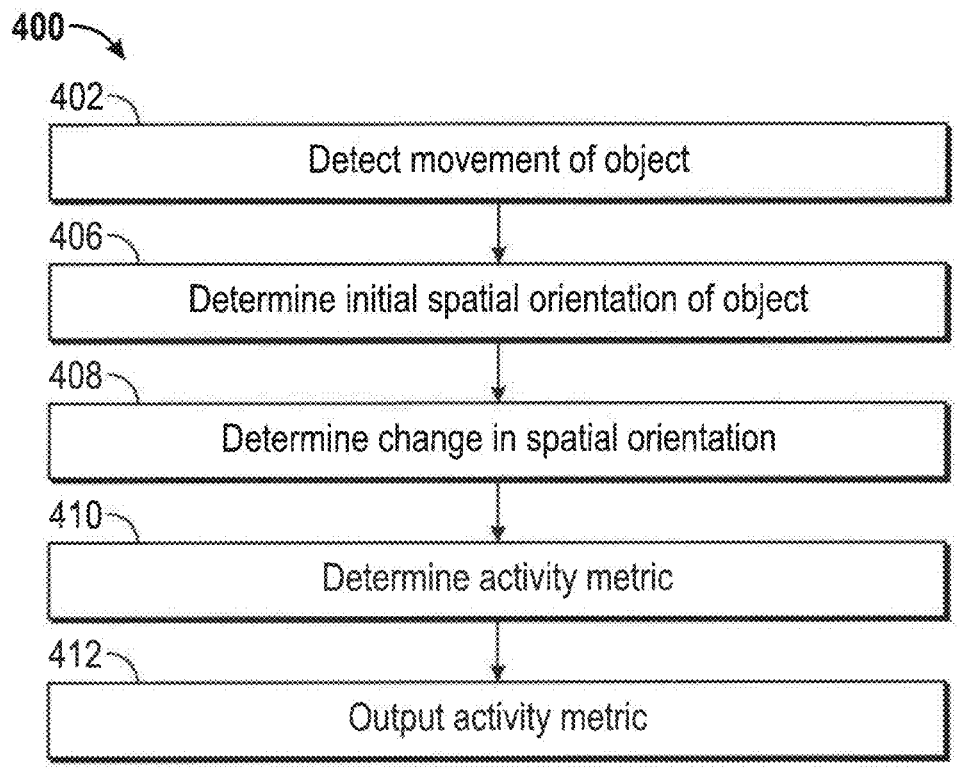
FIG. 12 is flow chart illustrating a method for determining an activity metric according to an embodiment of the present invention.

With reference to FIG. 12, in such an embodiment, the individual 100 may use the sensor module 102 in the athletic activity monitoring system 10 to determine a change in spatial orientation of the object 104 according to spatial orientation process 400 as follows.

First, at step 402, the sensor module 102 may detect movement of the object 104. In one embodiment, movement of the object 104 is detected based on acceleration data captured by the acceleration sensor 116 of the sensor module 102. In another embodiment, movement of the object 104 is detected based on magnetic field data captured by the magnetic field sensor 118 of the sensor module 102. In yet another embodiment, movement of the object 104 is detected based on both acceleration data and magnetic field data.

In one embodiment, the magnetic field sensor 118 may be adapted to measure the strength and direction of magnetic fields in the vicinity of the sensor module 102. In another embodiment, the magnetic field sensor 118 may be adapted to measure the strength and direction of the earth's magnetic field in the vicinity of the sensor module 102. In some embodiments, the magnetic field sensor 118 may be capable of measuring the magnitude and direction of a resultant magnetic vector for the total local magnetic field and/or for the local earth's magnetic field.

If the monitored object 104 is a soccer ball, the detected movement may consist of the soccer ball rolling on the ground as a result of being dribbled by the individual 100. If the monitored object 104 is the chest of an individual 100 playing basketball, the detected movement may consist of the individual's chest moving forward as the individual dribbles a basketball down the court.

In some embodiments, the sensor module 102 may then determine that the movement of the object 104 indicates the occurrence of a movement to track. In one embodiment, the determination that the movement of the object 104 indicates the occurrence of a movement to track occurs when a threshold data value is met for a predetermined period of time. For example, the sensor module 102 may determine that a movement of the object 104 has resulted in a threshold acceleration and/or magnetic field change occurring for a predetermined period of time.

In some embodiments, the determination of the occurrence of a movement to track is an indication that the movement to track had already begun prior to the determination. In this case, it is still possible to capture all of the relevant data relating to the movement as the sensor module 102 may temporarily record a stream of data in a buffer in the event that data that had recently been recorded may need to be examined or more permanently recorded in response to a determination that an occurrence of a movement to track is found. In other embodiments, the determination of the occurrence of a movement to track is an indication that the movement to track is about to begin in the near future. In some embodiments, the sensor module 102 is adapted to store data permanently or temporarily, and may further be adapted to store data for predefined periods of time in certain circumstances, such as when populating a data buffer.

If the monitored object 104 is a soccer ball, the movement of the soccer ball as a result of the individual 100 swiftly kicking the ball in an attempt to make a goal may result in a determination that the motion of the ball in response to the kick—which could include motion of the ball before, during, and/or after the determination was made—should be tracked. If the monitored object 104 is the chest of an individual 100 playing basketball, the rotation of the individual's 100 chest through one-hundred and eighty degrees of rotation when making an offensive movement may result in a determination that the rotation of the individual's chest—which could include motion of the individual's 100 chest before, during, and/or after the determination was made—should be tracked.

Next, as step 406, in response to the determination of the occurrence of a movement to track, an initial spatial orientation of the object 104 may be determined. In some embodiments, the determination of an initial spatial orientation of the object 104 may be made by reference to a coordinate axis system.

Figure 10:
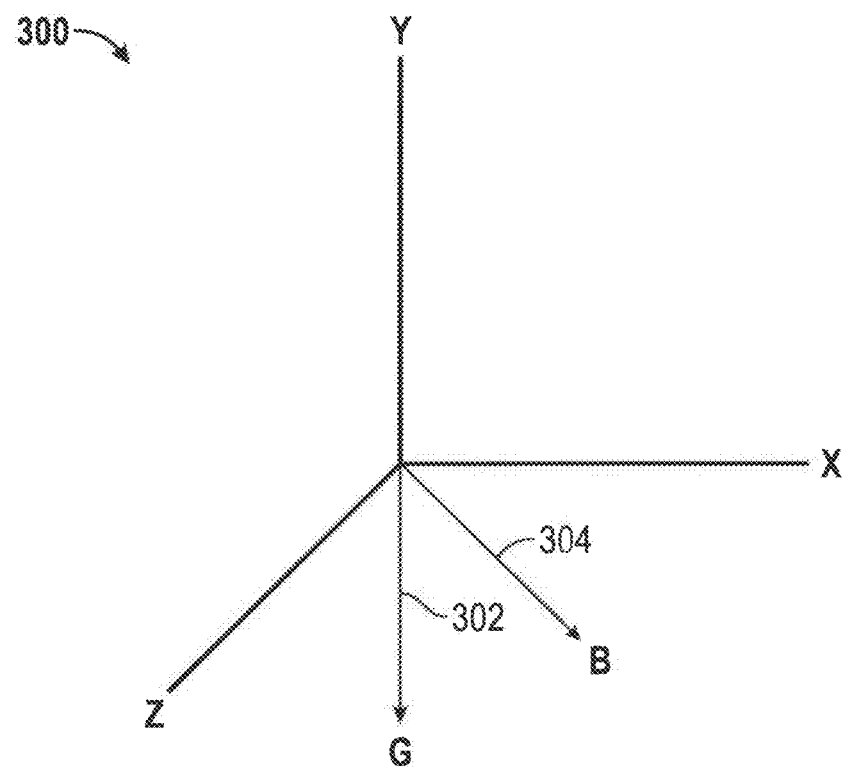
FIG. 10 is an illustration of an exemplary coordinate system according to an embodiment of the present invention.

A coordinate axis system is a useful analytical tool for monitoring changes in the spatial orientation of an object 104. FIG. 10 illustrates an exemplary three-dimensional Cartesian coordinate axis system 300 having three axes—an X axis, a Y axis, and a Z axis. Two vectors, "G" and "B," are superimposed on the coordinate axis system 300 illustrated in FIG. 10. The G-vector 302 pointing in the—Y direction represents a gravity vector. The B-vector 304 represents a resultant magnetic field vector.

Figure 11:
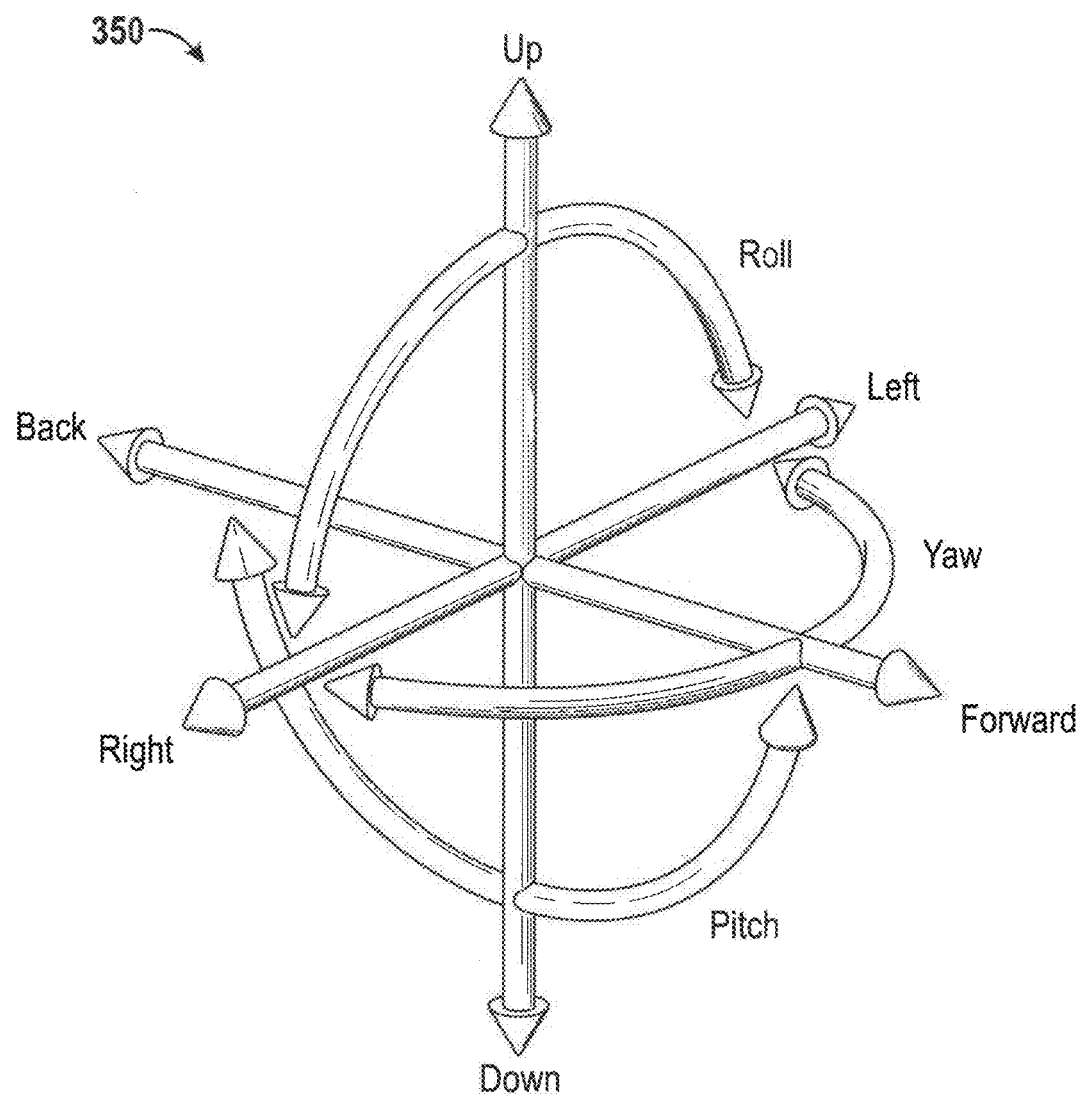
FIG. 11 is an illustration of an exemplary coordinate system according to an embodiment of the present invention.

FIG. 11 illustrates another exemplary three-dimensional Cartesian coordinate axis system 350. This system 350 defines six degrees of freedom for a rigid body, such as the object 104. Six degrees of freedom refers to motion of a rigid body in three-dimensional space, namely the ability to move forward/backward, up/down, left/right (translation in three perpendicular axes) combined with rotation about three perpendicular axes (pitch, yaw, roll), as illustrated in FIG. 11.

Returning to the discussion of step 406, in one embodiment, the determination of the initial spatial orientation of the object 104 may be made with respect to a gravity vector 302, such as that illustrated in FIG. 10. In another embodiment, the determination of the initial spatial orientation of the object 104 may be made with respect to an earth magnetic field vector 304, such as that illustrated in FIG. 10. In other embodiments, the determination of the initial spatial orientation of the object 104 may be made with respect to characterizations of the way that the object translated and rotated in three-dimensional space with six degrees of freedom, as explained with reference to FIG. 11.

If the monitored object 104 is a soccer ball, the determination of the initial spatial orientation of the soccer ball relative to the specific movement to be tracked (i.e., movement of the ball resulting from the kick) may be defined, for example, as the spatial orientation of the soccer ball just before, at the moment of, or just after the soccer ball was swiftly kicked by the individual's 100 foot, depending on the particular application and algorithms used. If the monitored object 104 is the chest of an individual 100 playing basketball, the determination of the initial spatial orientation of the individual's 100 chest relative to the specific movement to be tracked (i.e., the one-hundred and eighty degree rotation) may be defined, for example, as the spatial orientation of the individual's 100 chest just before, at the moment of, or just after the individual's 100 chest began rotating, depending on the particular application and algorithms used.

At step 408, after the determination of the initial orientation of the object 104 at a first time has been made, a change in the spatial orientation of the object 104 may be determined. In an embodiment, the determination of the change in the spatial orientation of the object 104 at step 408 may be made similarly to the determination of the initial orientation of the object 104 at step 406, except that additional information about changes in the orientation of the gravity vector 302 and/or the magnetic field vector 304 as the object moves may be additionally factored in.

If the monitored object 104 is a soccer ball, the determination of the change in the spatial orientation of the soccer ball relative to the specific movement to be tracked (i.e., movement of the ball resulting from the kick) may be defined, for example, as the change in spatial orientation of the soccer ball from the time that the initial orientation of the soccer ball was identified to a later point in time when the ball is still moving or has ceased moving, depending on the particular application and algorithms used. If the monitored object 104 is the chest of an individual 100 playing basketball, the determination of the change in the spatial orientation of the individual's 100 chest relative to the specific movement to be tracked (i.e., the one-hundred and eighty degree rotation) may be defined, for example, as the change in the spatial orientation of the individual's 100 chest from the time that the initial orientation of the individual's 100 chest was identified to a later point in time when the individual's 100 chest is still moving or has ceased moving, depending on the particular application and algorithms used.

At step 410, an activity metric is determined based on the change in the spatial orientation of the object 104 determined in step 408. The nature of the activity metric may change based on the athletic activity that the individual 100 is participating in, as well as particular object 104 that is being monitored. In one embodiment, the activity metric may relate to, for example, a launch angle, a rate of rotation, a speed, a jump height, a jump force, a jump distance, a kick force, a kick distance, a characterization of a specific type of athletic movement, or a reaction time measurement. In other embodiments, the activity metric may be, for example, the rate of rotation, the plane of rotation, the jump force, force profile (force acting upon the body of the athlete or the ground or the object), stroke information in tennis, swing profile in golf, baseball, hockey stick, kick profile of a leg, angle position of a bike pedal, power output of a cyclist, fatigue (tremors starting to occur in repeated motion, i.e., running, lifting swimming, rowing etc.), posture, throwing or arm swing technique, and shooting technique.

If the monitored object 104 is a soccer ball, the change in the spatial orientation of the ball resulting from the kick may be used to determine, for example, a launch angle of the ball, a rate of rotation of the ball, launch speed, estimated speed, or similar metrics. If the monitored object 104 is the chest of an individual 100 playing basketball, the change in the spatial orientation of the individual's 100 chest during the one-hundred and eighty degree rotation may be used to determine, for example, that the individual had been posting up a defender and then executed a one-hundred and eighty degree spin move to maneuver around the defender, or similar metrics. In other embodiments, the change in the spatial orientation of the individual's 100 chest may be used to determine a jump height or jump force.

Finally, at step 412, an output is provided that conveys the activity metric to the individual 100, a coach, a teammate, a spectator, or any other interested person. In one embodiment, the output may be an audible, visual, and/or haptic output.

In some embodiments of the present invention, instead of a desire to monitor changes in the spatial orientation of an object 104 of interest, there may be a desire to correlate movements of objects 104, such as the individual's 100 body 106 or the piece of the individual's 100 athletic equipment 108, to activity metrics based on a predetermined correlation stored in a data structure. A common analytical framework may be used to carry out such correlations. This analytical framework is illustrated by FIG. 13.

Figure 13:
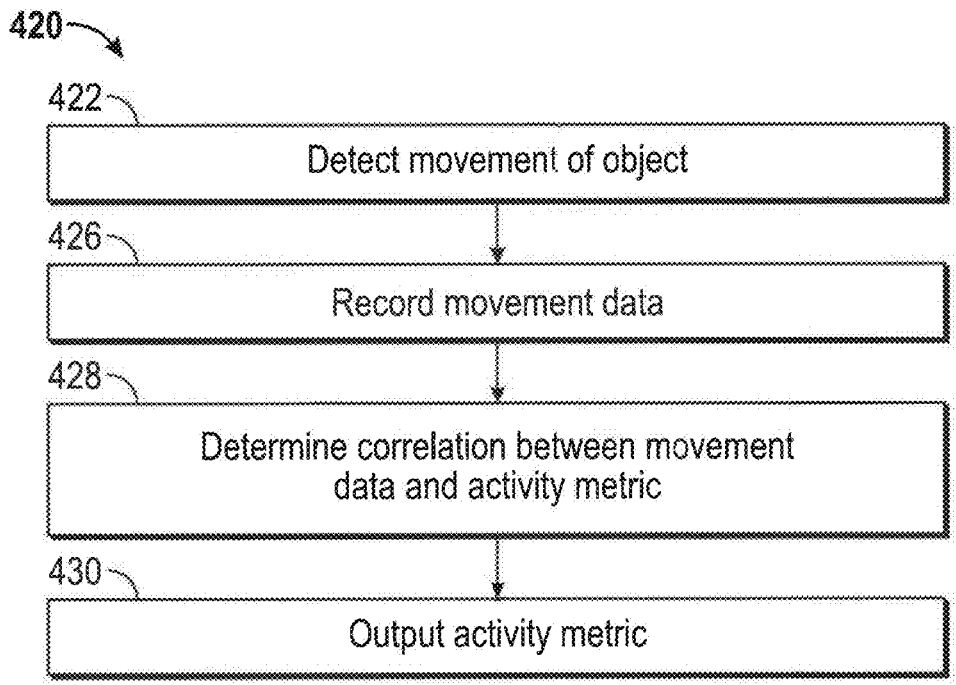
FIG. 13 is flow chart illustrating a method for determining an activity metric according to an embodiment of the present invention.

With reference to FIG. 13, in such an embodiment, the individual 100 may use the sensor module 102 in the athletic activity monitoring system 10 to determine such correlations to object 104 movement according to movement correlation process 420 as follows.

First, at step 422, the sensor module 102 may detect movement of the object 104. This step may be carried out in a similar fashion to step 402 of the spatial orientation process 400, as described above.

If the monitored object 104 is a soccer ball, the detected movement may consist of the soccer ball rolling on the ground as a result of being dribbled by the individual 100. If the monitored object 104 is the chest of an individual 100 playing basketball, the detected movement may consist of the individual's chest moving forward as the individual dribbles a basketball down the court.

In some embodiments, the sensor module 102 may then determine that the movement of the object 104 indicates the occurrence of a movement to track. This step may be carried out in a similar fashion to step 404 of the spatial orientation process 400, as described above.

If the monitored object 104 is a soccer ball, the movement of the soccer ball as a result of the individual 100 swiftly kicking the ball in an attempt to make a goal may result in a determination that the motion of the ball in response to the kick—which could include motion of the ball before, during, and/or after the determination was made—should be tracked. If the monitored object 104 is the chest of an individual 100 playing basketball, the movement of the individual's 100 chest sharply upward away from the ground as a result of the individual jumping to, for example, take a jump shot, attempt a dunk, or attempt to block a shot, may result in a determination that the upward movement of the individual's chest—which could include motion of the individual's 100 chest before, during, and/or after the determination was made—should be tracked.

Next, at step 426, the sensor module 102 may record movement data in response to identifying a movement to track. In one embodiment, movement of the object 104 is recorded based on acceleration data captured by the acceleration sensor 116 of the sensor module 102. In another embodiment, movement of the object 104 is recorded based on magnetic field data captured by the magnetic field sensor 118 of the sensor module 102. In yet another embodiment, movement of the object 104 is recorded based on both acceleration data and magnetic field data.

If the monitored object 104 is a soccer ball, the movement of the soccer ball as a result of the individual 100 swiftly kicking the ball may be recorded. If the monitored object 104 is the chest of an individual 100 playing basketball, the movement of the individual's 100 chest sharply upward may be recorded.

Next, at step 428, the sensor module 102 may determine a correlation between the recorded movement data and an activity metric. In one embodiment, this determination may be based on correlation information stored in a data structure, such as a lookup table.

A lookup table is a data structure, usually an array or associative array, often used to replace a runtime computation with a simpler array indexing operation. The savings in terms of processing time can be significant, since retrieving a value from memory is often faster than undergoing relatively processing-expensive computation or input/output operation. Lookup table figures may be pre-calculated and stored in static program storage or pre-fetched as part of a program initialization phase.

The nature of the correlation may depend on the particular application and algorithms used to establish the correlation. Also, the nature of the activity metric may change based on the athletic activity that the individual 100 is participating in, as well as particular object 104 that is being monitored. In one embodiment, the activity metric may relate to, for example, a launch angle, a rate of rotation, a speed, a jump height, a jump force, a characterization of a specific type of athletic movement, or a reaction time measurement. In other embodiments, the activity metric may be, for example, the rate of rotation, the plane of rotation, the jump force, force profile (force acting upon the body of the athlete or the ground or the object), stroke information in tennis, swing profile in golf, baseball, hockey stick, kick profile of a leg, angle position of a bike pedal, power output of a cyclist, fatigue (tremors starting to occur in repeated motion, i.e., running, lifting swimming, rowing etc.), posture, throwing or arm swing technique, and shooting technique.

If the monitored object 104 is a soccer ball, the correlation between the recorded movement data and an activity metric may rely on correlation data stored in a data structure that was derived from a function that expresses a relationship between soccer ball acceleration data and soccer ball launch speed metrics. In some embodiments, the function underlying the relationship between soccer ball acceleration data and soccer ball launch speed may be based on empirical data for the specific model soccer ball.

If the monitored object 104 is the chest of an individual 100 playing basketball, the correlation between the recorded movement data and an activity metric may rely correlation data stored in a data structure that was derived from a function that expresses a relationship between chest acceleration data and, for example, jump height or jump force metrics. In some embodiments, the function underlying the relationship between chest acceleration data and jump height may be based on data such as, for example, the individual's weight.

Finally, at step 430, an output is provided that conveys the activity metric to the individual 100, a coach, a teammate, a spectator, or any other interested person. This step may be carried out in a similar fashion to step 412 of the spatial orientation process 400, as described above.

The analytical frameworks outlined with respect to FIG. 12 and FIG. 13 detailing the basic spatial orientation process 400 and the basic movement correlation process 420, respectively may be used in embodiments of the present invention to monitor the individual's 100 body 106 or a piece of the individual's 100 athletic equipment 108 using a sensor module 102. However, in some embodiments of the present invention, these basic analytical frameworks may include additional steps that may provide improved capabilities, thus offering the individual 100 engaged in athletic activities better tools to assess their activities.

Figure 14:
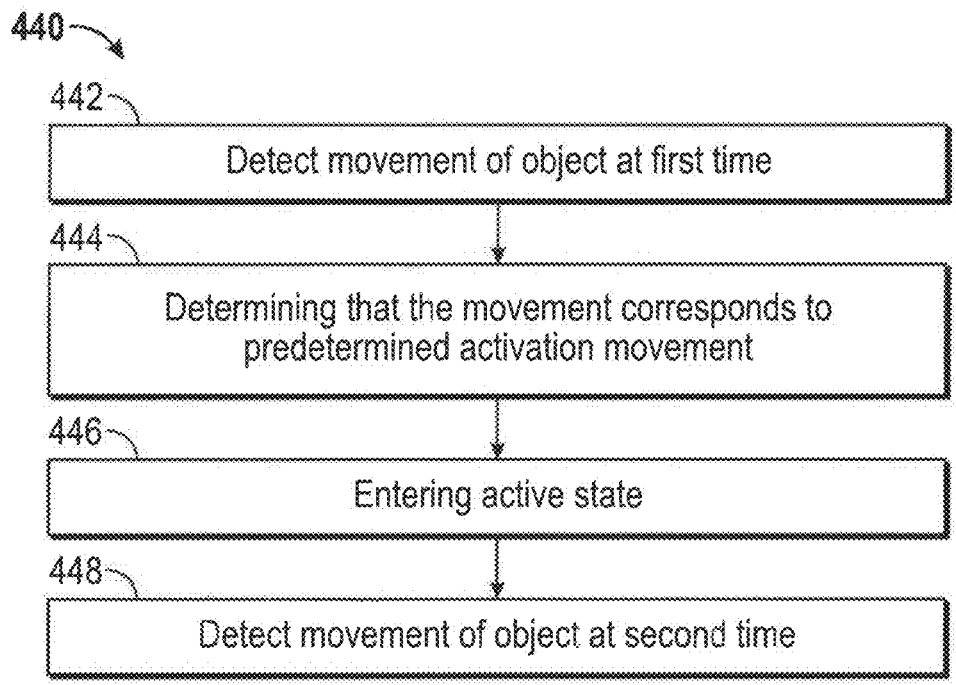
FIG. 14 is flow chart illustrating a method for activating a sensor module according to an embodiment of the present invention.

FIG. 14 illustrates an active state process 440 that may be used to augment the basic spatial orientation process 400 or the basic movement correlation process 420 outlined above. The active state process 400 may enable a sensor module 102 to run in a plurality of states, one of which may be considered an active state. In one embodiment, the active state may be characterized by the sensor module 102 consuming more power during the active state than prior to the active state. In another embodiment, the active state may be characterized by the sensor module 102 sampling data from the acceleration sensor 116 at a higher rate during the active state than prior to the active state. In yet another embodiment, the active state may be characterized by the sensor module 102 permanently saving data in the active state, as opposed to only temporarily recorded data prior to the active state. In this way, enabling various states may allow the sensor module 102 to operate with reduced battery power, reduced processing power, or otherwise be more efficient.

With reference to FIG. 14, the active state process 440 begins as step 442. In one embodiment, the steps of the active state process 440 may occur just prior to the steps of the basic spatial orientation process 400 or the basic movement correlation process 420 so that these processes may be carried out with more efficient sensor module 102 function.

At step 442, the sensor module 102 may detect movement of the object 104 at a first time. This step may be carried out in a similar fashion to step 402 of the spatial orientation process 400 or step 422 of the movement correlation process 420, as described above.

If the monitored object 104 is a soccer ball, the detected movement may consist of the soccer ball rolling on the ground as a result of being dribbled by the individual 100. If the monitored object 104 is the chest of an individual 100 playing basketball, the detected movement may consist of the individual's 100 chest moving forward as the individual dribbles a basketball down the court.

Next, at step 444, the sensor module 102 may determine that the movement of the object 104 corresponds to a predetermined activation movement. In some embodiments, the predetermined activation movement may include a series of discrete movements such as, for example, a ball being bounced three times in series, the ball being thrown a predetermined height, the ball being kicked with a certain level of force, the individual 100 jumping up and down three times in series, or a movement that results in the acceleration of the sensor module 102 exceeding and/or falling below a predetermined threshold in absolute terms or for a predetermined period of time. In one embodiment, movement of the object 104 is detected based on acceleration data captured by the acceleration sensor 116 of the sensor module 102. In another embodiment, movement of the object 104 is detected based on magnetic field data captured by the magnetic field sensor 118 of the sensor module 102. In yet another embodiment, movement of the object 104 is detected based on both acceleration data and magnetic field data.

The step of determining that the movement of the object corresponds to a predetermined activation movement may include comparing acceleration data associated with the predetermined activation movement to acceleration data detected in association with the movement of the object. Alternatively, the step of determining that the movement of the object corresponds to a predetermined activation movement may include comparing timing data associated with the predetermined activation movement to timing data detected in association with the movement of the object.

If the monitored object 104 is a soccer ball, the predetermined activation movement could be, for example, movement of the soccer ball after it had been stationary for a predetermined period of time, the soccer ball being bounced three times, the soccer ball being thrown into the air a certain height of period of time, or a variety of other possible activation movements. If the monitored object 104 is the chest of an individual 100 playing basketball, the predetermined activation movement could be, for example, movement of the individual's 100 chest after the individual 100 had been stationary for a predetermined period of time (e.g., sitting on the bench), the individual 100 jumping up and down three times in a row, the individual 100 squatting three times in a row, or a variety of other possible activation movements.

In some embodiments, the monitored object 104 can be considered stationary when the sensor module 102 of the monitored object 104 senses resultant acceleration of about 1G (i.e., resultant acceleration within a threshold tolerance of 1G, for example, within 5% of 1G). In some embodiments the monitored object 104 can be considered stationary at times while being handled by an individual. For example, a ball can be stationary for a period of time within a period of time in which a basketball player takes a jump shot with ball (e.g., before release of ball from the hands of the individual, ball can be considered stationary, where resultant acceleration sensed by sensor module 102 is about 1G). Also for example, the ball can be stationary for a period of time within a period of time in which a baseball player performs a throw of ball (e.g., a period of time spanning the transition from rearward motion to forward motion of the individual's throwing motion, where resultant acceleration sensed by sensor module 102 is about 1G).

Next, at step 446, after determining that an activation movement has occurred, the sensor module 102 may enter the active state. As previously described, the active state may be characterized, for example, by the sensor module 102 consuming more power or sampling data at a higher rate during the active state than prior to the active state.

Finally, at step 448, upon the sensor module 102 entering the active state, detection of movement of the object at a second time, as detailed at step 402 of the basic spatial orientation process 400 or at step 422 of the basic movement correlation process 420. In this way, enabling various states may allow the sensor module 102 to operate with reduced battery power, reduced processing power, or otherwise be more efficient.

Figure 15:
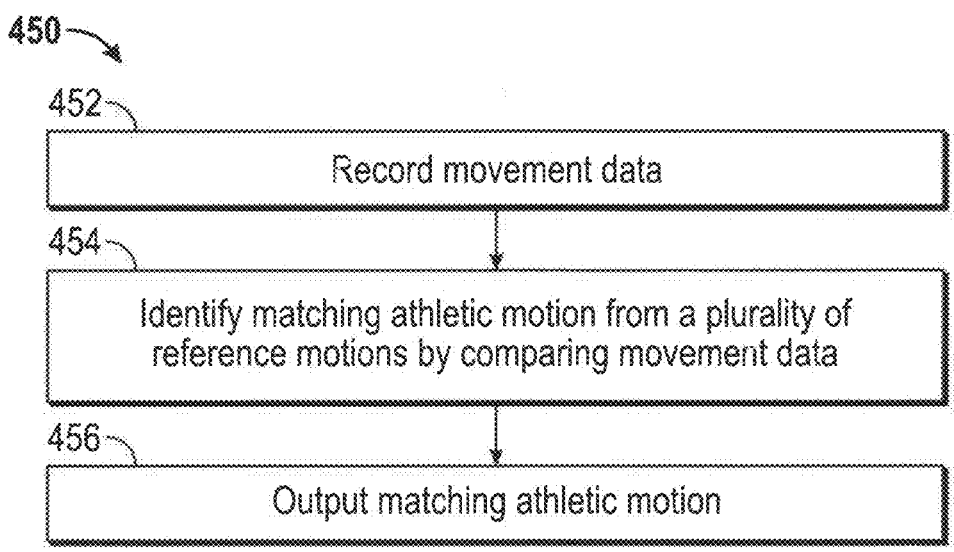
FIG. 15 is flow chart illustrating a method for identifying a matching athletic motion according to an embodiment of the present invention.

FIG. 15 illustrates a reference motion process 450 that may be used to augment the basic movement correlation process 420 outlined above. The reference motion process 450 may enable a sensor module 102 to identify a matching athletic motion from a plurality of reference motions by comparing movement data, where the plurality of reference motions may be diverse in nature. In this way, the athletic motion identification capabilities of the movement correlation process 420 may be enhanced by enabling identification and tracking of diverse types of motions executed during an activity.

With reference to FIG. 15, the reference motion process 450 begins as step 452. In one embodiment, the steps of the reference motion process 450 may effectively be substituted for step 426, 428, and 430 of the basic movement correlation process 420 outlined above so that the correlation and identification capabilities are enhanced.

At step 452, the sensor module 102 may record movement data (possibly in response to identifying a movement to track in a previous step, as outlined above). In one embodiment, movement of the object 104 is recorded based on acceleration data captured by the acceleration sensor 116 of the sensor module 102. In another embodiment, movement of the object 104 is recorded based on magnetic field data captured by the magnetic field sensor 118 of the sensor module 102. In yet another embodiment, movement of the object 104 is recorded based on both acceleration data and magnetic field data.

If the monitored object 104 is a soccer ball, the movement of the soccer ball as a result of the individual 100 swiftly kicking the ball may be recorded. If the monitored object 104 is the chest of an individual 100 playing basketball, the movement of the individual's 100 chest sharply upward may be recorded.

Next, at step 454, the sensor module 102 may identify a matching athletic motion from a plurality of reference motions by comparing the movement data to data associated with the plurality of reference motions. In one embodiment, as with step 428 of the basic movement correlation process 420, the identification may be made at least in part based on correlation information stored in a data structure, such as a lookup table.

Particular to step 428, identification of the matching athletic motion may be by reference to a plurality of reference motions. In other words, at step 428, the system is not limited to looking for a motion that matches a single motion (e.g., kicking a soccer ball in an effort to score a goal). In some embodiments, the system is not limited to looking for a motion that matches a single class of motions (e.g., offensive soccer motions). In other embodiments, the system is not limited to looking for a motion that matches motions in a single sport (e.g., soccer motions). Alternatively, when the activity is a team sport, the matching athletic motion may be a motion commonly executed by a person during that team sport.

In one embodiment, one or more of the reference motions may include a series of discrete movements. In some embodiments, data associated with the plurality of reference motions may include acceleration data, magnetic field data, and/or timing data. Of course, the nature of the identifying matching athletic motion may depend on the particular application and algorithms used to establish the match. Also, the nature of the matching athletic motion may change based on the athletic activity that the individual 100 is participating in, as well as particular object 104 that is being monitored. In one embodiment related to basketball, the matching athletic motion may be, for example, a pass motion, an shot motion, an jump-shot motion, a dunk motion, a post-up motion, a cross-over dribble motion, a shot blocking motion, a steal motion, or a rebound motion.

Finally, at step 456, an output is provided that conveys the matching athletic motion to the individual 100, a coach, a teammate, a spectator, or any other interested person. This step may be carried out in a similar fashion to step 430 of the movement correlation process 420, as described above. In this way, the athletic motion identification capabilities of the movement correlation process 420 may be enhanced by enabling identification and tracking of diverse types of motions executed during an activity.

Figure 16:
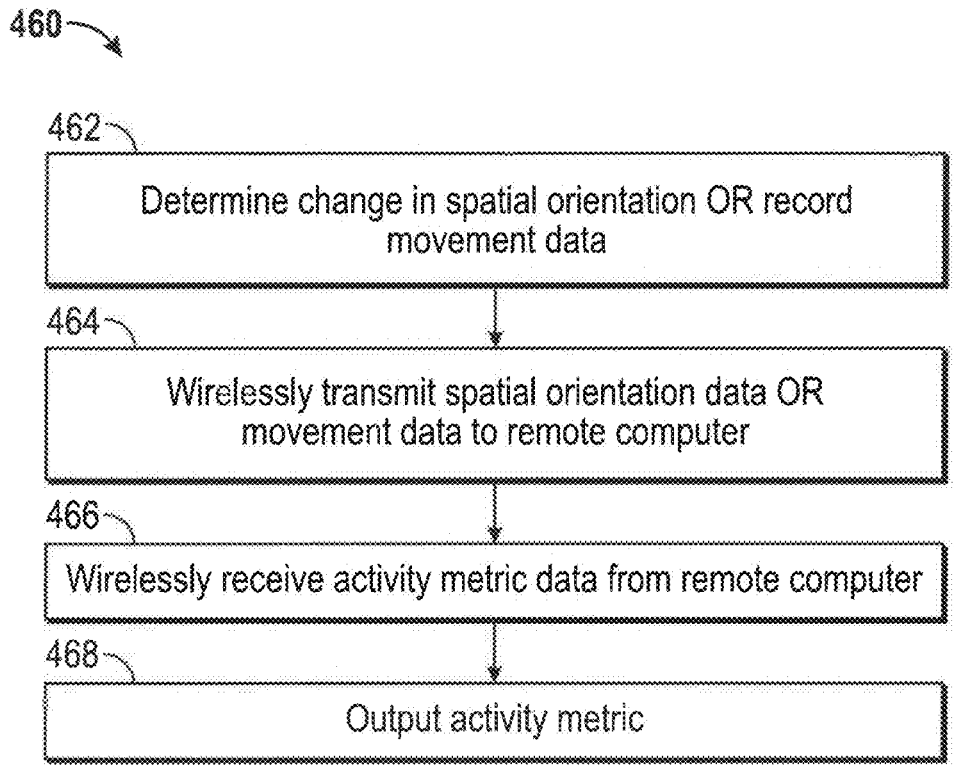
FIG. 16 is flow chart illustrating a method for communicating with a remote computer according to an embodiment of the present invention.

FIG. 16 illustrates a remote spatial processing process 460 that may be used to augment the basic spatial orientation process 400 outlined above. The remote spatial processing process 460 may enable a sensor module 102 to wirelessly transmit spatial orientation data to a remote computer for processing. Wireless communication with other elements of the athletic activity monitoring system 10 is generally described above with reference to FIG. 7. In this way, the spatial processing capabilities or movement correlation capabilities of the athletic activity monitoring system 10 may be enhanced by shifting certain processing and analytical tasks to a remotely located computer, such as a server computer, with greater computational abilities and, in some embodiments, access to additional data or other resources.

With reference to FIG. 16, the remote spatial processing or correlation process 460 begins as step 462. In one embodiment, the steps of the remote spatial processing or correlation process 460 may effectively be substituted for step 410 of the basic spatial orientation process 400, or step 426 of the basic movement correlation process 420, outlined above so that activity metric determination may occur remotely.

At step 462, a change in the spatial orientation of the object 104 may be determined or movement data may be recorded. In an embodiment, the determination of the change in the spatial orientation of the object 104 or the recordation of movement data at step 462 may be made similarly to the determination of the change in spatial orientation of the object 104 at step 408 of the basic spatial orientation process 400 outlined above or to the recording of movement data at step 426 of the basic movement correlation process 420.

Next, at step 464, the sensor module 102 may wirelessly transmit data relating to the change in spatial orientation, or to movement, to a computer, wherein the computer is remotely located from the user during the athletic activity. For example, the remote computer may be server 202. In one embodiment, the data relating to the change in spatial orientation, or to movement, may be transmitted to the remote computer during the athletic activity. In another embodiment, the data relating to the change in spatial orientation, or to movement, may be transmitted to the remote computer after the athletic activity has been completed.

Next, at step 466, the sensor module 102 may wirelessly receive activity metric data from the remote computer, wherein the activity metric data is based on the transmitted data relating to the change in spatial orientation, or to movement. Accordingly, the determination of the activity metric, as outlined, for example, at step 410 of the basic spatial orientation process 400, the determination of the activity metric based on correlation data, possibly with reference to a lookup table, as outlined, for example, at step 428 of the basic movement correlation process 420, may be handled by the remote computer. In one embodiment, the activity metric data may be received from the remote computer during the athletic activity. In another embodiment, the activity metric data may be received from the remote computer after the athletic activity has been completed.

In addition, in certain embodiments, because of the greater processing capabilities and resources of the remote computer, the remote computer may be capable of providing additional information to the sensor module 102. In one embodiment, the sensor module 102 may receive training recommendation data from the remote computer in addition to the activity metric data. In another embodiment, the sensor module 102 may receive motivational content data from the remote computer in addition to the activity metric data.

In an embodiment, the activity metric data received from the remote computer may include a comparison between data associated with the user for the present athletic activity and data associated with the user from a previous athletic activity. In another embodiment, the activity metric data received from the remote computer may include a comparison between data associated with the user for the present athletic activity and data associated with a different individual's athletic activity.

Finally, at step 468, an output is provided that conveys the activity metric to the individual 100, a coach, a teammate, a spectator, or any other interested person. This step may be carried out in a similar fashion to step 412 of the spatial orientation process 400, or to step 430 of the movement correlation process 420, as described above. In this way, the spatial processing or movement determining capabilities of the athletic activity monitoring system 10 may be enhanced by shifting certain processing and analytical tasks to a remotely located computer, such as a server computer, with greater computational abilities and, in some embodiments, access to additional data or other resources.

Figure 17:
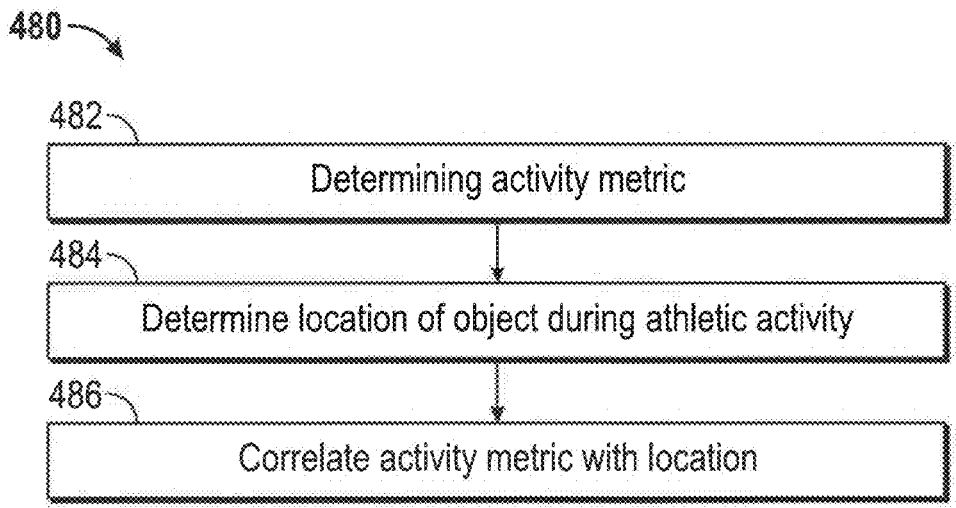
FIG. 17 is flow chart illustrating a method for correlating an activity metric with a location according to an embodiment of the present invention.

FIG. 17 illustrates a location process 480 that may be used to augment the basic spatial orientation process 400 or the basic movement correlation process 420 outlined above. The location process 480 may enable an individual to determine the precise geographic location that various monitored athletic motions occurred during the course of an athletic activity. In this way, the location process 480 may provide the individual, a coach, a teammate, a spectator, or any other interested person with additional information that may be correlated with the movement-based activity metric information itself.

With reference to FIG. 17, the location process 480 begins as step 482. In one embodiment, the steps of the location process 480 may occur after the steps of the basic spatial orientation process 400 or the basic movement correlation process 420, or just prior to the output steps of these processes.

At step 482, the activity metric may be determined based on a change in the spatial orientation of the object 104, as described at step 410 of the spatial orientation process 400, or based on the correlation described at step 428 of the movement correlation process 420. The nature of the activity metric may change based on the athletic activity that the individual 100 is participating in, as well as particular object 104 that is being monitored. In one embodiment, the activity metric may relate to, for example, a launch angle, a rate of rotation, a speed, a jump height, jump force, a characterization of a specific type of athletic movement, or a reaction time measurement.

Next, at step 484, the location of the object 104 during the athletic activity may be determined. In one embodiment, the location of the object 104 during the athletic activity is determined using a satellite positioning system receiver, such as a GPS, Galileo, BeiDou, or GLONASS receiver. In another embodiment, the location of the object 104 during the athletic activity is determined using a beacon signal or radio signal triangulation.

In embodiments where the individual's 100 physical activity includes traversing a specific route (e.g., running or biking in a race), the sensor module 102 may capable of recording an individual's 100 geographic way points along the route traversed.

Finally, at step 486, a determined athletic activity metric may be correlated with the location associated with the athletic activity metric. Accordingly, for example, the sensor module 102 may capable of recording where an individual 100 took each soccer or basketball shot.

By using the athletic activity monitoring system 10 including the sensor module 102 described above, embodiments of the present invention may advantageously enable the individual 100 (or their coach, teammate, or a spectator) to obtain this or other information about the motion of the individual's 100 body 106 or the motion of a piece of the individual's 100 athletic equipment 108 during or after the course of the athletic activity.

While various embodiments of the present invention are described in the context of the sports of soccer (i.e., football) and basketball, the present invention is not so limited and may be applied in a variety of different sports or athletic activities including, for example, baseball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto.

For baseball, sensor module 102 embodiments such as those described above may enable an individual 100, coach, teammate, or a spectator to determine, for example, characteristics of a pitcher's pitch, a batter's swing, or the ball's movement after it is hit. For example, a sensor module 102 could be used to determine the type of pitch thrown (fastball, curveball, slider, change-up, etc.), the speed of a pitch, or the total pitch count. A sensor module 102 could also be used to determine the type of swing (e.g., regular swing, bunt, swing that connects with the ball, swing that misses the ball, etc.), the speed of the swing, or the swing count, or the type of hit (grounder, line-drive, fly ball, homerun, etc.). In some embodiments the sensor module 102 may be mounted, for example, on a pitcher's torso, arm, hand, or finger, on a batter's torso, arm, hand, or finger, on the ball, or on a bat.

For bowling, sensor module 102 embodiments such as those described above may enable an individual 100, coach, teammate, or a spectator to determine, for example, characteristics of a bowler's release or the ball's path. For example, a sensor module 102 could be used to determine the type of spin applied to the roll, the speed of a roll, or the total roll count. A sensor module 102 could also be used to determine the path of the ball after a release. In some embodiments the sensor module 102 may be mounted, for example, on a bowler's torso, arm, hand, or finger, or on the ball.

For boxing, sensor module 102 embodiments such as those described above may enable an individual 100, coach, teammate, or a spectator to determine, for example, characteristics of a boxer's offensive or defensive moves. For example, a sensor module 102 could be used to determine the type of punch thrown by a boxer (jab, hook, upper-cut, etc.), whether the boxer's left or right hand was used, the speed of the punch, whether the punch connected, and/or the total punch count. A sensor module 102 could also be used to determine whether a boxer dogged left, right or down, blocked a punch, was knocked down, or how many punches the boxer took. In some embodiments the sensor module 102 may be mounted, for example, on a boxer's torso, arm, hand, or finger, or on their boxing glove.

For cycling, sensor module 102 embodiments such as those described above may enable an individual 100, coach, teammate, or a spectator to determine, for example, characteristics of a biker's or bike's motion. For example, a sensor module 102 could be used to determine the speed of the bike, the nature of the turns, or the nature of the elevation changes during a route. In some embodiments the sensor module 102 may be mounted, for example, on a biker's torso, arm, hand, leg, foot, or head, or on their bike.

For football (i.e., American football), sensor module 102 embodiments such as those described above may enable an individual 100, coach, teammate, or a spectator to determine, for example, characteristics of an offensive, defensive, or special teams player's movements, or the movement of the ball itself. For example, a sensor module 102 could be used to determine the type of run, pass, kick, or tackle, the number or runs, passes, kicks, or tackles, the force or a run, pass, kick, or tackle, the type of move used by a running back (e.g., spin move, stiff arm, hurdle, dive, sprint, etc.), or the distance, hang time, or rotational characteristics of a pass or kick. In some embodiments the sensor module 102 may be mounted, for example, on a player's torso, arm, or leg, or on the ball.

For golf, sensor module 102 embodiments such as those described above may enable an individual 100, coach, teammate, or a spectator to determine, for example, characteristics of a golfer's swing or the motion of the ball after it is hit. For example, a sensor module 102 could be used to determine the type of swing (drive, fairway shot, approach shot, putt) the swing speed, the swing quality, or a swing count. A sensor module 102 could also be used to determine the path of the ball (straight, slice, hook, low, high, breaking left, breaking right) or the distance of a shot. In some embodiments the sensor module 102 may be mounted, for example, on a golfer's torso, arm, hand, leg, foot, or head, or on the ball, or on a club.

For hockey, sensor module 102 embodiments such as those described above may enable an individual 100, coach, teammate, or a spectator to determine, for example, characteristics of a player's shot or pass or the motion of the puck after it is contacted. For example, a sensor module 102 could be used to determine the type of shot (e.g., slapshot, backhand shot), the shot speed, the shot quality, or a shot or pass count. A sensor module 102 could also be used to determine the path of the puck toward the goal (straight, left, right, low, high,). In some embodiments the sensor module 102 may be mounted, for example, on a hockey player's torso, arm, hand, leg, foot, or head, or on the puck, or on a stick.

For running, sensor module 102 embodiments such as those described above may enable an individual 100, coach, teammate, or a spectator to determine, for example, characteristics of a runner's motion. For example, a sensor module 102 could be used to determine the speed, pace, distance traversed, locations traversed, or the nature of the elevation changes during a route. In some embodiments the sensor module 102 may be mounted, for example, on a runner's torso, arm, hand, leg, foot, or head, or on their article of footwear.

For skiing, sensor module 102 embodiments such as those described above may enable an individual 100, coach, teammate, or a spectator to determine, for example, race-course statistics or information on when certain tricks are successfully performed. For example, a sensor module 102 could be used to determine how many gates a skier successfully traverse on a race course, the skier's speed, or the angles of their turns. Also, a sensor module 102 could be used to determine maneuvers such as jumps, flips, rotations, or the degree of the actions that makeup the maneuvers (e.g., height of jump, degrees of rotation, hang-time, etc.). In one embodiment, sensor module 102 may be mounted on a top or bottom surface of a ski, contained within a ski, or placed in a void in the ski, in a releasable or non-releasable manner, or mounted to the skier's boot, body, or other clothing.

For tennis, sensor module 102 embodiments such as those described above may enable an individual 100, coach, teammate, or a spectator to determine, for example, characteristics of a player's swing or the motion of the ball after it is hit. For example, a sensor module 102 could be used to determine the type of swing (forehand, backhand, serve, return, lob) the swing speed, the swing quality, or a swing count. A sensor module 102 could also be used to determine the motion of the ball (straight, topspin, backspin, left spin, right spin) or the distance of a shot. In some embodiments the sensor module 102 may be mounted, for example, on a player's torso, arm, hand, leg, foot, or head, or on the tennis ball, or on a racquet.

For skateboarding, sensor module 102 embodiments such as those described above may enable an individual 100, coach, teammate, or a spectator to determine, for example, when certain tricks are successfully performed, such as ollies, aerials, flip tricks (e.g., kickslips), slides, or grinds, or the degree of the actions that makeup the tricks (e.g., height of jump, rate of rotation, length of time of slide, etc.). In one embodiment, the sensor module 102 may be mounted on the underside of the skateboard, in a void between a skateboard wheel axle (i.e., truck) and the skateboard itself. In other embodiments, the sensor module 102 may be coupled to a top or bottom surface of the board, contained within the board, or coupled to a wheel axle (i.e., truck) in a releasable or non-releasable manner.

For surfing, sensor module 102 embodiments such as those described above may enable an individual 100, coach, teammate, or a spectator to determine, for example, when certain maneuvers are successfully performed, such as, for example, riding waves, executing turns or cutbacks, carving, floating, or tube riding. In one embodiment, the sensor module 102 may be mounted on a top or bottom surface of the surfboard, contained within the surfboard, or placed in a void in the surfboard, in a releasable or non-releasable manner.

In another embodiment of the present invention, sensor module 102 embodiments such as those described above may enable an individual 100, coach, teammate, or a spectator to analyze the individual's 100 strength and flexibility workout movements or exercises. For example, in one embodiment, an individual 100 or a piece of athletic equipment 108 used by the individual 100 during strength and flexibility workouts may carry a sensor module 102 that is capable of tracking, for example, sit-ups, push-ups, lunges, jumping-jacks, pull-ups, squats, dips, and/or calf raises. The sensor module 102 may be capable of being used to determine whether these movements are being done correctly and/or how many repetitions of each movement were conducted.

In some embodiments of the present invention, the sensor module 102 may be capable of compensating for inherent deficiencies that may be present for various types of sensor contained within or in communication with the sensor module 102. Most real world sensors have limitations. For example, accelerometers, magnetometers, and gyroscopes may have accuracy issues, particularly when used at speeds or under other conditions that differ from their initial calibration conditions.

In some systems, if sensor data, such as acceleration sensor 116 or magnetic field sensor 118 data, is temporarily lost or otherwise unavailable, the data from the unavailable sensor is not used in subsequent processing or calculations. In other systems, lost data may be estimated by "straight line" methods where, for example, it is assumed that the data stays constant or changes at a constant rate. However, in some embodiments of the present invention sensor data, such as one of acceleration sensor 116 or magnetic field sensor 118 data may be used to compensate for and/or estimate the changes in the other of acceleration sensor 116 or magnetic field sensor 118 data based on known, derived, or estimate correlations between the two types of data, or data extrapolation.

By combining the data produced by, for example, acceleration sensor 116 and a magnetic field sensor 118, systems and methods according to embodiments of the present invention are able to more accurately determine absolute data values or activity metrics even when data from one of the acceleration sensor 116 or the magnetic field sensor 118 is lost for any reason. Using the data that is not missing, the system can continue to provide data values or activity metrics to fill in the "holes" until the missing data is regained or otherwise again sampled.

In other embodiments of the present invention, angular momentum sensor 124 data, such as gyroscope data, may be used in combination with one or more of acceleration sensor 116 or magnetic field sensor 118 data for data calibration and/or extrapolation.

In some embodiments of the present invention, calibration and/or generation of correction factor data for an acceleration sensor 116 or magnetic field sensor 118-based sensor modules 102 may be performed under a variety of different use conditions, e.g., calibration data or correction factors may be generated for use at different movement speeds, for use with an individual's 100 body 106, with a piece of athletic equipment 108, for use in different sports, for use under different wind conditions, for use under different court or field conditions, etc. Moreover, this variety of correction factors and/or calibration data may be collected, in the background, over time, as the individual 100 continues using the system. In this manner, a "lookup table" or other "universe" or library of calibration data or correction factors may be built up and stored in the monitoring system (optionally in the portable portion of the system), such that an appropriate correction factor could be generated and applied for a full range of individual 100 or athletic equipment 108 speeds and/or other use conditions.

A microprocessor provided with the system (optionally in the portable portion of the system, in the personal computer, etc.) may be programmed to interpolate between and/or extrapolate from known calibration or correction factors to arrive at the most appropriate calibration or correction factor for use at any speed or other use condition(s). Also, in this manner, different calibration or correction factors may be applied at different times during a single athletic performance, e.g., based on the speed or other use conditions determined at a given time during the performance, to further help improve the overall accuracy of the speed and distance monitor. By having a variety of correction or calibration factors available under different performance conditions, the sensor module 102 will tend to become more accurate, particularly over time and with increased use, because of the increased number of calibration and correction factors generated with increased use.

In one embodiment of the present invention, the sensor module 102 may be affected by perturbations in local magnetic fields, such as the earth's magnetic field. The local magnetic field may be more variable at certain distances near the surface of the earth than at other distances further away from the earth. For example, the local magnetic field may be more variable or perturbed within approximately three feet of the surface of the earth than at more than approximately three feet away from the surface of the earth. Accordingly, in some embodiments, magnetic field sensor 118 data obtained from an object 104 when the object 104 is more than approximately three feet away from the surface of the earth may be used to extrapolate or otherwise estimate proper or likely magnetic field sensor 118 data from when the object 104 was within approximately three feet of the surface of the earth, if the magnetic field sensor 118 data from when the object 104 was within approximately three feet of the surface of the earth is otherwise deemed to be unreliable due to the relatively high variability in local magnetic fields, such as the earth's magnetic field, near the surface of the earth.

In some embodiments, sensor module 102 of monitoring system 10 can be mounted to an individual 100. In some embodiments, multiple sensor modules 102 can be mounted to individual 100 (e.g., one sensor module having axes at one or more oblique angles to another sensor module). In some embodiments, sensor modules 102 may be mounted to individual 100 at different locations (e.g., on the trunk of individual 100, on one or more appendages of individual 100). For example, individual 100 may be an athlete performing an athletic activity. Monitoring system 10 including sensor module 102 mounted to individual 100 is referred to as monitoring system 30. Sensor module 102 can be mounted to individual 100 using any suitable technique. For example, sensor module 102 may be worn by individual 100 by being coupled to an exterior or interior of individual 100, by being mounted to individual 100 using a harness system worn by individual 100, by being carried in a pocket of a garment worn by individual 100, by being affixed to the skin of individual 100 (e.g., using adhesive), by being carried by an article of equipment carried or worn by individual 100 (e.g., a helmet, a mouth guard, a jock strap, a protective pad, an article of footwear), or by being inserted within the body of individual 100 (e.g., surgically, orally). Exemplary techniques that can be employed to mount sensor module 102 to individual 100 are described in commonly owned U.S.

patent application Ser. No. 13/077,520, filed Mar. 31, 2011, the entirety of which is incorporated herein by reference in its entirety.

In some embodiments, sensor module 102 can be activated (i.e., enter an active state) in response to sensing an activation motion or movement of individual 100 (the terms "motion" and "movement" are used interchangeably herein). In some embodiments, the activation motion may be, for example, jumping above a predetermined height, jumping a predetermined number of times in within a predetermined period, walking a predetermined number of steps. In some embodiments, the activation motion may be, for example, a sequence of motions (e.g., motion in response to three jumps performed in quick succession, or within a predetermined time period such as, for example, 3 seconds). Upon activation, sensor module 102 begins to store (e.g., in memory 114) and/or transfer sensed data to a remote device, as described herein. In some embodiments, in an active state, sensor module 102 may continuously sense data (e.g., acceleration data (data representative of acceleration) is determined by acceleration sensor 116 of sensor module 102, and magnetic field data (data representative of a magnetic field) is determined by magnetic field sensor 118 of sensor module 102). In some embodiments, data is sensed by sensor module 102 periodically (e.g., every 50 milliseconds (ms), every 10 ms, every 1 ms).

In some embodiments, sensor module 102 can be deactivated (e.g., enter a low-power standby state, detecting acceleration at a low frequency relative to the active state) in response to sensing no motion of sensor module 102 for a predetermined period of time (e.g., 30 minutes). In some embodiments, sensor module 102 can be deactivated in response to sensing a deactivation motion individual 100. In some embodiments, the deactivation motion may be, for example, any of the motions described above as an activation motion. In some embodiments, a deactivation motion may be the same as an activation motion. In some embodiments, a deactivation motion may be different from an activation motion.

In some embodiments, data sensed by sensor module 102 may be time-correlated (e.g., stored in association with time data representing the time at which the data was sensed). The time at which data is sensed can be provided via timer 134. In operation, sensor module 102 of monitoring system 30 senses and processes signals as described herein to output representations of activity metrics of individual 100. In some embodiments, representations of activity metrics can be output to, for example, a display device (e.g., a display of personal computer 204, portable electronic device 206, or sensor module 102). Sensor module 102 can be powered by any suitable technique, including those described herein.

In some embodiments, monitoring system 30 including sensor module 102 mounted to individual 100 can be used to determine a variety of activity metrics about individual 100, including characteristics relating to motion of individual 100. For example, monitoring system 30 can be used to identify a motion characteristic of individual 100 (e.g., position of individual 100 or a portion thereof, orientation of individual 100 or a portion thereof, orientation and/or magnitude of speed of individual 100 or a portion thereof, orientation and/or magnitude of acceleration of individual 100 or a portion thereof, orientation and/or magnitude of forces applied to individual 100 or a portion thereof, duration of movement of individual 100 or a portion thereof, posture of individual 100 or a portion thereof, and/or rotation of individual 100 or a portion thereof); to identify a motion made by individual 100; to determine a jump characteristic of individual 100 (e.g., maximum jump height, jump force); or to determine reaction time of individual 100 (e.g., time to perform an instructed motion after being instructed, or time to reach a target, for example, to reach maximum speed, to reach a fully erect position from a crouch, to dive from an upright position). In some embodiments, monitoring system 30 can be used to define a motion. For example, monitoring system 30 can be used to define a motion made by individual 100 in terms of data sensed by sensor module 102 during performance of the motion. Monitoring system 30 can perform operations as described herein to determine such activity metrics using any suitable components. For example, sensing operations, as described, may be carried out by a sensor of sensor module 102 of monitoring system 30 (e.g., acceleration sensor 116 or magnetic field sensor 118, as appropriate). Also for example, operations involving processing of data (e.g., identifying, determining, calculating, storing) may be carried out by processor 110 of sensor module 102, or by a processor of any other device of or in communication with monitoring system 30 (e.g., server 202, personal computer 204, or portable electronic device 206).

In some embodiments, calibration data is sensed by sensor module 102 when individual 100 (or at least sensor module 102) is in a calibration state. In some embodiments, sensor module 102 is in a calibration state when sensor module 102 is stationary (e.g., with respect to an external coordinate system (i.e., a coordinate system independent of sensor module 102), such as, for example, coordinate system 600 (depicted in FIG. 18), for a period of time (e.g., 10 ms or longer)). In some embodiments, sensor module 102 can be considered stationary when sensor module 102 senses resultant acceleration of about 1G (i.e., resultant acceleration within a threshold tolerance of 1G, for example, within 5% of 1G). In some embodiments sensor module 102 can be considered stationary at times while individual is performing a movement. For example, sensor module 102 can be stationary for a period of time within a period of time in which a basketball player jumps (e.g., a period of time connecting spanning the transition from downward motion of individual 100 while bending to initiation the jump, to upward motion of individual 100 to begin launch of the jump, sensor module 102 can be considered stationary, where resultant acceleration sensed by sensor module 102 is about 1G). Also for example, sensor module 102 can be stationary due to its location on individual 100, though individual 100 is performing a motion (e.g., a sensor module 102 connected to the foot of individual 100 may be considered stationary each time the foot is planted during a running movement of individual 100, where resultant acceleration sensed by sensor module 102 is about 1G).

Figure 18:
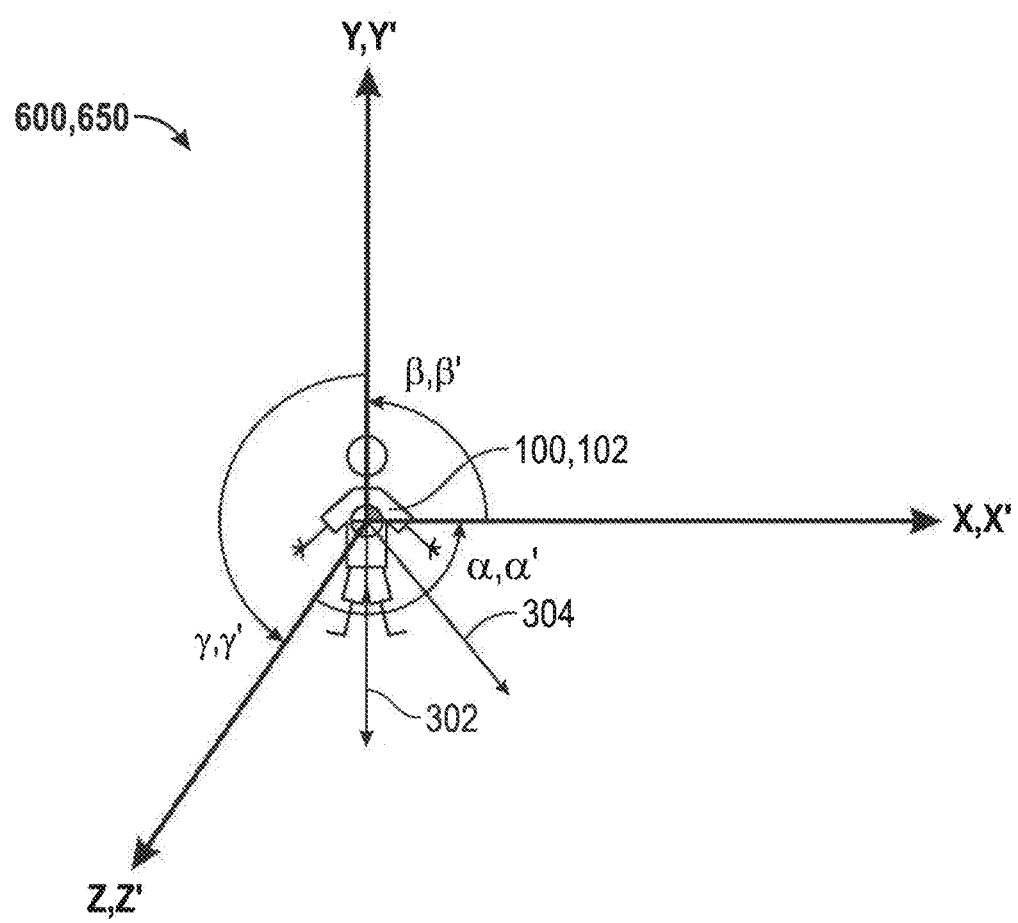
FIG. 18 is an illustration of an individual in a calibration state, according to an embodiment of the present invention.

Sensor module 102 is depicted in the calibration state in FIG. 18. Sensor module 102 may be in the calibration state at any point relative to an athletic activity (e.g., before, during, or after an athletic activity). In some embodiments, sensor module 102 is determined to be in a calibration state, and calibration data can be sensed, each time sensor module 102 is stationary. In some embodiments, sensor module 102 is determined to be in a calibration state, and calibration data can be sensed, each time sensor module 102 is stationary for more than a threshold duration (e.g., 1 second) where calibration data has not been sensed for a threshold duration (e.g., 1 minute, 10 minutes, 30 minutes).

In some embodiments, in the calibration state acceleration sensor 116 of sensor module 102 senses acceleration data. In some embodiments magnetic field sensor 118 of sensor module 102 senses magnetic field data (e.g., data relating to the magnetic field of the Earth). In some embodiments, calibration data includes both acceleration data and magnetic field data. In some embodiments, calibration data includes one of acceleration data and magnetic field data.

In some embodiments, in the calibration state, the acceleration data sensed by acceleration sensor 116 of sensor module 102 is acceleration due to gravity, which can be used by monitoring system 30 to determine one or both of orientation of acceleration due to gravity with respect to sensor module 102 and magnitude of acceleration due to gravity at sensor module 102 (together, gravity vector 302).

In some embodiments, in the calibration state, magnetic field sensor 118 of sensor module 102 senses one or both of orientation of a magnetic field with respect to sensor module 102 and magnitude of the magnetic field at sensor module 102 (together, magnetic field vector 304).

In some embodiments sensor module 102 senses calibration data that is to be relied upon for one or more subsequent calculations. In some embodiments the calibration data sensed when sensor module 102 is in the calibration state can be used to establish external coordinate system 600. In some embodiments external coordinate system 600 can be established by reference to the orientation of gravity vector 302 (e.g., to establish the direction of "down," since gravity is known to cause downward acceleration). In some embodiments external coordinate system 600 can be established by reference to the orientation of magnetic field vector 304 (e.g., to establish a constant reference direction, since the magnetic field will typically be appreciably constant over the area of a typical play area for an athletic activity). In some embodiments external coordinate system 600 can be established by reference to the orientation of gravity vector 302 and the orientation of magnetic field vector 304.

During motion, individual 100 (and sensor module 102) may move in any or all of six degrees of freedom—three linear degrees: (1) up/down (e.g., along the Y axis in external coordinate system 600), (2) left/right (e.g., along the X axis in external coordinate system 600), and (3) backward/forward (e.g., along the Z axis in external coordinate system 600); and three rotational degrees: (1) yaw (e.g., in the angular a direction in external coordinate system 600), (2) roll (e.g., in the angular β direction in external coordinate system 600), and (3) pitch (e.g., in the angular y direction in external coordinate system 600).

Individual 100 or other person may desire to know activity metrics of individual 100, for example, to learn the effects of actions of individual 100. Monitoring system 30 may determine such activity metrics (e.g., identification of forces acting on or applied by individual 100, identification of a motion made by individual 100, determination of a jump characteristic of individual 100, and determination of a reaction time of individual 100). Sensor module 102 may output data representative of such activity metrics (e.g., to a display device of personal computer 204 or portable electronic device 206). Such data may be outputted from sensor module 102 in raw form (e.g., unprocessed signals from acceleration sensor 116 and/or magnetic field sensor 118) or in representative form (e.g., data that results from processing signals from acceleration sensor 116 and/or magnetic field sensor 118). In some embodiments monitoring system 30 outputs a representation of one or more activity metrics in a manner perceivable by individual 100 and/or other person.

Data representative of such activity metrics can be processed and/or output in any suitable manner, such as, for example, those described herein.

Figure 19:
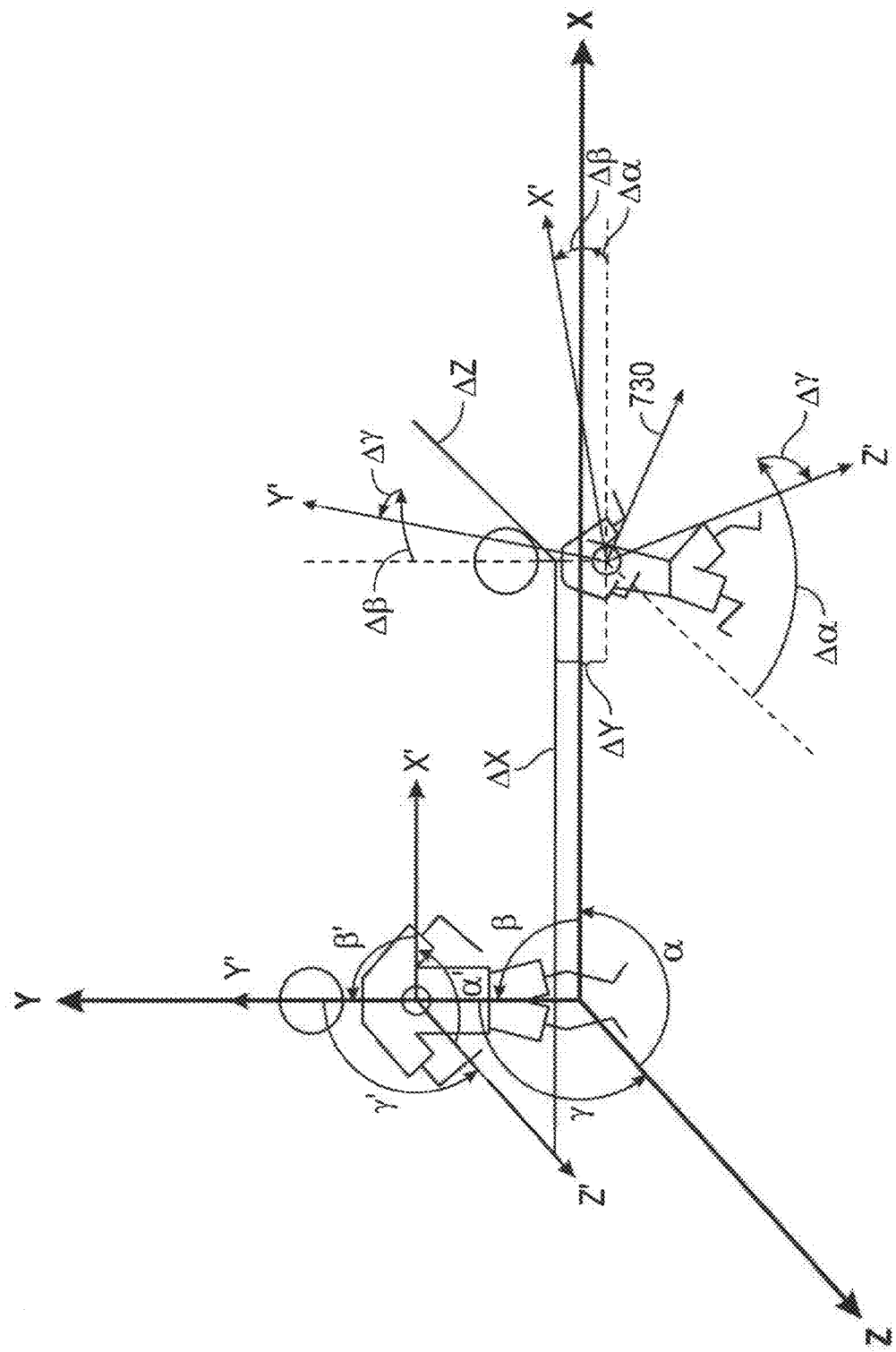
FIG. 19 is an illustration of an individual in motion, according to an embodiment of the present invention.

In some embodiments, for example, as shown in FIG. 18, an external coordinate system (e.g., external coordinate system 600) is determined at a first time (see, e.g., operation 810, FIG. 20), where sensor module 102 is in a calibration state at the first time. In some embodiments the orientation of an internal coordinate system fixed with reference to sensor module 102 (e.g., internal coordinate system 650) is determined relative to external coordinate system 600 (see, e.g., operation 812, FIG. 20). For ease of description, internal coordinate system 650 is described herein to align with external coordinate system 600 at the first time, but it should be understood that internal coordinate system 650 need not align with external coordinate system 600 (e.g., internal coordinate system 650 may be established by an angular offset from external coordinate system 600), and that internal coordinate system 600 need not be characterized by traditional coordinate components, but may be characterized simply by some reference establishing the relative orientation of sensor module 102 with respect to the external coordinate system (e.g., external coordinate system 600). Components of internal coordinate system 650 are designated in the figures as X' (e.g., left/right), Y' (e.g., up/down), Z' (e.g., backward/forward), α' (e.g., yaw), β' (e.g., roll), and γ (e.g., pitch), and changes in the coordinate components are designated as ΔX, ΔY, ΔZ, Δα, Δβ, and Δγ, respectively (see, e.g., FIG. 19).

Figure 20:
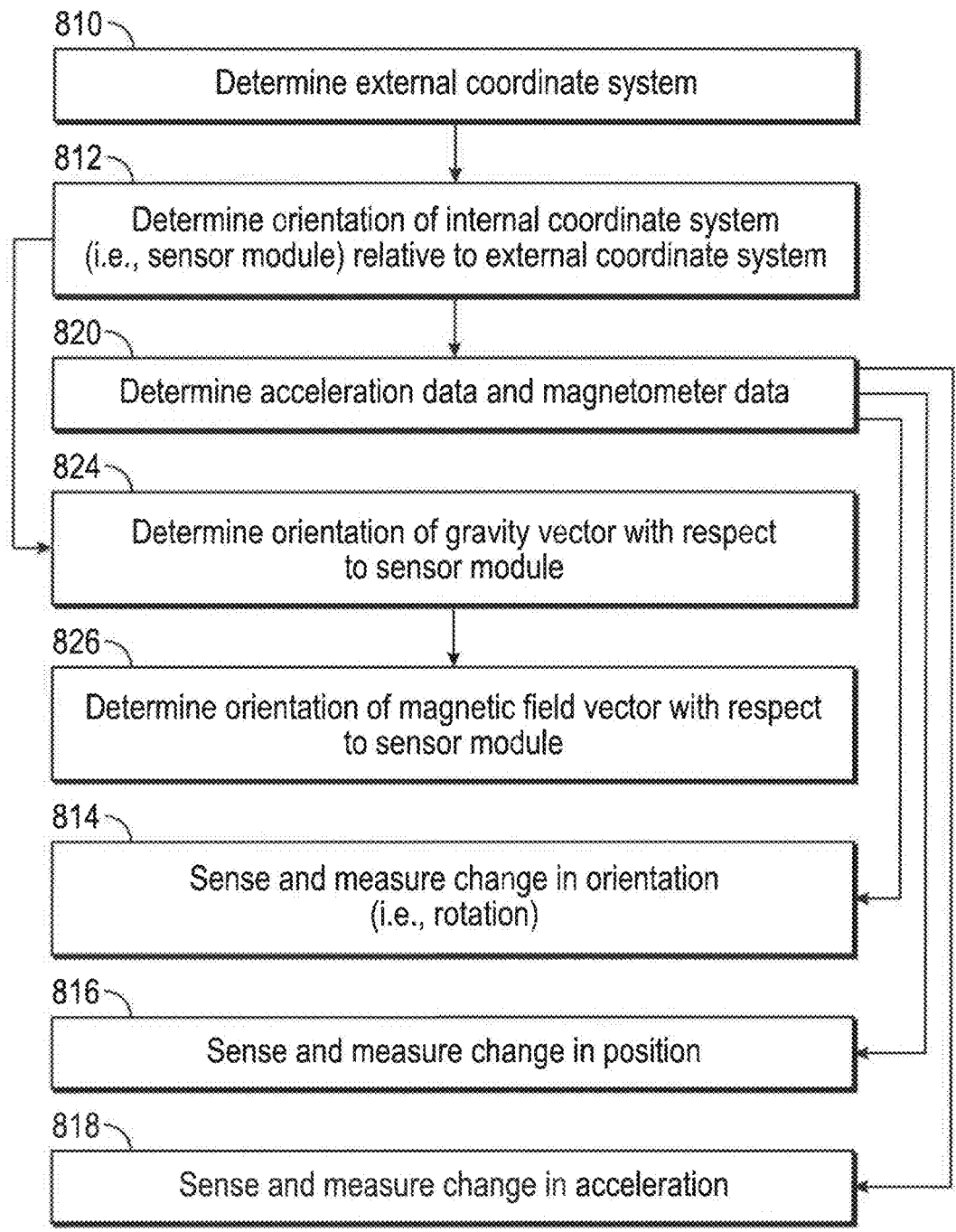
FIG. 20 is a flow chart illustrating operations to determine data relating to motion of an individual, according to an embodiment of the present invention.

For example, as depicted in FIG. 18, in some embodiments acceleration sensor 116 is used to determine the orientation of gravity vector 302 with respect to sensor module 102 (i.e., with respect to internal coordinate system 650) at the first time (see, e.g., operation 824, FIG. 20), and in some embodiments magnetic field sensor 118 is used to determine the orientation of magnetic field vector 304 with respect to sensor module 102 at the first time (see, e.g., operation 826, FIG. 20). In some embodiments, the orientation of internal coordinate system 650 with respect to external coordinate system 600 can be determined based on one or both of gravity vector 302 and magnetic field vector 304 (see, e.g., operation 812, FIG. 20). In this way an initial orientation of individual 100 can be determined based on the initial orientation of sensor module 102 (including internal coordinate system 650) within external coordinate system 600.

In some embodiments, monitoring device 30 determines and/or outputs one or more sensed motion characteristics of individual 100 (see, e.g., operation 820, FIG. 20), including, for example, position of individual 100 or a portion thereof, orientation of individual 100 or a portion thereof, orientation and/or magnitude of speed of individual 100 or a portion thereof, orientation and/or magnitude of acceleration of individual 100 or a portion thereof, orientation and/or magnitude of forces applied to individual 100 or a portion thereof, duration of movement of individual 100 or a portion thereof, posture of individual 100 or a portion thereof, rotation of individual 100 or a portion thereof, and/or a degree of correspondence to a movement data profile, or changes therein.

In some embodiments, for example (see FIG. 19), rotation (e.g., three-dimensional rotation) of individual 100 (including, for example, rotation of individual 100 as a whole or of one or more monitored portions of individual 100, recognizing that portions of individual 100 may move relative to each other) can be determined between the first time and a second time (see, e.g., operation 814, FIG. 20), where individual is in motion at the second time. In some embodiments, such rotation can be output by monitoring system 30 and/or used by monitoring system 30 for further operations.

For example, in some embodiments the change in orientation of individual 100 between the first time and the second time is determined based on magnetic field data sensed by magnetic field sensor 118 from the first time to the second time. For example, the change in orientation of individual 100 between the first time and the second time may be expressed by the angular difference of axes X', Y', and Z' between the first time and the second time with respect to external coordinate system 600 (depicted as Δα, Δβ, and Δγ).

In some embodiments, for example (see FIG. 19), the change in position of individual 100 between the first time and the second time is determined (see, e.g., operation 816, FIG. 20) based on acceleration data sensed by acceleration sensor 116 from the first time to the second time. In some embodiments, such change in position can be output by monitoring system 30 and/or used by monitoring system 30 for further operations.

For example, the change in position of individual 100 between the first time and the second time may be expressed by the linear difference in position of sensor module 102 along of axes X, Y, and Z between the first time and the second time with respect to external coordinate system 600 (depicted as ΔX, ΔY, and ΔZ).

As described, individual's 100 motion between two points in time can be characterized by change in position and change in orientation of sensor module 102 between the two points in time. In some embodiments, a more complete representation of individual's 100 motion can be characterized by monitoring change in position and change in orientation of sensor module 102 between multiple sequential points in time. In other words, the technique described above for characterizing individual's 100 motion between two points can be repeated from the second time to a third time. Change in position and change in orientation can be measured absolutely (e.g., with continuing reference to the position and orientation of sensor module at the first time (which may be a calibration state), or relatively (e.g., with reference to the immediately preceding position and orientation, or any other sensed position and orientation). As will be appreciated, the greater the rate of sampling of position and orientation, the more complete the representation of individual's 100 motion will be. In some embodiments, where change in position and change in orientation is measured relatively, sensor module 102 may not be calibrated with respect to an external coordinate system.

In some embodiments, monitoring system 30 can determine an indication of the posture of individual 100. In some embodiments, such posture can be output by monitoring system 30 and/or used by monitoring system 30 for further operations. Posture can be determined based on the orientation of a sensor module 102 mounted to individual 100. For example, a sensor module 100 can be mounted on the trunk of individual 100 in a predetermined (or otherwise calibrated) orientation with reference to individual 100, such that monitoring system 30 can determine the posture of individual 100 based on the orientation of sensor module 102 (determined as described above). For example, sensor module 102 may be mounted on individual 100 such that a reference coordinate direction coincides with the direction of a gravity vector or magnetic field vector when individual's 100 trunk is perpendicular to the ground. In some embodiments, if monitoring system 30 detects that the reference coordinate direction coincides with the gravity vector or magnetic field vector, monitoring system 30 may determine that individual 100 is in a standing position. In some embodiments, if monitoring system 30 detects that the reference coordinate direction is orthogonal to the gravity vector or magnetic field vector, monitoring system 30 may determine that individual 100 is in a prone or supine position. In some embodiments, multiple sensor modules 102 can operate similarly mounted to an individual 100 to determine sub-postures of different portions of individual 100, and more complex overall postures of individual 100 may be determined based on comparisons of the determined sub-postures to each other, or to data defining reference postures.

In some embodiments, monitoring system 30 can determine an indication of orientation and/or magnitude of acceleration of individual 100 (together an acceleration vector), and change therein. In some embodiments, such indication of orientation and/or magnitude of acceleration of individual 100 or change therein can be output by monitoring system 30 and/or used by monitoring system 30 for further operations. Magnitude and direction of acceleration can be sensed directly by sensor module 102, with reference to internal coordinate system 650. Monitoring system 30 can determine change in magnitude and direction of acceleration based on this sensed data (see, e.g., operation 818, FIG. 20). Change in magnitude of acceleration from a first time to a second time can be determined by calculating the difference between the magnitude of acceleration sensed by acceleration sensor 116 of sensor module 102 at the first time and the magnitude of acceleration sensed by acceleration sensor 116 of sensor module 102 at the second time. Change in direction of acceleration from a first time to a second time can be determined by calculating the difference between the angle of an acceleration vector 730 (see, e.g., FIG. 19) sensed by acceleration sensor 116 of sensor module 102 at the first time and the angle of acceleration vector 730 sensed by acceleration sensor 116 of sensor module 102 at the second time. Such change in direction of acceleration can be correlated to the corresponding orientation of individual 100 by reference to the orientation of sensor module 102 determined based on magnetic field data sensed by sensor module 102, as described above. Thus, as described, change in orientation, position, magnitude of acceleration, and direction of acceleration can be determined to characterize the motion of individual 100 for a series of points in time.

In some embodiments monitoring system 30 can determine an indication of orientation and/or magnitude of forces applied to or by individual 100, and change therein. In some embodiments, such indication of orientation and/or magnitude of forces applied to individual 100 or change therein can be output by monitoring system 30 and/or used by monitoring system 30 for further operations. In some embodiments, monitoring system 30 can sense acceleration of individual 100, via acceleration sensor 116 of sensor module 102 (e.g., as described above). In some embodiments, monitoring system 30 may receive data representative of a mass of individual 100, which in some embodiments can be input into monitoring system 30, for example, using an interface thereof (e.g., an input of personal computer 204 or portable electronic device 206, such as, for example, a keyboard, microphone, or touchscreen). In some embodiments, in the event that a sensor 102 mounted on individual 100 is mounted on a portion of individual 100 with a separately-identifiable mass (e.g., an arm of individual 100), the mass of individual 100 can be input for that sensor as the mass of the monitored arm of individual 100. In some embodiments, mass of individual 100 can be defined as a default value, which can be overridden in the event a mass of individual 100 is input. In some embodiments, monitoring system 30 can determine force for a given acceleration (e.g., determined as described above) of individual 100 based on the determined acceleration and the mass of individual 100 (e.g., by multiplying mass and acceleration). Force can be determined in any direction, since acceleration can be sensed in any desired direction. For example, lateral (side-to-side), vertical (up-down), and/or longitudinal (front-back) forces applied to or by individual 100 can be determined, as can combinations thereof, based on components of acceleration data sensed in the desired direction. Lateral forces may dominate (i.e., be the strongest component force) when, for example, individual 100 cuts left or cuts right. Vertical forces may dominate when, for example, individual 100 jumps or drops toward the ground. Longitudinal forces may dominate when, for example, individual 100 stops or begins running.

Movement of individual 100 may be represented by one or more sensed motion characteristics, including, for example, position of individual 100 or a portion thereof, orientation of individual 100 or a portion thereof, orientation and/or magnitude of speed of individual 100 or a portion thereof, orientation and/or magnitude of acceleration of individual 100 or a portion thereof, orientation and/or magnitude of forces applied to individual 100 or a portion thereof, duration of movement of individual 100 or a portion thereof, posture of individual 100 or a portion thereof, and/or rotation of individual 100 or a portion thereof, or changes therein. Individual 100 may perform any movement, such as, for example, a jump, a backflip, a cut right, a cut left, a slide, a reverse of direction, a barrel roll, a kick, or a swing.

In some embodiments monitoring system 30 may identify a movement of individual 100 based on one or more of the sensed acceleration data and magnetic field data (which may be associated with the time at which the data was sensed) of individual 100 in performing the movement. For example, if individual 100 performs a backflip, monitoring system 30 may identify that individual 100 has performed a backflip. Any movement of individual 100 may be monitored and identified, including, for example, a throw of an object, a kick of an object, a jump, a jump shot, a layup, a slide, a left turn, a right turn, a reverse in direction, a change in position, a sprint, a pose, a dive).

In some embodiments movement data profiles (i.e., one or more of sensed acceleration data and magnetic field data that define a movement) for one or more movements may be stored within or otherwise accessible by monitoring system 30 such that monitoring system 30 can compare sensed acceleration data and magnetic field data with the movement data profiles.

Figure 21:
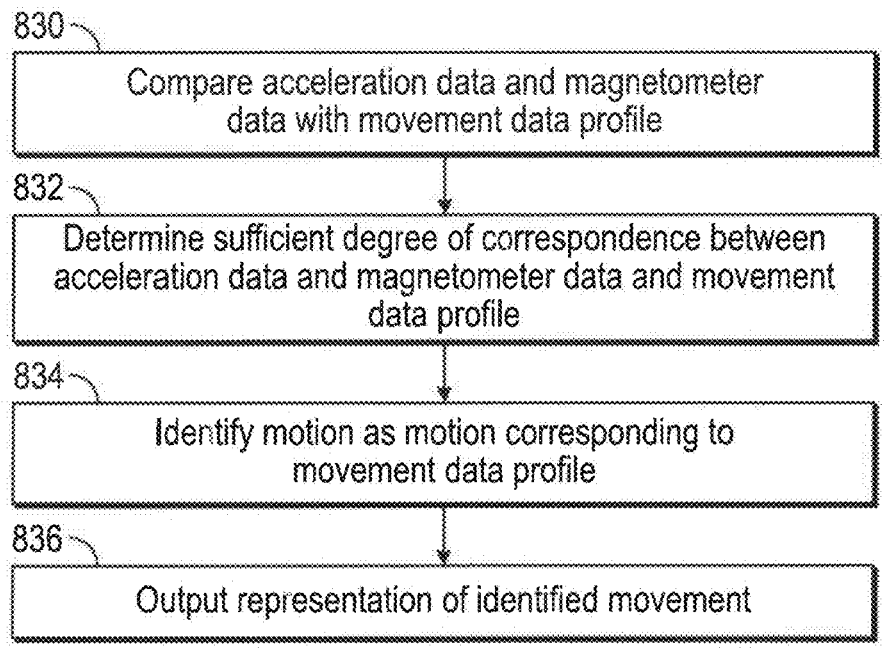
FIG. 21 is a flow chart illustrating operations to identify a motion of an individual, according to an embodiment of the present invention.

In some embodiments, monitoring system 30 may compare sensed acceleration data and magnetic field data of individual 100 with one or more movement data profiles (see, e.g., operation 830, FIG. 21). In some embodiments, monitoring system 30 may perform such comparison continuously.

In some embodiments, upon determining a sufficient degree of correspondence between the sensed acceleration data and magnetic field data and a movement data profile or portion thereof (see, e.g., operation 832, FIG. 21), monitoring system 30 identifies the motion corresponding to that movement data profile as the movement performed by individual 100 (see, e.g., operation 834, FIG. 21). In some embodiments, a sufficient degree of correspondence is determined where the difference between the sensed acceleration data and magnetic field data and the movement data profile is less than a predetermined threshold (the threshold may be different for different movement data profiles).

In some embodiments, the identified motion can be stored by monitoring system 30 as described herein (e.g., in memory 114 of sensor module 102, or in a memory of server 202, personal computer 204, or portable electronic device 206) In some embodiments, characteristics of the identified motion are determined and stored in association with the identified motion (e.g., acceleration, speed, distance moved, duration of movement, or forces acting on or applied by individual 100 during the identified motion).

In some embodiments, the identified motion is output in a manner perceivable by individual 100 or other person (e.g., via a visual display or audio speaker of or in communication with sensor module 102, portable electronic device 206, or personal computer 204) (see, e.g., operation 836, FIG. 21). In some embodiments, the identified motion is output in conjunction with characteristics of the identified motion in a manner perceivable by individual 100 or other person (e.g., via a visual display or audio speaker of or in communication with sensor module 102, portable electronic device 206, or personal computer 204).

In some embodiments, movement data profiles can include expressions of acceleration data and magnetic field data, and variables derived therefrom (e.g., force, acceleration magnitude, acceleration orientation, magnetic field magnitude, magnetic field orientation), and can be expressed and/or stored as data structures within monitoring system 30, for example, as an algorithm, as a graphical curve, or as a lookup table.

Figure 22:
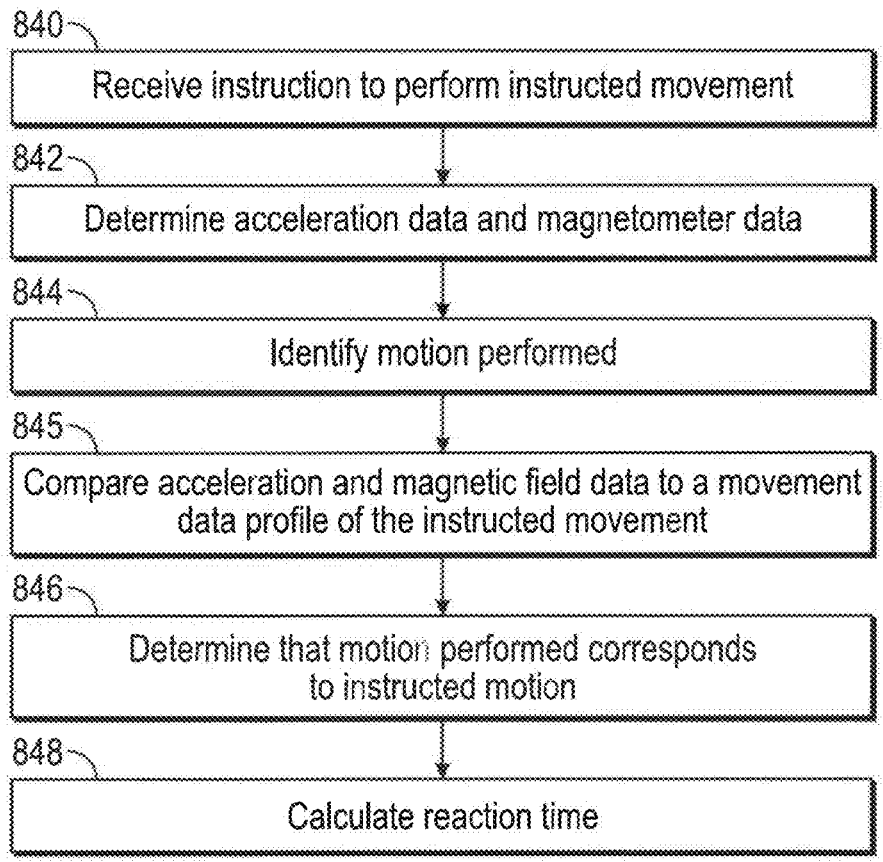
FIG. 22 is a flow chart illustrating operations to determine reaction time of an individual, according to an embodiment of the present invention.

In some embodiments, monitoring system 30 may determine a reaction time of individual 100. In some embodiments, an instruction is communicated to individual 100 to perform a particular instructed movement (e.g., complete a backflip, reach a maximum or target acceleration, reach an optimal or target trunk position). In some embodiments, the instruction may be transmitted to and received by sensor module 102 (e.g., from an external device, such as, for example, portable electronic device 206), and output from sensor module 102 in a manner perceivable by individual 100 (e.g., via a speaker or display of or in communication with sensor module 102) (see, e.g., operation 840, FIG. 22). In some embodiments, the instruction may be communicated to individual 100 without being passed through sensor module 102. For example, an external device (such as, for example, portable electronic device 206) may output the instruction in a manner perceivable by individual 100 (e.g., via a speaker or display of or in communication with electronic device 206). In some embodiments, the instruction may be communicated to individual 100 by another person (e.g., by a person operating an external device (such as, for example, portable electronic device 206) yelling the instruction to individual 100 at an appropriate time, where the person may be prompted to do so by the external device).

In some embodiments, monitoring system 30 determines the reaction time of individual 100 to be the time between an instruction being sent or received as described above, and the time individual begins or completes the instructed movement). In some embodiments, acceleration data and magnetic field data of individual 100 are determined after an instruction is sent or received (see, e.g., operation 842, FIG. 22), to identify a movement performed by individual 100 (see, e.g., operation 844, FIG. 22). In some embodiments, acceleration data and magnetic field data derived from individual 100 are compared to a movement data profile of the instructed movement (see, e.g., operation 485, FIG. 22). In some embodiments, if the movement performed by individual 100 corresponds to a movement data profile of the instructed movement (see, e.g., operation 846, FIG. 22), monitoring system 30 calculates the reaction time of individual 100 as the elapsed time between sending or receiving the instruction and beginning or completing the instructed movement (see, e.g., operation 848, FIG. 22). In some embodiments, a degree of correspondence may be determined by monitoring system 30 for a monitored movement of individual 100, where the degree of correspondence provides an indication of how closely the movement of individual 100 corresponded to a movement data profile. Such a degree of correspondence can be based on the magnitude of the difference between the sensed acceleration data and magnetic field data and the movement data profile.

In some embodiments, monitoring system 30 can compare such a degree of correspondence with a target degree of correspondence or range thereof, and if the movement of individual 100 does not reach the target or is outside the range, monitoring system 30 may instruct individual 100 to repeat the movement, or may provide an indication that the individual's 100 attempt to perform the instructed movement was not successful. In some embodiments, monitoring system 30 may provide feedback (e.g., via an audio speaker, visual display, or haptic output) to help guide individual 100 through performance of the instructed movement, in order to help individual 100 improve performance of the movement and achieve a greater degree of correspondence with the instructed movement. For example, monitoring system 30 may provide output alerting individual 100 of deficiencies in individual's 100 movement (e.g., by identifying portions of individual's 100 movement where data representing individual's 100 movement deviates most significantly from the movement data profile for the instructed movement).

Figure 23:
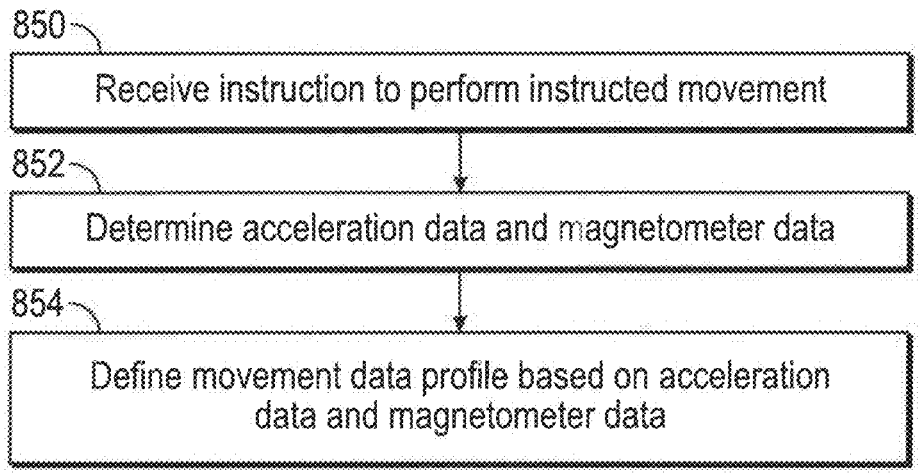
FIG. 23 is a flow chart illustrating operations to define a movement data profile, according to an embodiment of the present invention.

In some embodiments, monitoring system 30 may define a movement data profile for an instructed movement. In some embodiments, an instruction is communicated to individual 100 to perform a particular instructed movement (as described above) (see, e.g., operation 850, FIG. 23). In some embodiments, acceleration data and magnetic field data of individual 100 are determined after an instruction is sent or received (see, e.g., operation 852, FIG. 23). In some embodiments, the sensed acceleration data and magnetic field data are used to define a movement data profile for the instructed movement (see, e.g., operation 854, FIG. 23). Such a movement data profile can be stored and used, for example, in subsequent identification of a movement of individual 100, or of reaction time of individual 100, as described herein. In some embodiments, monitoring system identifies the beginning and end of the movement of individual automatically (e.g., the beginning of the movement may be identified upon sensed acceleration data crossing above a threshold value, remaining above a threshold value for a predetermined period of time, or upon acceleration data and magnetic field data of individual 100 corresponding to a predetermined pattern, and the end of the movement may be identified upon sensed acceleration data crossing below a threshold value, remaining below a threshold value for a predetermined period of time, or upon acceleration data and magnetic field data of individual 100 corresponding to a predetermined pattern).

Defining a movement data profile is described above in terms of an instructed movement for clarity, but is not limited to instructed movements. In some embodiments, individual 100 may select or input an identifier (e.g., a label such as, for example, a text string, a number, an image) for a movement to define (e.g., using an interface including one or more movement identifiers to select from, or an input to input a movement identifier, where the interface or input may be a part of or in communication with sensor module 102, for example, an interface of sensor module 102, personal computer 204, or portable electronic device 206).

In some embodiments, acceleration data derived from motion of individual 100 can be used to determine a jump characteristic of individual 100. For example, in some embodiments acceleration data derived from motion of individual 100 can be used to determine a jump height characteristic (e.g., the maximum height of a jump) of individual 100. Also for example, in some embodiments acceleration data derived from motion of individual 100 can be used to determine a jump force characteristic (e.g., the force applied during a jump) of individual 100.

Figure 24:
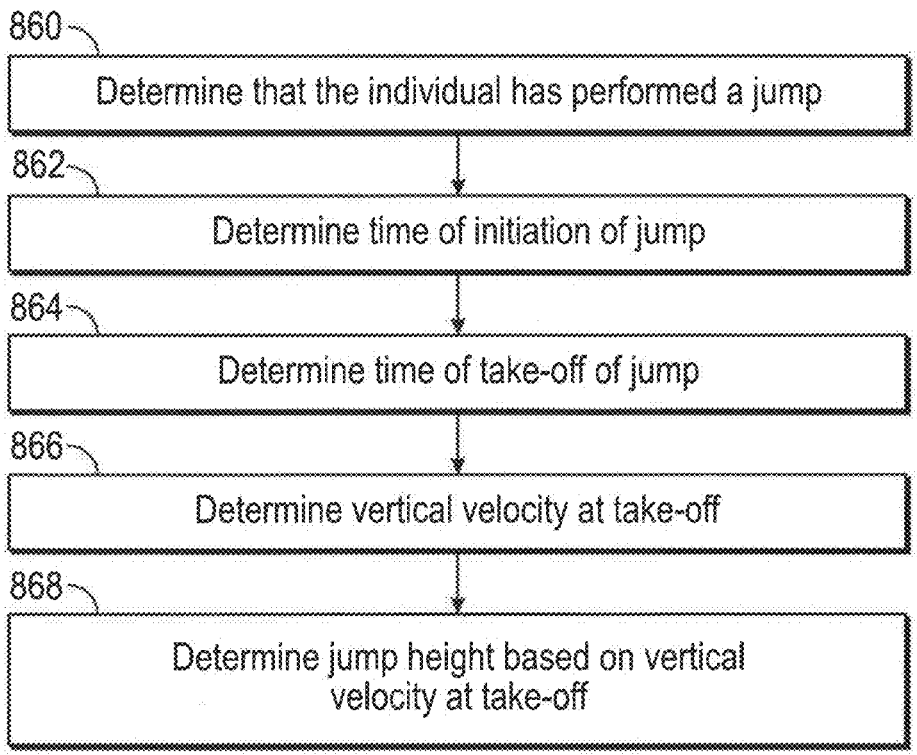
FIG. 24 is a flow chart illustrating operations to determine a jump characteristic of an individual, according to an embodiment of the present invention.
Figure 25:
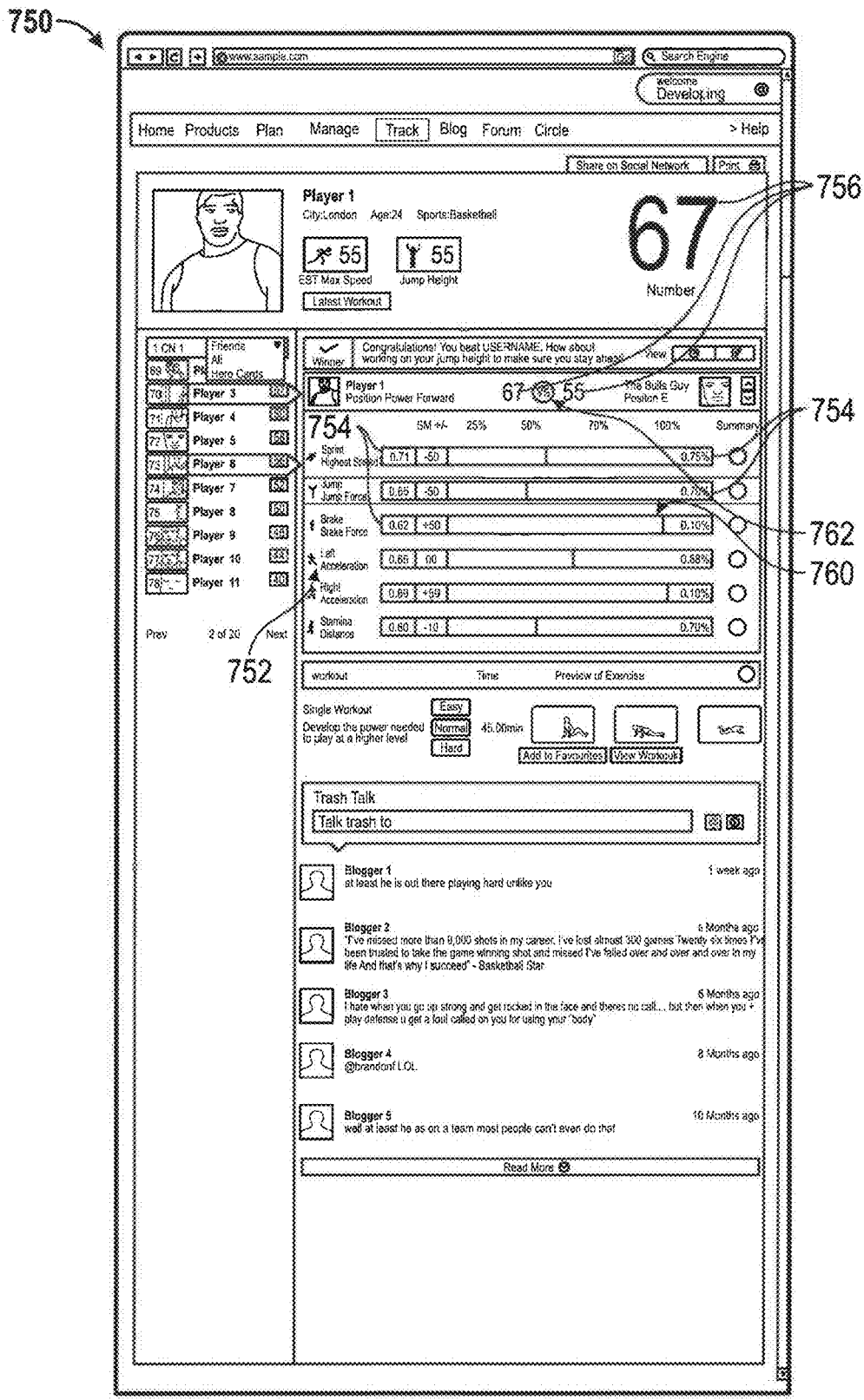
FIG. 25 is an illustration of a display according to an embodiment of the present invention.

In some embodiments, monitoring system 30 determines that individual 100 has performed a jump (see, e.g., operation 860, FIG. 24). In some embodiments, acceleration sensor 116 is an inertial system, and thus does not sense acceleration due to gravity in free flight. Also in free flight, movement of individual 100 typically will not cause significant acceleration. In some embodiments, monitoring system 30 determines that individual 100 has performed a jump by sensing a resultant acceleration of about zero (e.g., acceleration over a period of at least 100 ms characterized by a mean resultant acceleration of less than 15% of 1G (i.e., acceleration due to gravity)).

In some embodiments, once it has been determined that a jump has been performed, monitoring system 30 analyzes sensed acceleration data derived from motion of individual 100 from before the jump was detected, to determine a time of initiation of the jump (when the motion leading to take-off was initiated—for example, after bending the legs, the moment the legs begin to extend to propel individual 100 from the ground) (see, e.g., operation 862, FIG. 24), and a time of take-off of the jump (when individual 100 left the ground) (see, e.g., operation 864, FIG. 24). In some embodiments, this acceleration data derived from motion of individual 100 is analyzed based on data stored in a buffer of sensor module 102, as described herein.

In some embodiments, the time of initiation of the jump is determined to be a time during a period immediately preceding takeoff at which resultant acceleration sensed by sensor module 102 is at a minimum for the period. In some embodiments, the period may be for example, about 50 ms. In some embodiments, vertical velocity of sensor module 102 is determined to be zero at the time of initiation of the jump.

In some embodiments, the time of take-off of the jump is determined to be the time at which resultant acceleration sensed by the sensor module reaches about zero. In some embodiments, vertical acceleration of sensor module 102 is sensed between initiation of the jump and take-off of the jump. In some embodiments, monitoring system 30 determines vertical velocity of sensor module 102 at take-off (see, e.g., operation 866, FIG. 24). In some embodiments, monitoring system 30 determines vertical velocity of sensor module 102 at take-off based on the vertical velocity of sensor module 102 and the acceleration data sensed between initiation of the jump and take-off of the jump. In some embodiments, monitoring system 30 determines vertical velocity of sensor module 102 at take-off based on the vertical velocity of sensor module 102 and the acceleration data sensed between initiation of the jump and take-off of the jump by a calculation using the following formula: $V = V_o + adt$.

In some embodiments monitoring system 30 determines a jump characteristic of individual 100 based on the vertical velocity at take-off (see, e.g., operation 868, FIG. 24). In some embodiments monitoring system 30 determines a maximum jump height of the jump of individual 100 based on the vertical velocity at take-off and conservation of energy principles. In some embodiments, monitoring system 30 determines a maximum jump height of the jump of individual 100 by a conservation of energy calculation based on the vertical velocity at take-off, for example, using the formula $½MV_{to}^2=MgH \rightarrow H=V_{to}/2g$; where M is mass of individual 100 (and cancels out), H is maximum jump height, g is acceleration due to gravity, and $V_{to}$ is vertical velocity at take-off.

Figures 28, 29:
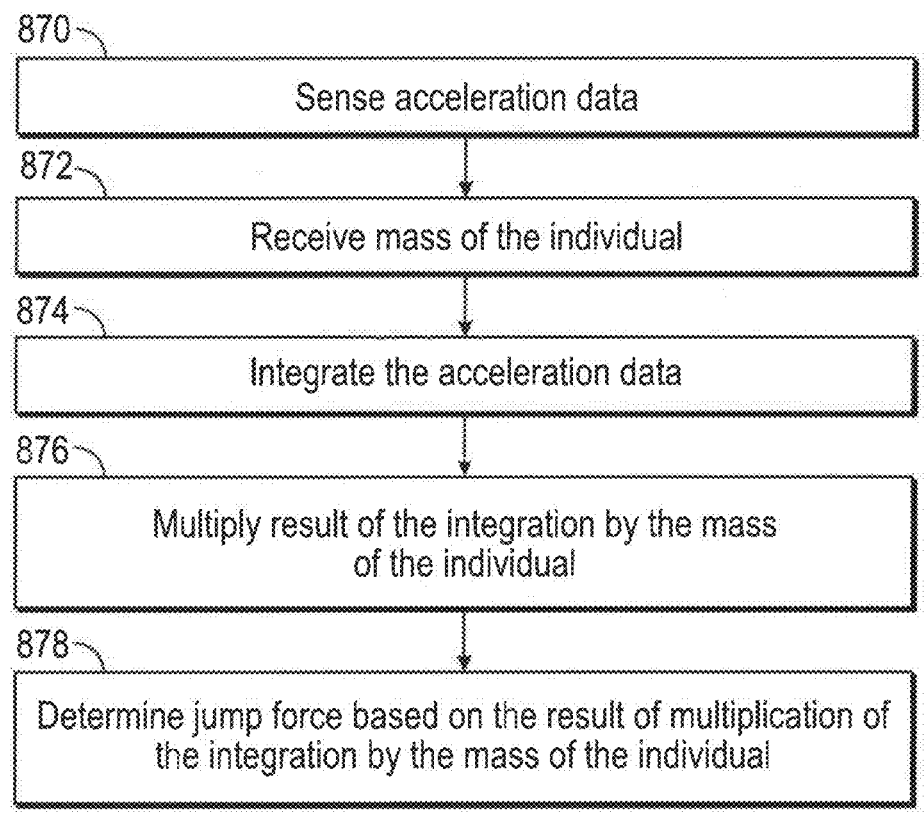
FIG. 28 is a flow chart illustrating operations to determine a jump characteristic of an individual, according to an embodiment of the present invention.
FIG. 29 is a table illustrating characteristics of an individual and of a ball.

In some embodiments monitoring system 30 determines a jump characteristic of individual 100 based on acceleration data sensed during the jump. In some embodiments monitoring system 30 senses acceleration data over one or more periods of time during the jump (see, e.g., operation 870, FIG. 28). In some embodiments monitoring system receives data representative of the mass of individual 100 (which can be input directly into monitoring system 30 by individual 100, e.g., via an interface thereof, or which can be approximated based on a preset default value) (see, e.g., operation 872, FIG. 28). In some embodiments monitoring system 30 integrates the acceleration over one or more periods of time during the jump (see, e.g., operation 874, FIG. 28). In some embodiments, monitoring system multiplies the result of the integration by the mass of individual 100 (see, e.g., operation 876, FIG. 28). In some embodiments, monitoring system 30 determines jump force of the jump of individual 100 based on the integration of the acceleration multiplied by the mass of individual 100 (see, e.g., operation 878, FIG. 28). Jump force of individual 100 can change throughout a jump. In some embodiments, monitoring system 30 determines jump force as described above, for a plurality of periods throughout the jump. In some embodiments, monitoring system 30 determines all or a subset of determined forces throughout the jump as a jump force profile. In some embodiments, monitoring system determines the maximum or minimum jump force throughout the jump.

Monitoring system 30 can output representations of activity metrics of individual 100 (including, for example, forces acting on or applied by individual 100, a motion made by individual 100, a jump characteristic of individual 100, and a reaction time of individual 100) in a manner perceivable by individual 100 or other person (e.g., a coach, trainer, or spectator). Data generated within or received by any component of monitoring system 30 can be transmitted, processed, and output in any suitable manner, including those described herein.

For example, in some embodiments, representations of activity metrics can be output (e.g., via a visual display, an audio speaker, or a haptic output) to a portable electronic device (e.g., portable electronic device 206) or personal computer (e.g., personal computer 204). In some embodiments, monitoring system 30 can determine and output, for example, representations of activity metrics in real time, representations of past activity metrics, representations of predicted activity metrics, representations of comparisons of a current (or most recent) value for an activity metric to a past value for that activity metric, representations of comparisons of one activity metric to a different activity metric, representations of comparisons of a value for an activity metric to a target value for the activity metric, representations of comparisons of a value for an activity metric for an individual 100 to a value for the same (or a different) activity metric for a different individual.

In some embodiments, representations of activity metrics can be presented as functions of one another, or of other variables. For example, jump height can be presented as a function of trunk orientation, or of launch angle of a ball. Also for example, activity metrics can be presented as a function of location (e.g., location on a playing field, proximity to a player, proximity to a goal), as a function of an event (e.g., scoring of a field goal, committing a foul), as a function of an environmental condition (e.g., ambient temperature, precipitation), or as a function of a physiological condition of an individual (e.g., heart rate, body temperature). Information relating to such variables (e.g., location information, event information, environmental condition information, and physiological condition information) may be provided to monitoring system 30 from appropriate sensors incorporated therein, or from elements outside of monitoring system 30 that are in communication with monitoring system 30.

In some embodiments, monitoring system 30 can determine and output such representations in any perceivable way, for example, numerically (e.g., by outputting a value indicative of the activity metric or comparison), textually (e.g., by outputting a word or phrase indicative of the activity metric or comparison), graphically (e.g., by outputting a graph or other image indicative of the activity metric or comparison), or tabularly (e.g., by outputting a table indicative of the activity metric or comparison).

In some exemplary embodiments, identified movements of individual 100 are depicted in a display, such as, for example, output display 750, which, in some embodiments, may be a display of any element described herein, such as, for example, sensor module 102, portable electronic device 206, personal computer 204, group monitoring device 270 (see, e.g., FIGS. 25-27, 29, 31, and 32). In some embodiments, display 750 may be a display screen of a portable electronic device (e.g., portable electronic device 206) or personal computer (e.g., personal computer 204), or may be a printed page. In some embodiments, display 750 may display a representation 752 of each movement of individual 100 identified by monitoring system 30 for a period (e.g., during an athletic activity, during a defined period of time, for the lifetime of monitoring system 30) (see, e.g., FIG. 25).

In some embodiments, display 750 may display an indication of intensity 754 of the identified movements. For example, an indication of the acceleration, speed, distance moved, duration of movement, or force of an identified motion may be displayed. Such indication of intensity 754 may represent the intensity of a single motion, or may represent the intensity of multiple instances of motions identified as the same type (e.g., an average or maximum intensity).

In some embodiments, an indication of overall performance 756 of individual 100 can be determined and displayed, based on sensed acceleration data and magnetic field data. In some embodiments, indication of overall performance 756 of individual 100 can be determined based on characteristics of one or more identified motions of individual 100 (e.g., number of instances of a type of motion, duration of motion or of a type of motion, intensity of motion or of a type of motion). In some embodiments, indication of overall performance 756 can be represented numerically (see, e.g., FIG. 25). In some embodiments, indication of overall performance can be represented graphically (see, e.g., graph 758 in FIG. 27)

In some embodiments, monitoring system 30 may determine, and display 750 may display, any of the representations described herein for a single individual 100 or for multiple different individuals 100. In some embodiments, display 750 may display any of the representations described herein comparatively for two or more individuals. For example, in some embodiments, display 750 may display a comparative bar chart 760 showing the intensity of one or more types of movement of one individual 100 in juxtaposition with the intensity of one or more types of movement of a different individual 100. Also for example, in some embodiments, display 750 may display an overall performance comparison 762, juxtaposing indication of overall performance 756 for one individual 100 with indication of overall performance 756 for a different individual 100.

Figure 26:
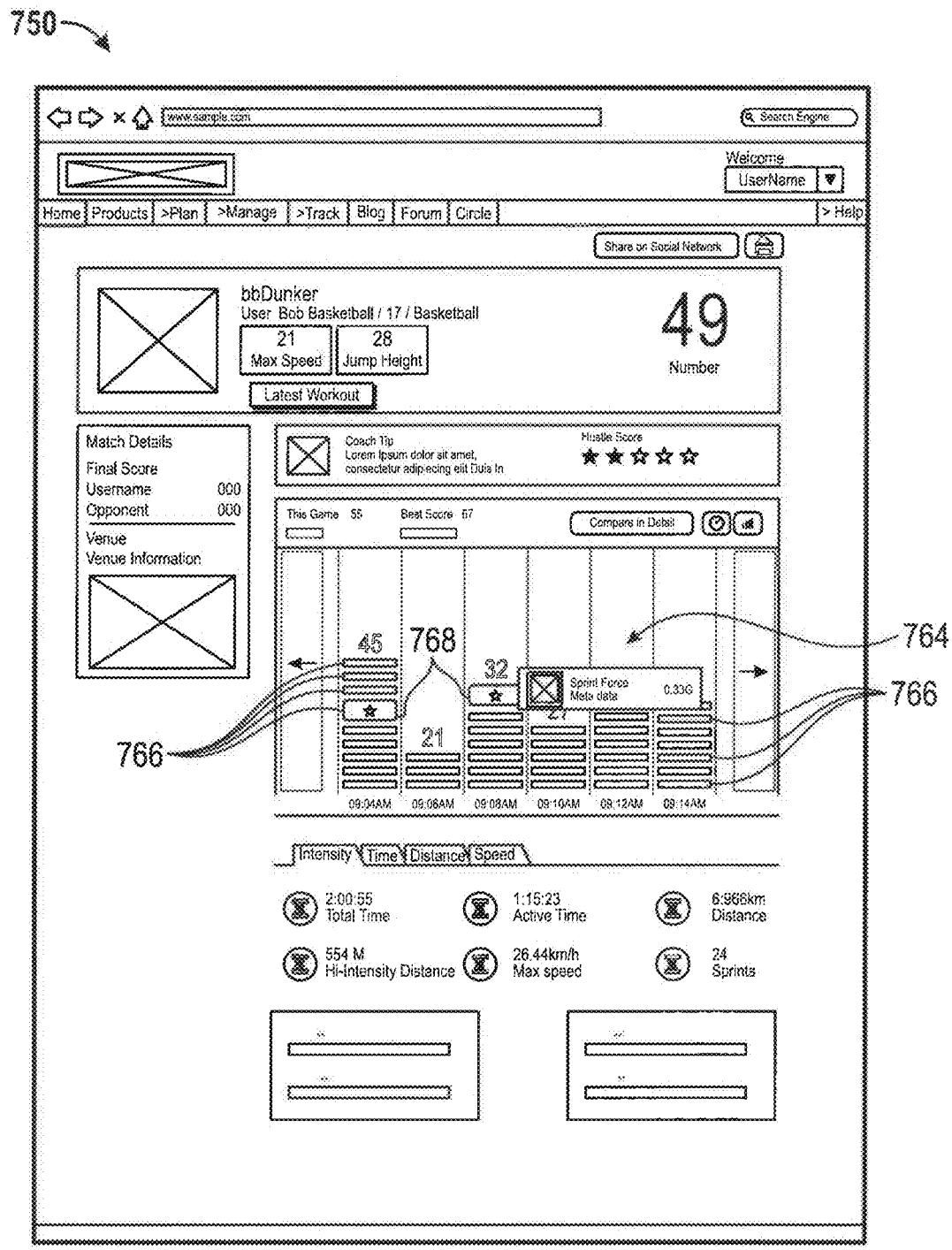
FIG. 26 is an illustration of a display according to an embodiment of the present invention.

In some embodiments, monitoring system 30 may determine, and display 750 may display, a graphical timeline 764 of identified movements performed by individual 100 (see, e.g., FIG. 26). In some embodiments, graphical timeline 764 may include indications 766 of each identified movement, presented according to the time at which the movement occurred. In some embodiments, indications 766 that correspond to identified movements having a characteristic exceeding a threshold may be represented as distinct indications 768, which may appear visually different from other indications 766. For example, distinct indications may be larger than other indications 766, may be differently colored than other indications 766, or may be marked with a graphic, such as, for example, a star.

Figure 27:
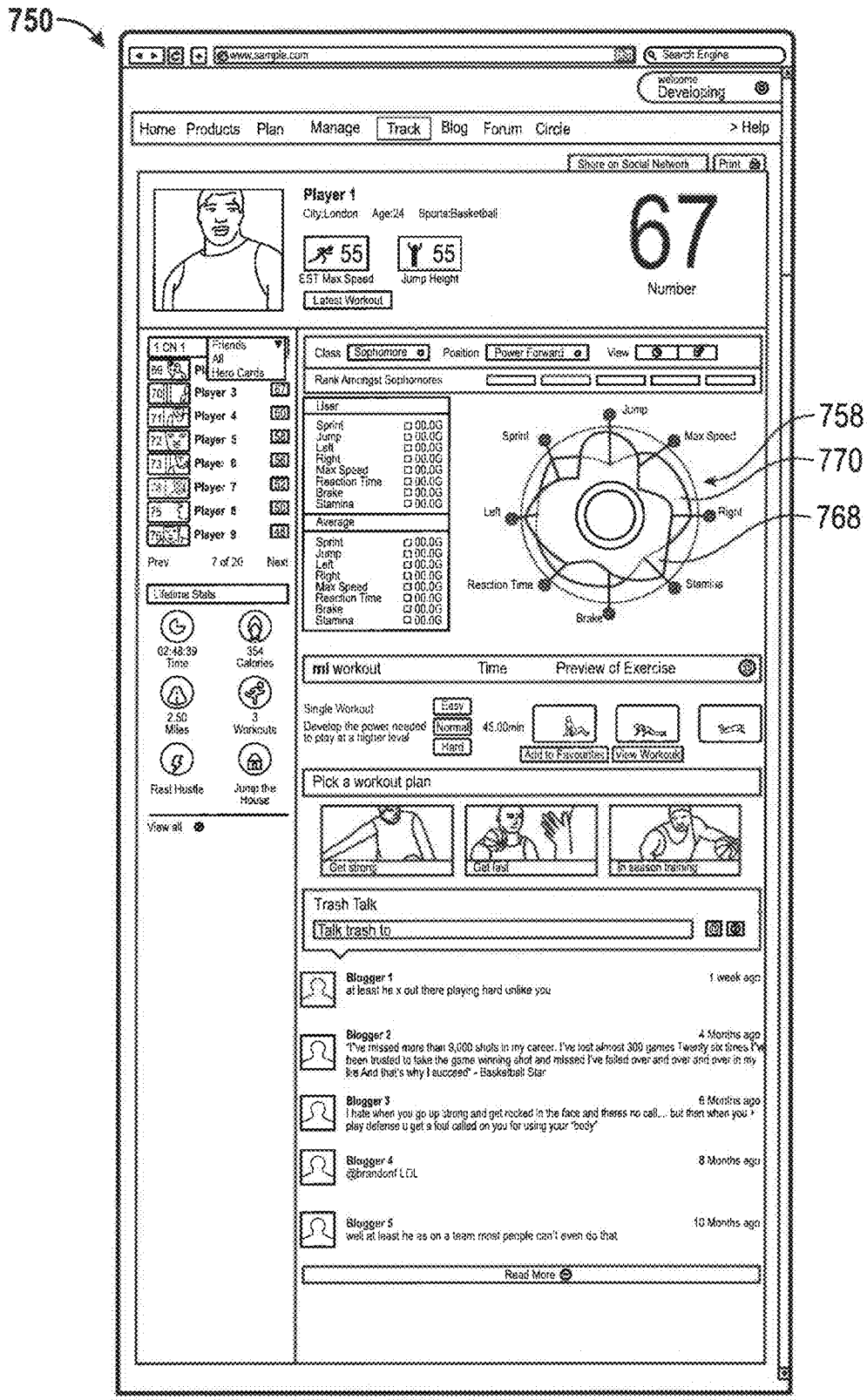
FIG. 27 is an illustration of a display according to an embodiment of the present invention.

In some embodiments, monitoring system 30 may determine, and display 750 may display, a graph (e.g., star plot 758) depicting types and intensities of identified motions of individual 100 (see, e.g., FIG. 27). In some embodiments, star plot 758 may include a representation 768 of types and intensities of identified motions of individual 100 overlaid on a second representation 770 of types and intensities of motions. In some embodiments, second representation 770 may represent averages of types and intensities of motions of a group of individuals. In some embodiments, second representation 770 may represent averages of types and intensities of motions of individual 100 over a different time period than that represented by representation 768. In some embodiments, second representation 770 may represent types and intensities of motions of a different individual than individual 100.

In some embodiments, activity metrics can be output in a game-like manner. Points or other positive or negative feedback may be determined and output based on values for activity metrics for individual 100. Comparisons based on such values or feedback can influence progress in the game. For example, such values or feedback may be compared to past values or feedback for the same individual 100, and improvement may result in positive progress being made in the game (e.g., a higher "level" being designated to a game account of individual 100). Also for example, such values or feedback may be compared to values or feedback of a different individual 100 (including data of, or purported to be of, a professional athlete or other well-known individual), and progress in the game may be determined based on that comparison. Also for example, such values or feedback may be compared to target values or feedback, and progress in the game may be determined based on that comparison. Also for example, in some embodiments, such activity metrics can govern capabilities of a virtual player in a virtual game, by being uploaded to or otherwise accessed by the game (e.g., the maximum jump height of an individual 100 may limit the maximum jump height of a virtual avatar of the individual in a virtual game).

In some embodiments, monitoring system 30 can be used as a standalone monitoring system. In some embodiments, however, monitoring system 30 (or components thereof) can be used in conjunction with or incorporated into other monitoring systems, including for example, those disclosed in commonly owned U.S. patent application Ser. No. 13/077,494, filed Mar. 31, 2011, which is incorporated herein by reference in its entirety.

For example, in some embodiments, any of the characteristics (including values and/or outputs) described herein can be used and/or output in conjunction with characteristics from other monitoring systems, for example, monitoring devices and associated components that sense characteristics (e.g., movement, performance, and/or physiological characteristics) of one or more objects or players engaged in an athletic activity (such as described above, for example, with respect to the group monitoring system). For example, an individual engaged in an athletic activity may be separately monitored by a different monitoring device (e.g., a monitoring device including a heart rate monitor, a global positioning signal receiver, a temperature sensor, a wind sensor, a moisture sensor), or motion of an object (e.g., a ball) used in such activity may be monitored, such that additional characteristics of the individual's performance or object's motion can be monitored and/or output for observation by, for example, a coach, trainer, or spectator, or for later review by the individual himself. Simultaneously, characteristics of individual 100 may be monitored and/or output as described herein with reference to monitoring system 30. The characteristics resulting from monitoring of individual 100 can be used together with the characteristics resulting from other monitoring devices monitoring individual 100 and/or an object. For example, characteristics derived by monitoring individual 100 as described herein with reference to monitoring system 30 can be displayed in a time-correlated manner with characteristics derived from other monitoring devices. Also for example, characteristics derived by monitoring individual 100 as described herein with reference to monitoring system 30 can be expressed as a function of characteristics derived from other monitoring devices (or vice versa). Also for example, new characteristics can be determined based on analysis of both characteristics derived by monitoring individual 100 as described herein with reference to monitoring system 30 and characteristics derived from other monitoring devices (e.g., the time it takes for the individual to react to an instruction to kick a monitored ball).

For example, jump height of individual 100 may be monitored during performance of an athletic activity, and trajectory of a monitored ball may also be monitored during performance of the athletic activity. A monitoring system taking both of these characteristics into account may display (or otherwise output) jump height of individual 100 in conjunction with a characteristic of a sports object such as, for example, the launch angle of the ball after each jump (which, for example, may help individual 100 evaluate characteristics of his jump shot) (see, e.g., FIG. 29). For a series of jumps, maximum jump height of individual 100 may be expressed as a function of trajectory of the ball. Similar comparison, combinations, and/or representations can be provided for any other combination of characteristics derived by monitoring individual 100 as described herein with reference to monitoring system 30 and characteristics derived from other monitoring devices.

In some embodiments, monitoring system 30 can provide real-time feedback to individual 100. Such real-time feedback can be provided during any activity of individual 100, for example, during a training exercise. In some embodiments, monitoring system 30 may monitor individual 100 via sensor module 102 while individual 100 performs a movement (see, e.g., operation 880, FIG. 30). Individual 100 may perform the movement repeatedly, with the goal of improving some aspect of his performance of the movement (e.g., increasing his jump height, decreasing his reaction time, or more accurately performing the movement). It is believed that the provision of timely, concise, periodic feedback about an aspect of a movement that an individual is working to improve, helps the individual to more efficiently improve that aspect of movement. In some embodiments, sensor module 102 coupled to individual 100 while individual 100 is performing such movements transmits data relating to an aspect of the movement (e.g., a selected aspect the individual is working to improve) to a remote device (e.g., portable electronic device 206) (see, e.g., operation 882, FIG. 30). The remote device may receive the data (see, e.g., operation 884, FIG. 30) and display a representation of the data (e.g., via a display screen, audio speaker, or haptic output of or in communication with the remote device) to individual 100 during or immediately following each repetition of the movement (see, e.g., operation 886, FIG. 30). The representation may be, for example, an expression of a value related to the movement (e.g., jump height may be represented by the number of vertical inches jumped, see, e.g., FIG. 31) and/or an expression of a comparison 710 of a value related to the movement to a previous, or target, value related to the movement (e.g., a jump height of 20 inches, where a previous jump height was 19 inches may be displayed with a positive signal, such as a green background 712 or a plus sign 710, to show improvement, while a jump height of 18 inches, where a previous jump height was 19 inches, may be displayed with a negative signal, such as a red background 712 or a minus sign, to show decrease in performance, see, e.g., FIG. 31). Data from repeated movements can be stored for later display and analysis (e.g., display of a graph showing a representation of each movement, for example, as shown in FIG. 32).

For example, in some embodiments, monitoring system 30 can determine jump height of a jump of individual 100 (as described above), and can output (e.g., automatically) a representation of the jump height of the jump to a remote device being viewed by individual 100 (e.g., portable electronic device 206). To facilitate viewing by individual 100, the remote device may be located such that its output is perceivable by individual 100 during performance of the movement, and the representation may occupy substantially all of a display of the remote device. In this way, individual 100 receives immediate feedback as to the height of the jump. Monitoring system 30 can then determine jump height of any number of jumps of individual 100 and can similarly output representations of the jump height of each jump. Such operations can be repeated as desired. Real-time knowledge of individual's 100 jump height can help individual 100 understand the progress individual 100 is making in improving his jump height, for example, by allowing individual 100 to make adjustments to his movement form and immediately determine the effects of such adjustments. Having such knowledge is believed to drive more rapid improvement than would be achieved without having such knowledge.

For example, in some embodiments, monitoring system 30 can determine activity metrics of the movement of individual 100 (determined as described herein), including, for example, reaction time, acceleration, applied forces, extent of movement, and change in position, and can output (e.g., automatically) a representation of such activity metrics of a first movement to a remote device being viewed by individual 100 (e.g., portable electronic device 206). In this way, individual 100 receives immediate feedback as to the activity metric(s) of the first movement. The instruction to perform an action (e.g., triggering the beginning of the timed period for determining reaction time) can be provided to individual 100 via the remote device being viewed by individual 100. For example, the instruction may be provided via an audio or visual output from the remote device. In some embodiments, monitoring system 30 can be configured to instruct a single movement repeatedly. In some embodiments, monitoring system 30 can be configured to instruct one of a set of movements (e.g., a movement can be selected at random from a database of movement data profiles). In some embodiments, the timing of the instruction output may vary (e.g., be randomized within a given range), in some embodiments a countdown may be displayed to help prepare individual 100 for an impending instruction, and in some embodiments initiation of such timing and/or countdown may depend on a determination by monitoring system 30 that individual 100 is stationary. The instruction can be, for example, a word describing the instructed movement (e.g., "jump," "dive," "cut left," "backflip"), or simply an output indicating the time to begin an instructed movement where the instructed movement is known (e.g., where monitoring system 30 is configured to instruct a single movement repeatedly). In some embodiments, the instruction is provided by a change in a color or symbol displayed by the remote device (e.g., a display of remote device may change from red to green, indicating that individual 100 should perform a jump; one side of a display device may turn a particular color, indicating that individual 100 should perform a lunge toward that side; or an arrow may be displayed pointing in a particular direction, for example down, indicating that individual 100 should perform a corresponding movement, for example, drop to a prone position). In some embodiments, after outputting the instruction, monitoring system 30 can determine activity metrics of the movement of individual 100 (determined as described herein), including, for example, reaction time, acceleration, applied forces, extent of movement, change in position, degree of correspondence to an instructed movement, and can output a representation of the reaction time. Monitoring system 30 can determine reaction time of any number of repeated reactions of individual 100 and similarly output a representation of the reaction time of each reaction. Such operations can be repeated as desired. Real-time knowledge of individual's 100 reaction time can help individual 100 understand the progress individual 100 is making in improving his reaction time, for example, by allowing individual 100 to make adjustments to his movement form and immediately determine the effects of such adjustments. Having such knowledge is believed to help an individual achieve more rapid improvement than would be achieved without having such knowledge.

In some embodiments, monitoring system 30 can determine a degree of correspondence of a movement of individual 100, and may provide an indication (e.g., via an audio speaker, visual display, or haptic output of, for example, portable electronic device 206 and/or group monitoring device 270) of such degree of correspondence to individual 100 immediately following performance of the movement. In some embodiments, monitoring system 30 can compare such degree of correspondence with a target degree of correspondence or range thereof If the movement of individual 100 does not reach the target or is outside the range, monitoring system 30 may immediately instruct individual 100 to repeat the movement, or may provide an indication that individual's 100 attempt to perform the instructed movement was not successful. In some embodiments, monitoring system 30 may provide feedback (e.g., via an audio speaker, visual display, or haptic output) to help guide individual 100 through performance of the instructed movement, in order to help individual 100 improve performance of the movement and achieve a greater degree of correspondence with the instructed movement. For example, monitoring system 30 may provide output alerting individual 100 of deficiencies in individual's 100 movement (e.g., by identifying portions of individual's 100 movement where data representing individual's 100 movement deviates most significantly from the movement data profile for the instructed movement).

In some embodiments, a plurality of individuals 100 may be monitored. For example, a plurality of individuals 100 may be monitored via a plurality of sensor modules 102 by a plurality of monitoring systems 30, or a plurality of individuals 100 may be monitored via a plurality of sensor modules 102 by the same monitoring system 30. Such individuals 100 may be monitored in any manner desired, for example, simultaneously, at different times, while participating in different athletic activities, while participating in the same athletic activity. Activity metrics derived from each of the plurality of individuals and activity metrics can be similarly compared, combined, and/or represented as described above. Such comparison, combination, and/or representations can be made based on each individual considered separately (see, e.g., FIG. 25, which shows two individuals separately compared), on a subset of individuals grouped together (e.g., a team, midfielders of a team), or on all monitored individuals. In a game setting, such comparison, combination, and/or representations can be correlated to game events, such as a goal, a ball traveling out-of-bounds, a penalty kick, or a jump ball, which can be output in relation to contemporaneous activity metrics of individual(s) 100 as described.

Such comparing, combining, and/or representing data derived from monitoring individual(s) 100 and/or monitored objects can provide benefits to, for example, the individuals participating in an athletic activity, coaches, spectators, physicians, and game officials. Such persons may interact or work together during a session of athletic activity for a variety of reasons.

For example, it may be desired that a coach monitors the performance of the monitored individual(s) 100 and makes recommendations or otherwise influences their performance in order to maximize fitness level of individual(s) 100. Alternatively or additionally, it may be desired that the coach monitors and influences individual(s) 100 to help maximize the effectiveness of individual(s) 100 in the athletic activity. Further, it may be desired that the coach monitors and influences individual(s) 100 to help maximize the probability of success in the athletic activity (where success may be, for example, defeating an opposing team in a game, such as, for example, soccer, or achieving/maintaining a desired level of fitness for one or more individual(s) 100 participating in the athletic activity). A session of athletic activity may include, for example, a training session (e.g., a field session, a gym session, a track session) or a competitive session (e.g., a soccer match or a basketball game).

In some exemplary embodiments, the coach may monitor one or more individual(s) 100 and/or monitored objects and may provide feedback to individual(s) 100 in order to track and maintain or improve the health, safety, and/or performance of individual(s) 100.

The coach must consider these and other goals, monitor the activity of individual(s) 100 and/or monitored objects, and make decisions to influence the performance of individual(s) 100 both individually and as a group. In doing so, the coach depends on information about individual(s) 100 and their performance while participating in a session of athletic activity. A monitoring system (e.g., monitoring system 30) that provides data about individual(s) 100 (and/or monitored objects interacted with by the individuals) can provide the coach with easy-to-understand information about individuals participating in the athletic activity, beyond that which can be directly observed, thereby facilitating quick and effective decision-making by the coach to maximize the probability of achieving success in the athletic activity.

As noted above, a variety of information may be communicated between any of the elements of monitoring system 30, including, for example, sensor module 102, personal computer 204, portable electronic device 206, network 200, and server 202. Such information may include, for example, activity metrics, device settings (including sensor module 102 settings), software, and firmware.

Communication among the various elements of the present invention may occur after the athletic activity has been completed or in real-time during the athletic activity. In addition, the interaction between, for example, sensor module 102 and personal computer 204 and the interaction between, for example, the personal computer 204 and the server 202 may occur at different times.

In the case of a plurality of monitored individuals 100 and/or monitored objects, in some embodiments sensor devices (e.g., sensor module(s) 102) associated with each monitored individual 100 and/or object may each transmit data to a different associated remote device (e.g., personal computer 204 and/or portable electronic device 206). In some embodiments, multiple sensor devices (e.g., sensor module(s) 102) associated with monitored individual(s) 100 and/or objects may transmit data to the same associated remote device. In some embodiments, multiple sensor devices (e.g., sensor module(s) 102) associated with monitored individual(s) 100 and/or objects may transmit data to an intermediate device (e.g., a computer acting as a "base station" to receive data locally and transmit such data to one or more external devices, with or without processing such data, for example, as described herein) for re-transmission to remote devices (e.g., via network 200 and/or server 202). Such data transmission as described can occur in substantially real time (e.g., during an athletic activity, for real-time analysis), or can occur after completion of the athletic activity (e.g., for post-game analysis). Data transmitted can be in any form ranging from raw data sensed by sensors (e.g., acceleration sensor 116 and magnetic field sensor 118 of sensor module 102) or data resulting from any processing operation (e.g., such identifying, determining, calculating, or storing as described herein). Any processing of the data as described herein can take place at any device that receives data transmission as described.

The foregoing description of the specific embodiments of the monitoring system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

It is to be understood that the phraseology or terminology used herein is for the purpose of description and not of limitation. The breadth and scope of the present invention should not be limited by any of the above-described exemplary embodiments, but should be defined only in accordance with the following claims and their equivalents.

What is claimed is:

1. A method of monitoring an individual engaged in an athletic activity, the method comprising:
    detecting movement of the individual at a first time using a sensor module inseparably coupled to a textile material of a garment configured to be worn by the individual engaged in the athletic activity;
    determining that the movement of the individual corresponds to a predetermined activation movement;
    the sensor module entering an active state in response to the determination that the movement of the individual corresponds to the predetermined activation movement; and
    detecting movement of the individual at a second time while the sensor module is in the active state.

2. The method of claim 1, wherein the sensor module senses magnetic field data and acceleration data.

3. The method of claim 2, further comprising:
    comparing the magnetic field data and the acceleration data with a lookup table; and
    identifying a movement of the individual based on the comparison,.

4. The method of claim 2, wherein sensing magnetic field data and acceleration data comprises:
    sensing first magnetic field data and first acceleration data at a first time; and
    sensing second magnetic field data and second acceleration data at a second time.

5. The method of claim 3, further comprising:
    determining an initial spatial orientation of the individual;
    determining a change in spatial orientation of the individual;
    determining an activity metric based on the change in the spatial orientation; and
    providing an output that conveys the activity metric.

6. The method of claim 5, wherein comparing the magnetic field data and the acceleration data with a lookup table comprises:
    comparing the initial spatial orientation of the individual and the change in the special orientation of the individual to the lookup table.

7. The method of claim 1, wherein the sensor module comprises a sensor, a radio antenna configured to transmit data generated by the sensor, and a flexible printed circuit board.

8. The method of claim 1, wherein an exterior of the sensor module is portless.

9. A system for monitoring an individual engaged in an athletic activity, the system comprising:
    a processor,
    a sensor module inseparably coupled to a textile material of a garment worn by the individual engaged in the athletic activity, the sensor module further comprising:
        a sensor;
        a radio antenna configured to transmit movement data generated by the sensor to the processor; and
        a flexible printed circuit board,
    wherein the processor is configured to compare the movement data to a lookup table to determine an activity metric.

10. The system of claim 9, wherein the sensor module is powered by a capacitor.

11. The system of claim 9, wherein the sensor is a single-purpose sensor configured to sense a single characteristic, and
    wherein the sensor module comprises no sensor in addition to the single-purpose sensor.

12. The system of claim 11, wherein the single characteristic is one of magnetic field data and acceleration data.

13. A method for monitoring an individual engaged in an athletic activity, the method comprising:
    detecting movement of the individual using a sensor module inseparably coupled to a textile material of a garment configured to be worn by the individual engaged in the athletic activity;
    recording movement data resulting from the detection of movement;
    determining a correlation between the movement data and an activity metric by reference to a data structure; and
    providing an output that conveys the activity metric.

14. The method of claim 13, wherein the sensor senses one of acceleration data and magnetic field data.

15. The method of claim 13, further comprising:
    determining a first orientation and a first acceleration of the individual at a first time; and
    determining a second orientation and a second acceleration of the individual at a second time.

16. The method of claim 15, wherein the determination of the first orientation and first acceleration is based on first magnetic field data and first acceleration data, and wherein the determination of the second orientation and second acceleration is based on second magnetic field data and second acceleration data.

17. The method of claim 13, wherein providing the output comprises:
    transmitting data representative of the identified movement of the individual; and
    displaying a representation of the data representative of the identified movement on a display.

18. The method of claim 13, wherein the sensor module is sewn, laser welded, or adhered to the garment.

19. The method of claim 13, wherein the output is conveyed via an external component removably coupled to the textile material of the garment and configured to electrically connect with the sensor module.

20. The method of claim 13, wherein the sensor module is sealed within a waterproof membrane.

* * * * *